US012648355B2

(12) United States Patent
Inoue et al.

(10) Patent No.: US 12,648,355 B2
(45) **Date of Patent: *Jun. 2, 2026**

(54) LIGHT-EMITTING ELEMENT, COMPOUND, ORGANIC COMPOUND, DISPLAY MODULE, LIGHTING MODULE, LIGHT-EMITTING DEVICE, DISPLAY DEVICE, LIGHTING DEVICE, AND ELECTRONIC DEVICE

(71) Applicant: Semiconductor Energy Laboratory Co., Ltd., Kanagawa-ken (JP)

(72) Inventors: Hideko Inoue, Atsugi (JP); Miki Kanamoto, Atsugi (JP); Hiromi Seo, Sagamihara (JP); Satoshi Seo, Sagamihara (JP); Tatsuyoshi Takahashi, Atsugi (JP); Tomoka Nakagawa, Atsugi (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/805,886

(22) Filed: Aug. 15, 2024

(65) Prior Publication Data

US 2025/0048926 A1 Feb. 6, 2025

Related U.S. Application Data

(63) Continuation of application No. 18/116,481, filed on Mar. 2, 2023, now Pat. No. 12,069,951, which is a continuation of application No. 16/911,892, filed on Jun. 25, 2020, now Pat. No. 11,600,789, which is a continuation of application No. 16/255,312, filed on Jan. 23, 2019, now Pat. No. 10,700,291, which is a continuation of application No. 15/890,899, filed on Feb. 7, 2018, now Pat. No. 10,193,086, which is a continuation of application No. 14/224,641, filed on Mar. 25, 2014, now Pat. No. 9,905,782.

(30) Foreign Application Priority Data

Mar. 26, 2013 (JP) ................................ 2013-064261

(51) Int. Cl.

| | |
|---|---|
| ***H01L 51/54*** | (2006.01) |
| ***C07D 491/048*** | (2006.01) |
| ***H10K 85/60*** | (2023.01) |
| *H10K 50/11* | (2023.01) |
| *H10K 85/30* | (2023.01) |
| *H10K 101/00* | (2023.01) |
| *H10K 101/10* | (2023.01) |

(52) U.S. Cl.

CPC ..... *H10K 85/6576* (2023.02); *C07D 491/048* (2013.01); *H10K 85/615* (2023.02); *H10K 85/657* (2023.02); *H10K 85/6572* (2023.02); *H10K 85/6574* (2023.02); *H10K 50/11* (2023.02); *H10K 85/342* (2023.02); *H10K 85/631* (2023.02); *H10K 2101/10* (2023.02); *H10K 2101/90* (2023.02)

(58) Field of Classification Search

None

See application file for complete search history.

(56) References Cited

U.S. PATENT DOCUMENTS

| | | | |
|---|---|---|---|
| 7,312,226 | B2 | 12/2007 | Hurley et al. |
| 7,326,712 | B2 | 2/2008 | Hurley et al. |
| 7,326,713 | B2 | 2/2008 | Hurley et al. |
| 7,335,662 | B2 | 2/2008 | Hurley et al. |
| 8,007,927 | B2 | 8/2011 | Lin et al. |
| 8,221,905 | B2 | 7/2012 | Lin et al. |
| 8,367,850 | B2 | 2/2013 | Ma et al. |
| 8,415,031 | B2 | 4/2013 | Xia et al. |
| 8,455,111 | B2 | 6/2013 | Ohsawa et al. |
| 8,552,018 | B2 | 10/2013 | Hurley et al. |
| 8,580,402 | B2 | 11/2013 | Lin et al. |
| 8,586,204 | B2 | 11/2013 | Xia et al. |
| 8,652,652 | B2 | 2/2014 | Brooks et al. |
| 8,736,157 | B2 | 5/2014 | Seo et al. |
| 8,822,708 | B2 | 9/2014 | Ma et al. |
| 8,866,377 | B2 | 10/2014 | Adamovich et al. |
| 8,921,549 | B2 | 12/2014 | Inoue et al. |
| 8,999,988 | B2 | 4/2015 | Hurley et al. |
| 9,123,903 | B2 | 9/2015 | Lin et al. |
| 9,123,907 | B2 | 9/2015 | Seo et al. |

(Continued)

FOREIGN PATENT DOCUMENTS

| | | | |
|---|---|---|---|
| CN | 101878553 | A | 11/2010 |
| CN | 102341401 | A | 2/2012 |

(Continued)

OTHER PUBLICATIONS

Screen for Chemicals that Extend Yeast Lifespan, https://pubchem.ncbi.nlm.nih.gov/assay/assay.cgi?aid=775, 2007, PubChem BioAssay.

(Continued)

*Primary Examiner* — Andrew K Bohaty

(74) *Attorney, Agent, or Firm* — Husch Blackwell LLP

(57) ABSTRACT

Alight-emitting element having high emission efficiency is provided. A light-emitting element having a low driving voltage is provided. A novel compound which can be used for a transport layer or as a host material or a light-emitting material of a light-emitting element is provided. A novel compound with a benzofuropyrimidine skeleton is provided. Also provided is a light-emitting element which includes the compound with the benzofuropyrimidine skeleton between a pair of electrodes.

16 Claims, 31 Drawing Sheets

(56) References Cited

U.S. PATENT DOCUMENTS

| | | | |
|---|---|---|---|
| 9,150,551 | B2 | 10/2015 | Suzuki et al. |
| 9,153,786 | B2 | 10/2015 | Ma et al. |
| 9,178,158 | B2 | 11/2015 | Kitano et al. |
| 9,391,283 | B2 | 7/2016 | Ohsawa et al. |
| 9,604,928 | B2 | 3/2017 | Shitagaki et al. |
| 9,905,782 | B2 | 2/2018 | Inoue et al. |
| 10,193,086 | B2 | 1/2019 | Inoue et al. |
| 10,573,829 | B2 | 2/2020 | Shitagaki et al. |
| 10,586,934 | B2 | 3/2020 | Shitagaki et al. |
| 10,593,895 | B2 | 3/2020 | Shitagaki et al. |
| 10,700,291 | B2 | 6/2020 | Inoue et al. |
| 11,600,789 | B2 | 3/2023 | Inoue et al. |
| 12,069,951 | B2 | 8/2024 | Inoue et al. |
| 2006/0187381 | A1 | 8/2006 | Yokozawa |
| 2008/0051414 | A1 | 2/2008 | Hurley et al. |
| 2008/0269239 | A1 | 10/2008 | Harris. et al. |
| 2008/0314965 | A1 | 12/2008 | Roberts et al. |
| 2009/0099165 | A1 | 4/2009 | Hurley. et al. |
| 2009/0143399 | A1 | 6/2009 | Hurley et al. |
| 2009/0153034 | A1 | 6/2009 | Lin et al. |
| 2009/0163545 | A1 | 6/2009 | Goldfarb |
| 2010/0187984 | A1 | 7/2010 | Lin et al. |
| 2011/0178107 | A1 | 7/2011 | Wang et al. |
| 2012/0061654 | A1 | 3/2012 | Rayabarapu et al. |
| 2013/0060037 | A1 | 3/2013 | Lin et al. |
| 2013/0324721 | A1 | 12/2013 | Inoue et al. |
| 2014/0042413 | A1 | 2/2014 | Xia et al. |
| 2014/0103327 | A1 | 4/2014 | Brooks et al. |
| 2015/0001524 | A1 | 1/2015 | Brooks et al. |
| 2015/0021555 | A1 | 1/2015 | Kwong et al. |
| 2015/0372243 | A1 | 12/2015 | Ma et al. |
| 2020/0194692 | A1 | 6/2020 | Shitagaki et al. |

FOREIGN PATENT DOCUMENTS

| | | | |
|---|---|---|---|
| CN | 102449107 | A | 5/2012 |
| CN | 102690274 | A | 9/2012 |
| CN | 103137894 | A | 6/2013 |
| EP | 1776982 | A | 4/2007 |
| EP | 1829879 | A | 9/2007 |
| EP | 1860108 | A | 11/2007 |
| EP | 1860109 | A | 11/2007 |
| EP | 1678166 | B | 7/2009 |
| EP | 2511254 | A | 10/2012 |
| EP | 2703405 | A | 3/2014 |
| JP | 06-220059 | A | 8/1994 |
| JP | 2007-015933 | A | 1/2007 |
| JP | 2007-510627 | | 4/2007 |
| JP | 2008-519794 | | 6/2008 |
| JP | 2011-507910 | | 3/2011 |
| JP | 2011-509247 | | 3/2011 |
| JP | 2011-084531 | A | 4/2011 |
| JP | 2012-515216 | | 7/2012 |
| JP | 2012-186461 | A | 9/2012 |
| JP | 2012-522844 | | 9/2012 |
| JP | 2012-227524 | A | 11/2012 |
| JP | 2014-007397 | A | 1/2014 |
| JP | 2014-192214 | A | 10/2014 |
| JP | 2014-209611 | A | 11/2014 |
| JP | 6186491 | | 8/2017 |
| KR | 2011-0116177 | A | 10/2011 |
| KR | 2012-0026486 | A | 3/2012 |
| KR | 2012-0049135 | A | 5/2012 |
| WO | WO-2005/037825 | | 4/2005 |
| WO | WO-2006/050965 | | 5/2006 |
| WO | WO-2007/090852 | | 8/2007 |
| WO | WO-2007/090853 | | 8/2007 |
| WO | WO-2007/090854 | | 8/2007 |
| WO | WO-2009/021107 | | 2/2009 |
| WO | WO-2009/021126 | | 2/2009 |
| WO | WO-2009/030981 | | 3/2009 |
| WO | WO-2009/069535 | | 6/2009 |
| WO | WO-2009/081222 | | 7/2009 |
| WO | WO-2009/085344 | | 7/2009 |
| WO | WO-2009/086028 | | 7/2009 |
| WO | WO-2009/086303 | | 7/2009 |
| WO | WO-2010/083359 | | 7/2010 |
| WO | WO-2010/118029 | | 10/2010 |
| WO | WO-2012/102967 | | 8/2012 |
| WO | WO-2012/111579 | | 8/2012 |
| WO | WO-2012/137693 | | 10/2012 |
| WO | WO-2014/065073 | | 5/2014 |
| WO | WO-2014/157599 | | 10/2014 |

OTHER PUBLICATIONS

SMR000047385, https://pubchem.ncbi.nlm.nih.gov/summary/summary.cgi?cid=6603401&loc=ec_rcs, May 25, 2006, PubChem Compound.

MLS000039550, https://pubchem.ncbi.nlm.nih.gov/summary/summary.cgi?cid=663679&loc=ec_rcs, Jun. 29, 2005, PubChem Compound.

MLS000558491, https://pubchem.ncbi.nlm.nih.gov/summary/summary.cgi?cid=9551646&loc=ec_rcs, Oct. 20, 2006, PubChem Compound.

International Search Report (Application No. PCT/JP2014/059062) Dated Apr. 22, 2014.

Written Opinion (Application No. PCT/JP2014/059062) Dated Apr. 22, 2014.

Zhao. Y et al., "Synthesis, X-ray Structure and Antitumor Activity of 4-(1,3,4-thiadiazole-2-ylthio)benzo[4,5]furo[3,2-d]pyrimidine Derivatives", Chinese Journal of Organic Chemistry, 2010, vol. 30, No. 7, pp. 1093-1097.

Goled.S et al., "Synthesis and Reactions of 2-Substituted 4-Hydrazinobenzofuro [3,2-d] Pyrimidines and Their Antibacterial Activity", Oriental Journal of Chemistry, 1997, vol. 13, No. 1, pp. 73-75.

Tolkunov.S et al., "Synthesis and Reactions of 2,4-Disubstituted Benzo[b]Furano, Benzo[b]Thieno and Indolo[3,2-d]-1,3-Oxazinium Salts", Chemistry of Heterocyclic Compounds, 1990, vol. 26, No. 11, pp. 1310-1312.

Chinese Office Action (Application No. 201480018325.0) Dated Oct. 31, 2016.

930683-73-1 Registry, STN, Apr. 18, 2007, CAS Registry Record.

Mahajan.S et al., "Studies in Benzofurans: Part IX—Synthesis & Reactions of 4-Hydrazinobenzofuro [3,2-d] Pyrimidines", Indian Journal of Chemistry Section B, Jul. 1, 1980, vol. 19B, No. 7, pp. 596-598.

Cramp.S et al., "Identification and hit-to-lead exploration of a novel series of histamine H4 receptor inverse agonists", Bioorganic & Medicinal Chemistry Letters, Apr. 15, 2010, vol. 20, No. 8, pp. 2516-2519.

Storz.T et al., "Convenient and Practical One-Pot Synthesis of 4-Chloropyrimidines via a Novel Chloroimidate Annulation", Org. Process Res. Dev. (Organic Process Research & Development), 2011, vol. 15, No. 4, pp. 918-924, American Chemical Society.

CAS Registry No. 1284458-37-2, STN International HCAPLUS database, CAS Registry Record.

CAS Registry No. 1284135-04-1, STN International HCAPLUS database, CAS Registry Record.

Olah.G et al., "Antimony(V) Chloride", Encyclopedia of Reagents for organic Synthesis, Apr. 15, 2001, pp. 1-3.

Basawaraj.R et al., "Synthesis, antimicrobial and antitubercular activies of some new benzofuro [3,2-d] pyrimidine derivatives", Indian Journal of Heterocyclic Chemistry, 2012, vol. 22, No. 1, pp. 21-26.

Basawaraj.R et al., "Synthesis and biological activities of pyrazolinobenzofuro [3,2-d] pyridimidines", Indian Journal of Heterocyclic Chemistry, 2011, vol. 21, No. 1, pp. 57-60.

Zhao.Y et al., "Synthesis and antitumor activities of heterocycle-substituted benzo [4,5] furo [3,2-d] pyrimidines", Chinese Journal of Synthetic Chemistry, Dec. 31, 2011, vol. 19, No. 3, pp. 321-324.

1148058-92-7/RN, May 21, 2009.

328403-18-5/RN, Mar. 22, 2001.

Hirota.T et al., "Polycyclic N hetero compounds. XXXIV. Syntheses and evaluation of antidepressive activity of benzofuro [2,3 e]imidazo[1,2 c]pyrimidines and their precursors", Journal of Heterocyclic Chemistry, 1991, vol. 28, No. 2, pp. 263-267.

(56) References Cited

OTHER PUBLICATIONS

Chinese Office Action (Application No. 201810927266.9) Dated Dec. 2, 2020.
Chinese Office Action (Application No. 201810927267.3) Dated May 12, 2022.

LIGHT-EMITTING ELEMENT, COMPOUND, ORGANIC COMPOUND, DISPLAY MODULE, LIGHTING MODULE, LIGHT-EMITTING DEVICE, DISPLAY DEVICE, LIGHTING DEVICE, AND ELECTRONIC DEVICE

This application is a continuation of copending U.S. application Ser. No. 18/116,481, filed on Mar. 2, 2023 which is a continuation of U.S. application Ser. No. 16/911,892, filed on Jun. 25, 2020 (now U.S. Pat. No. 11,600,789 issued Mar. 7, 2023) which is a continuation of U.S. application Ser. No. 16/255,312, filed on Jan. 23, 2019 (now U.S. Pat. No. 10,700,291 issued Jun. 30, 2020) which a continuation of U.S. application Ser. No. 15/890,899, filed on Feb. 7, 2018 (now U.S. Pat. No. 10,193,086 issued Jan. 29, 2019) which is a continuation of U.S. application Ser. No. 14/224,641, filed on Mar. 25, 2014 (now U.S. Pat. No. 9,905,872 issued Feb. 27, 2018) which are all incorporated herein by reference.

TECHNICAL FIELD

The present invention relates to a light-emitting element, a compound, an organic compound, a display module, a lighting module, a light-emitting device, a display device, a lighting device, and an electronic device.

BACKGROUND ART

As next generation lighting devices or display devices, display devices using light-emitting elements (organic EL elements) in which organic compounds are used for light-emitting substances have been developed rapidly because of their advantages of thinness, lightweightness, high speed response to input signals, low power consumption, and the like.

In an organic EL element, voltage application between electrodes between which a light-emitting layer is provided causes recombination of electrons and holes injected from the electrodes, which brings a light-emitting substance into an excited state, and the return from the excited state to the ground state is accompanied by light emission. Since the wavelength of light emitted from a light-emitting substance is peculiar to the light-emitting substance, use of different types of organic compounds for light-emitting substances makes it possible to provide light-emitting elements which exhibit various wavelengths.

In the case of display devices which are expected to display images, such as displays, at least three-color light, i.e., red light, green light, and blue light are necessary for reproduction of full-color images. Further, in lighting devices, light having wavelength components evenly spreading in the visible light region is ideal for achieving a high color rendering property, but actually, light obtained by mixing two or more kinds of light having different wavelengths is often used for lighting application. Note that it is known that mixing light of three colors of red, green, and blue allows generation of white light having a high color rendering property.

Light emitted from a light-emitting substance is peculiar to the substance as described above. However, important performances as a light-emitting element, such as a lifetime, power consumption, and emission efficiency, are not only dependent on the light-emitting substance but also greatly dependent on layers other than the light-emitting layer, an element structure, properties of a light-emitting substance and a host material, compatibility between them, carrier balance, and the like. Therefore, there is no doubt that many kinds of light-emitting element materials are necessary for a growth in this field. For the above-described reasons, light-emitting element materials with a variety of molecular structures have been proposed (e.g., see Patent Document 1).

As is generally known, the generation ratio of a singlet excited state to a triplet excited state in a light-emitting element using electroluminescence is 1:3. Therefore, a light-emitting element in which a phosphorescent material capable of converting the triplet excited energy to light emission is used as a light-emitting material can theoretically realize higher emission efficiency than a light-emitting element in which a fluorescent material capable of converting the singlet excited energy to light emission is used as a light-emitting material.

As a host material in a host-guest type light-emitting layer or a substance contained in each carrier-transport layer in contact with a light-emitting layer, a substance having a wider band gap or a higher triplet excitation level (a larger energy difference between a triplet excited state and a singlet ground state) than a light-emitting substance is used for efficient conversion of excitation energy into light emission from the light-emitting substance.

However, most of substances used as host materials in the light-emitting elements are fluorescent, and the triplet excited state of the substance is at a lower energy level than the singlet excited state thereof. Therefore, a host material needs to have a wider band gap in the case where a phosphorescent material is used as a light-emitting material than in the case where a fluorescent material is used as a light-emitting material even when the phosphorescent material and the fluorescent material have the same emission wavelength.

Accordingly, to efficiently obtain phosphorescence having a shorter wavelength, a host material and a carrier-transport material each having an extremely wide band gap are necessary. However, it is difficult to develop a substance to be a light-emitting element material which has such a wide band gap while enabling a balance between important characteristics of a light-emitting element, such as low driving voltage and high emission efficiency.

REFERENCE

Patent Document

[Patent Document 1] Japanese Published Patent Application No. 2007-15933

DISCLOSURE OF INVENTION

In view of the above, an object of one embodiment of the present invention is to provide a light-emitting element having high emission efficiency. An object of one embodiment of the present invention is to provide a light-emitting element having a low driving voltage. An object of one embodiment of the present invention is to provide a light-emitting element emitting phosphorescence with high emission efficiency. An object of one embodiment of the present invention is to provide a light-emitting element emitting green to blue phosphorescence with high emission efficiency.

An object of one embodiment of the present invention is to provide a novel compound which can be used for a carrier-transport layer or as a host material or a light-emitting material of alight-emitting element. Specifically, an object of one embodiment of the present invention is to provide a novel compound which makes it possible to obtain a light-emitting element having good characteristics when used in a light-emitting element emitting phosphorescence with a wavelength shorter than that of green.

An object of one embodiment of the present invention is to provide a heterocyclic compound which has a high triplet excitation level ($T_1$ level). Specifically, an object of one embodiment of the present invention is to provide a heterocyclic compound which makes it possible to obtain a light-emitting element having high emission efficiency when used in a light-emitting element emitting phosphorescence with a wavelength shorter than that of green.

An object of one embodiment of the present invention is to provide a heterocyclic compound which has a high carrier-transport property. Specifically, an object of one embodiment of the present invention is to provide a heterocyclic compound which can be used in a light-emitting element emitting phosphorescence with a wavelength shorter than that of green and allows the driving voltage of the light-emitting element to be low.

An object of one embodiment of the present invention is to provide a light-emitting element using the heterocyclic compound.

An object of one embodiment of the present invention is to provide a display module, a lighting module, a light-emitting device, a lighting device, a display device, and an electronic device each using the heterocyclic compound and achieving low power consumption.

Note that the descriptions of these objects do not disturb the existence of other objects. All the objects do not necessarily need to be achieved simultaneously in one embodiment of the present invention. Other objects may be apparent from the description of the specification, the drawings, the claims, and the like.

Any of the above objects can be achieved by a compound having a benzofuropyrimidine skeleton and application of the compound to a light-emitting element.

One embodiment of the present invention is a compound represented by General Formula (G1).

(G1)

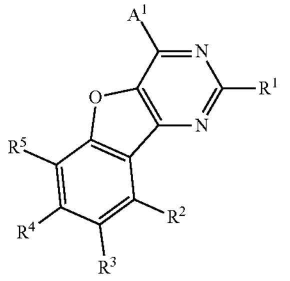

In General Formula (G1), $A^1$ represents any one of a substituted or unsubstituted aryl group having 6 to 100 carbon atoms, a substituted or unsubstituted heteroaryl group, and a group having 6 to 100 carbon atoms and including a substituted or unsubstituted aryl group and a substituted or unsubstituted heteroaryl group. $R^1$ to $R^5$ separately represent any one of hydrogen, an alkyl group having 1 to 6 carbon atoms, a substituted or unsubstituted monocyclic saturated hydrocarbon having 5 to 7 carbon atoms, a substituted or unsubstituted polycyclic saturated hydrocarbon having 7 to 10 carbon atoms, and a substituted or unsubstituted aryl group having 6 to 13 carbon atoms.

Another embodiment of the present invention is a compound represented by General Formula (G2).

(G2)

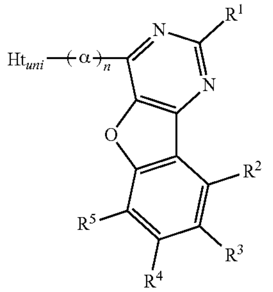

In General Formula (G2), $R^1$ to $R^5$ separately represent any one of hydrogen, an alkyl group having 1 to 6 carbon atoms, a substituted or unsubstituted monocyclic saturated hydrocarbon having 5 to 7 carbon atoms, a substituted or unsubstituted polycyclic saturated hydrocarbon having 7 to 10 carbon atoms, and a substituted or unsubstituted aryl group having 6 to 13 carbon atoms. Further, $\alpha$ represents a substituted or unsubstituted phenylene group and n is an integer from 0 to 4. $Ht_{uni}$ represents a hole-transport skeleton.

A further embodiment of the present invention is the above compound in which n is 2.

A still further embodiment of the present invention is a compound represented by General Formula (G3).

(G3)

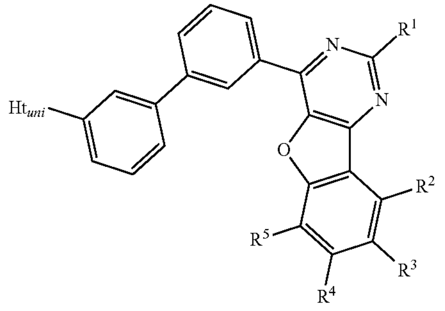

In General Formula (G3), $R^1$ to $R^5$ separately represent any one of hydrogen, an alkyl group having 1 to 6 carbon atoms, a substituted or unsubstituted monocyclic saturated hydrocarbon having 5 to 7 carbon atoms, a substituted or unsubstituted polycyclic saturated hydrocarbon having 7 to 10 carbon atoms, and a substituted or unsubstituted aryl group having 6 to 13 carbon atoms. $Ht_{uni}$ represents a hole-transport skeleton.

A yet still further embodiment of the present invention is any of the above compounds in which $Ht_{uni}$ represents any one of a substituted or unsubstituted dibenzothiophenyl group, a substituted or unsubstituted dibenzofuranyl group, and a substituted or unsubstituted carbazolyl group.

A yet still further embodiment of the present invention is any of the above compounds in which $Ht_{uni}$ is any one of groups represented by General Formulae (Ht-1) to (Ht-6).

(Ht-1)

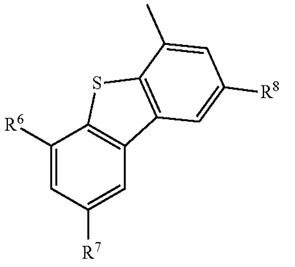

(Ht-2)

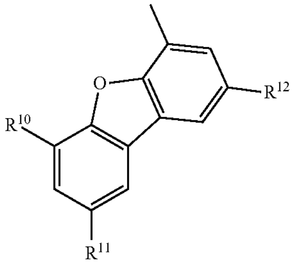

(Ht-3)

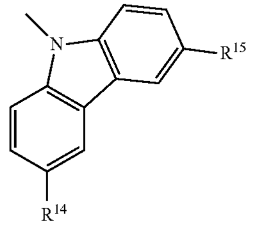

(Ht-4)

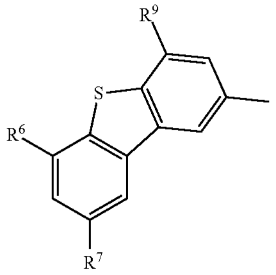

(Ht-5)

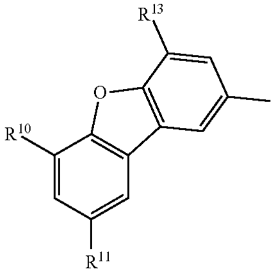

(Ht-6)

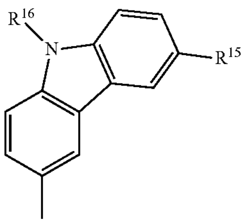

In General Formula 4, $R^6$ to $R^{15}$ separately represent any one of hydrogen, an alkyl group having 1 to 6 carbon atoms, and a substituted or unsubstituted phenyl group. $R^{16}$ represents any one of an alkyl group having 1 to 6 carbon atoms and a substituted or unsubstituted phenyl group.

A yet still further embodiment of the present invention is any of the above compounds in which the substituted or unsubstituted aryl group represented by $A^1$ or the group including a substituted or unsubstituted aryl group and a substituted or unsubstituted heteroaryl group and represented by $A^1$ has 6 to 54 carbon atoms.

A yet still further embodiment of the present invention is any of the above compounds in which the substituted or unsubstituted aryl group represented by $A^1$ or the group including a substituted or unsubstituted aryl group and a substituted or unsubstituted heteroaryl group and represented by $A^1$ has 6 to 33 carbon atoms.

A yet still further embodiment of the present invention is any of the above compounds in which $R^6$ to $R^{15}$ each represent hydrogen.

A yet still further embodiment of the present invention is any of the above compounds in which $R^2$ and $R^4$ each represent hydrogen.

A yet still further embodiment of the present invention is any of the above compounds in which $R^1$ to $R^5$ each represent hydrogen.

A yet still further embodiment of the present invention is any of the above compounds in which $R^2$, $R^4$, and $R^6$ to $R^{15}$ each represent hydrogen.

A yet still further embodiment of the present invention is any of the above compounds in which $R^1$ to $R^{15}$ each represent hydrogen.

A yet still further embodiment of the present invention is a compound represented by Structural Formula (100).

(100)

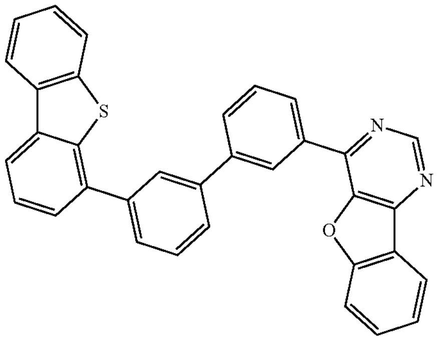

A yet still further embodiment of the present invention is a compound represented by Structural Formula (200).

(200)

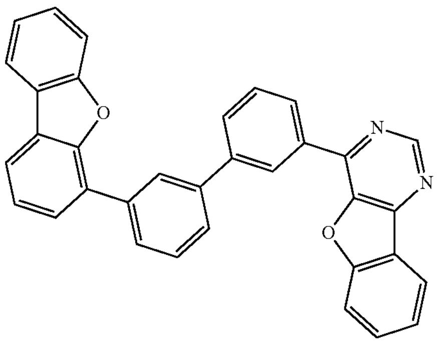

A yet still further embodiment of the present invention is a compound represented by Structural Formula (300).

(300)

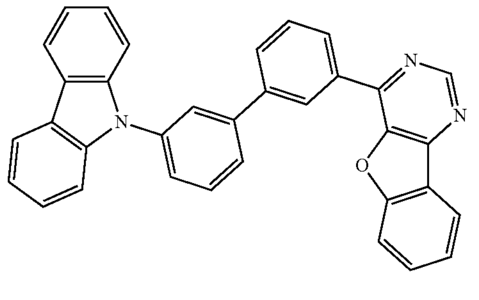

A yet still further embodiment of the present invention is a compound represented by Structural Formula (115).

(115)

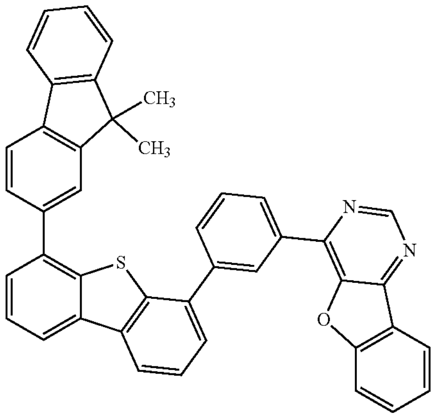

It is preferable that the compound of one embodiment of the present invention be used as a host material in a light-emitting layer or a material of a carrier-transport layer.

A yet still further embodiment of the present invention is a compound which includes any of the above compounds as a partial structure.

Specifically, the yet still further embodiment of the present invention is an organometallic complex which includes any of the above compounds as a ligand.

A yet still further embodiment of the present invention is a light-emitting element that includes a compound with a benzofuropyrimidine skeleton between a pair of electrodes.

A yet still further embodiment of the present invention is a light-emitting element that includes a light-emitting layer between a pair of electrodes. The light-emitting layer contains at least a light-emitting substance and a compound with a benzofuropyrimidine skeleton.

A yet still further embodiment of the present invention is a light-emitting element that includes a light-emitting layer between a pair of electrodes. The light-emitting layer contains an iridium complex and a compound with a benzofuropyrimidine skeleton.

A yet still further embodiment of the present invention is a light-emitting element that includes a carrier-transport layer, specifically, an electron-transport layer between a pair of electrodes. The electron-transport layer contains a compound with a benzofuropyrimidine skeleton.

A yet still further embodiment of the present invention is alight-emitting element that includes a light-emitting layer and an electron-transport layer between a pair of electrodes. At least one of the light-emitting layer and the electron-transport layer contains a compound with a benzofuropyrimidine skeleton.

A yet still further embodiment of the present invention is the above light-emitting element in which the benzofuropyrimidine skeleton is a benzofuro[3,2-d]pyrimidine skeleton.

Typical examples of the above compound with a benzofuro[3,2-d]pyrimidine skeleton are already described above.

A yet still further embodiment of the present invention is a display module including the above light-emitting element.

A yet still further embodiment of the present invention is a lighting module including the above light-emitting element.

A yet still further embodiment of the present invention is a light-emitting device including the above light-emitting element and a unit for controlling the light-emitting element.

A yet still further embodiment of the present invention is a display device including the above light-emitting element in a display portion and a unit for controlling the light-emitting element.

A yet still further embodiment of the present invention is a lighting device including the above light-emitting element in a lighting portion and a unit for controlling the light-emitting element.

A yet still further embodiment of the present invention is an electronic device including the above light-emitting element.

The emission efficiency of the light-emitting element of one embodiment of the present invention is high. Driving voltage of the light-emitting element is low. The light-emitting element exhibits light emission in green to blue regions with high emission efficiency.

The heterocyclic compound of one embodiment of the present invention has a wide energy gap. Further, the heterocyclic compound has a high carrier-transport property. Accordingly, the heterocyclic compound can be suitably used in a light-emitting element, as a material of a carrier-transport layer, a host material in a light-emitting layer, or a light-emitting substance in the light-emitting layer.

One embodiment of the present invention can provide a display module, a lighting module, a light-emitting device, a lighting device, a display device, and an electronic device each using the heterocyclic compound and achieving low power consumption.

BEST MODE FOR CARRYING OUT THE INVENTION

Figure 1A:
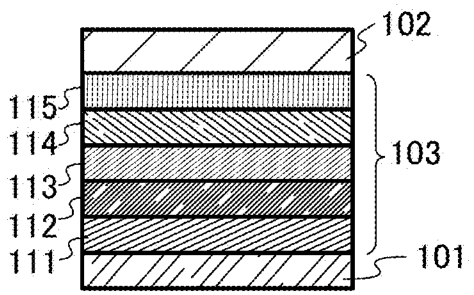
FIGS. 1A and 1B are schematic diagrams of light-emitting elements.

Hereinafter, embodiments of the present invention will be described. It is easily understood by those skilled in the art that modes and details disclosed herein can be modified in various ways without departing from the spirit and scope of the present invention. Therefore, the present invention is not construed as being limited to description of the embodiments.

EMBODIMENT 1

A compound of one embodiment of the present invention which is described in this embodiment is a compound with a benzofuropyrimidine skeleton. A compound with the skeleton excels at transporting carriers (particularly electrons). Owing to this, a light-emitting element with low driving voltage can be provided.

The compound can have a high triplet excitation level ($T_1$ level) and thus can be suitably applied to a light-emitting element that uses a phosphorescent substance. Specifically, the high triplet excitation level ($T_1$ level) of the compound can inhibit transfer of excitation energy of the phosphorescent substance to the compound, which leads to efficient conversion of excitation energy into light emission. A typical example of the phosphorescent substance is an iridium complex.

Note that a specific example of the benzofuropyrimidine skeleton is, but not limited to, a benzofuro[3,2-d]pyrimidine skeleton.

A preferable example of the compound with a benzofuropyrimidine skeleton is represented by General Formula (G1).

(G1)

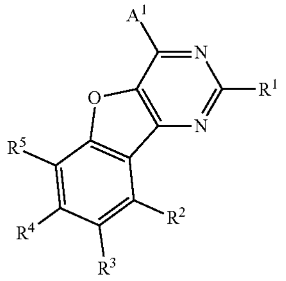

In the formula, $A^1$ represents any one of a substituted or unsubstituted aryl group having 6 to 100 carbon atoms, a substituted or unsubstituted heteroaryl group, and a group having 6 to 100 carbon atoms and including a substituted or unsubstituted aryl group and a substituted or unsubstituted heteroaryl group.

Typical examples of the aryl group having 6 to 100 carbon atoms include groups represented by General Formulae ($A^1$-1) to ($A^1$-6). Note that the groups shown below are merely typical examples and the aryl group having 6 to 100 carbon atoms are not limited to these examples.

($A^1$-1)

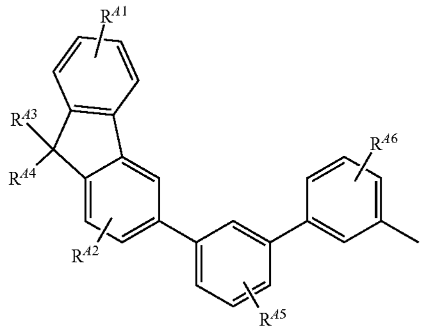

-continued (A$^1$-2)

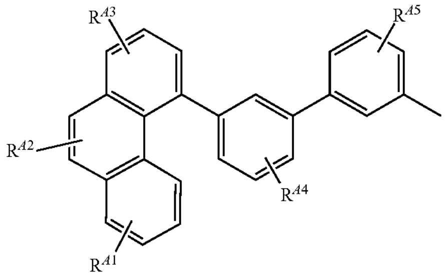

(A$^1$-3)

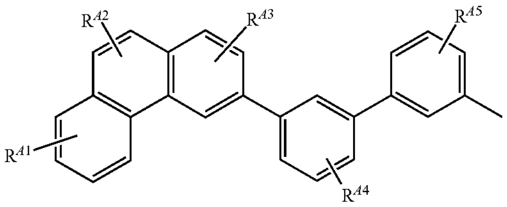

(A$^1$-4)

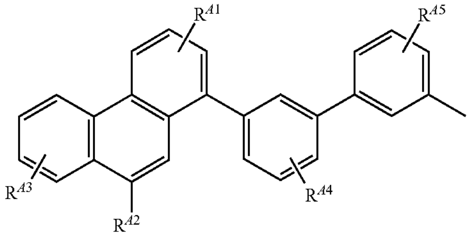

(A$^1$-5)

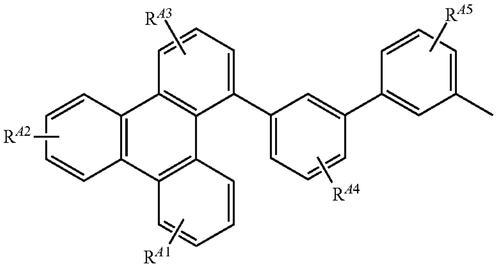

(A$^1$-6)

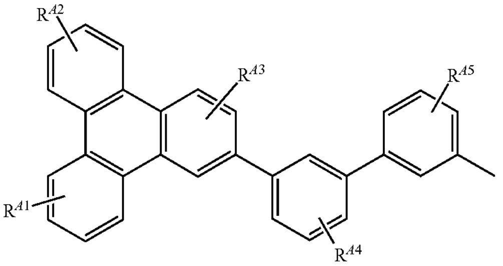

In the formulae, $R^{A1}$ to $R^{A6}$ each have 1 to 4 substituents, and the substituents are separately any one of hydrogen, an alkyl group having 1 to 6 carbon atoms, a substituted or unsubstituted monocyclic saturated hydrocarbon having 5 to 7 carbon atoms, a substituted or unsubstituted polycyclic saturated hydrocarbon having 7 to 10 carbon atoms, and a substituted or unsubstituted aryl group having 6 to 13 carbon atoms.

Further, typical examples of the heteroaryl group or the group including the aryl group and the heteroaryl group include groups represented by General Formulae (A$^1$-10) to (A$^1$-25). Note that the groups shown below are merely typical examples and A$^1$ is not limited to these examples.

(A$^1$-10)

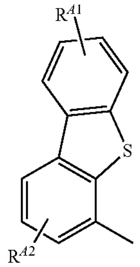

(A$^1$-11)

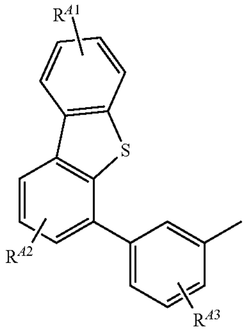

(A$^1$-12)

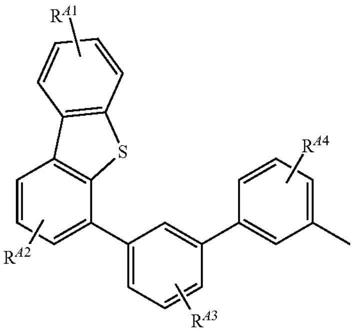

(A$^1$-13)

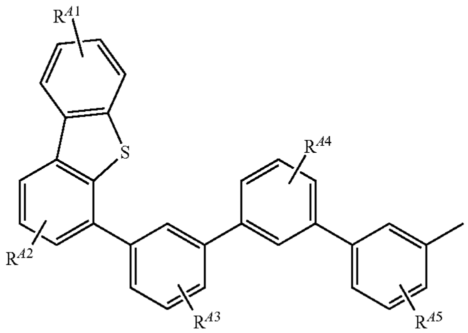

-continued
(A[1]-14)
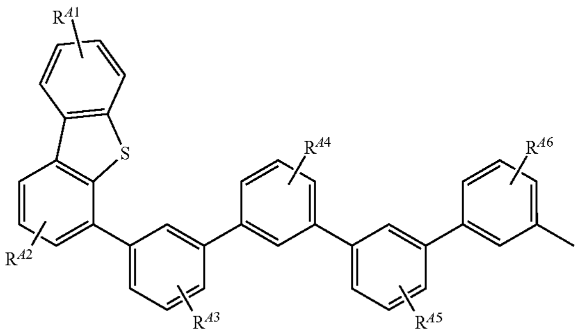
(A[1]-15)
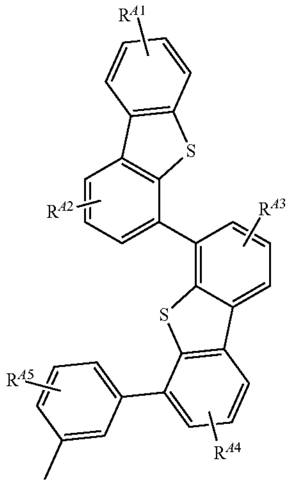
(A[1]-16)
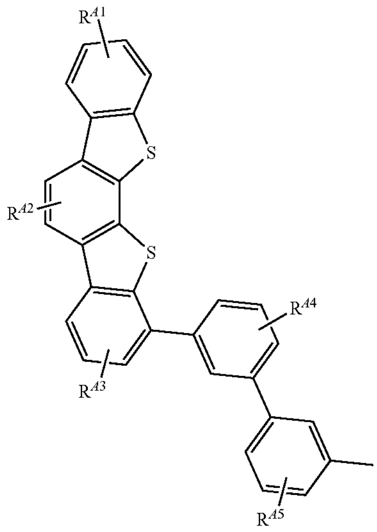
-continued
(A[1]-17)
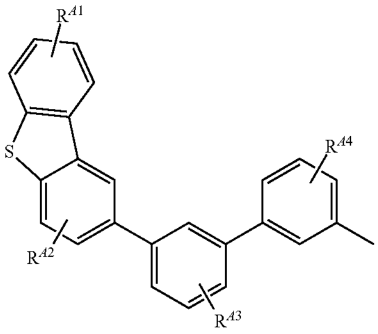
(A[1]-18)
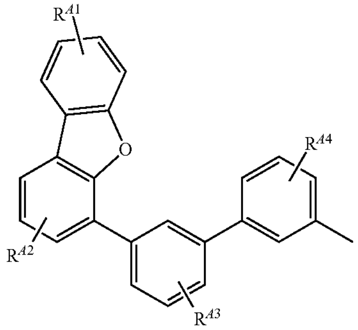
(A[1]-19)
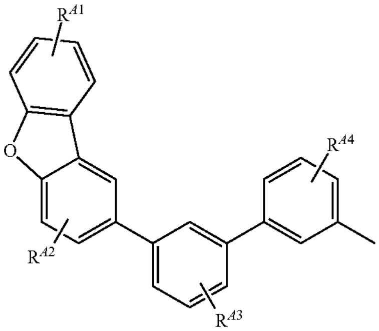
(A[1]-20)
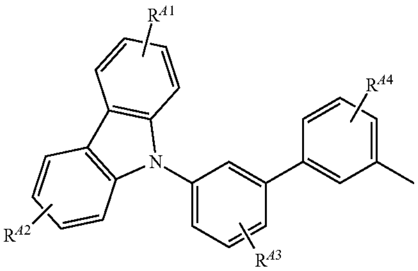

-continued ($A^1$-21)

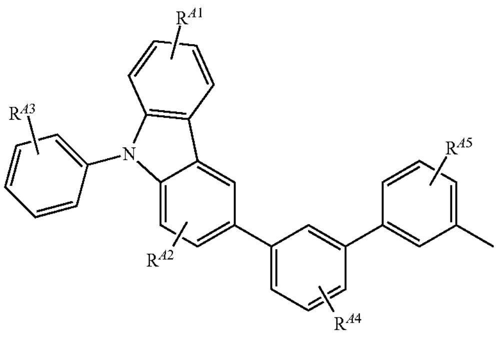

($A^1$-22)

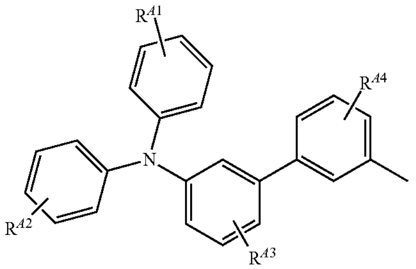

($A^1$-23)

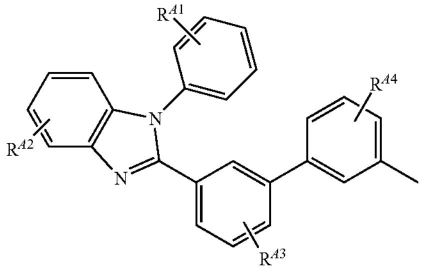

($A^1$-24)

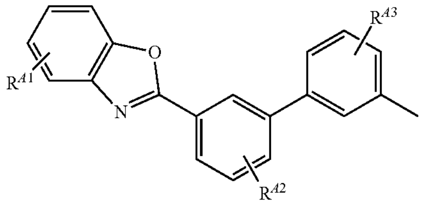

($A^1$-25)

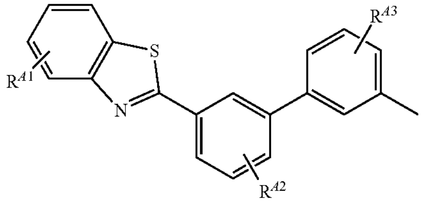

Further, $R^1$ to $R^5$ separately represent any one of hydrogen, an alkyl group having 1 to 6 carbon atoms, a substituted or unsubstituted monocyclic saturated hydrocarbon having 5 to 7 carbon atoms, a substituted or unsubstituted polycyclic saturated hydrocarbon having 7 to 10 carbon atoms, and a substituted or unsubstituted aryl group having 6 to 13 carbon atoms.

Note that specific examples of the alkyl group having 1 to 6 carbon atoms, which is represented by $R^1$ to $R^5$, include a methyl group, an ethyl group, a propyl group, an isopropyl group, a butyl group, a sec-butyl group, an isobutyl group, a tert-butyl group, a pentyl group, an isopentyl group, a sec-pentyl group, a tert-pentyl group, a neopentyl group, a hexyl group, an isohexyl group, a sec-hexyl group, a tert-hexyl group, a neohexyl group, a 3-methylpentyl group, a 2-methylpentyl group, a 2-ethylbutyl group, a 1,2-dimethylbutyl group, and a 2,3-dimethylbutyl group. Specific examples of the substituted or unsubstituted monocyclic saturated hydrocarbon having 5 to 7 carbon atoms, which is represented by $R^1$ to $R^5$, include a cyclopropyl group, a cyclobutyl group, a cyclopentyl group, a cyclohexyl group, a cyclooctyl group, a 2-methylcyclohexyl group, and a 2,6-dimethylcyclohexyl group. Specific examples of the substituted or unsubstituted polycyclic saturated hydrocarbon having 7 to 10 carbon atoms, which is represented by $R^1$ to $R^5$, include a decahydronaphthyl group and an adamantyl group. Specific examples of the substituted or unsubstituted aryl group having 6 to 13 carbon atoms, which is represented by $R^1$ to $R^5$, include a phenyl group, an o-tolyl group, a m-tolyl group, a p-tolyl group, a mesityl group, an o-biphenyl group, a m-biphenyl group, a p-biphenyl group, a 1-naphthyl group, a 2-naphthyl group, a fluorenyl group, and a 9,9-dimethylfluorenyl group.

$R^1$ to $R^5$ each may have a substituent as long as the substituent is a group that does not significantly change the characteristics of the compound, such as an alkyl group having 1 to 3 carbon atoms.

A further preferable example of benzofuropyrimidine described in this embodiment can be represented by General Formula (G2).

(G2)

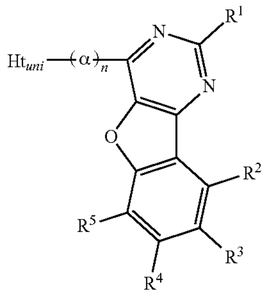

$R^1$ to $R^5$ in General Formula (G2) are similar to those in General Formula (G1) and thus redundant description is omitted. Refer to the description of $R^1$ to $R^5$ in General Formula (G1).

In General formula (G2), α represents a substituted or unsubstituted phenylene group, and n is an integer from 0 to 4. α may have a substituent as long as the substituent is a group that does not significantly change the characteristics of the compound, such as an alkyl group having 1 to 3 carbon atoms.

To inhibit interaction between $Ht_{uni}$ and the benzofuropyrimidine skeleton and keep a high triplet excitation level ($T_1$ level), n is preferably 1 or more; to improve a thermophysical property and stability of a molecule, n is preferably 2. Further, when n is 2, the divalent group denoted by α and n is preferably a 1,1'-biphenyl-3,3'-diyl group.

In General Formula (G2), $Ht_{uni}$ represents a hole-transport skeleton. To keep a high triplet excitation level ($T_1$ level), $Ht_{uni}$ is preferably a substituted or unsubstituted dibenzothiophenyl group, a substituted or unsubstituted dibenzofuranyl group, or a substituted or unsubstituted carbazolyl group. The group represented by $Ht_{uni}$ may have a substituent as long as the substituent is a group that does not significantly change the characteristics of the compound, such as an alkyl group having 1 to 3 carbon atoms.

Among specific examples of $Ht_{uni}$, groups represented by General Formulae (Ht-1) to (Ht-6) are preferable because they can be easily synthesized. Needless to say, $Ht_{uni}$ is not limited to the examples shown below.

(Ht-1)

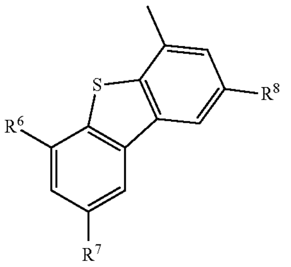

(Ht-2)

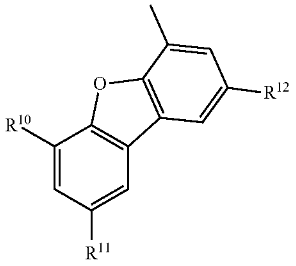

(Ht-3)

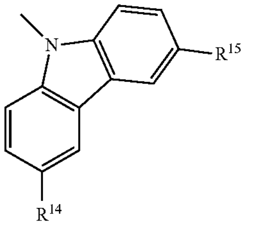

(Ht-4)

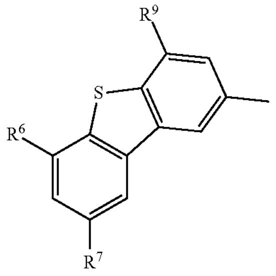

(Ht-5)

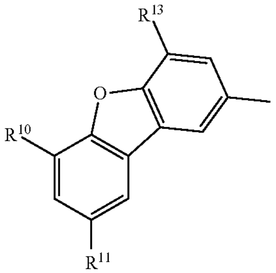

-continued (Ht-6)

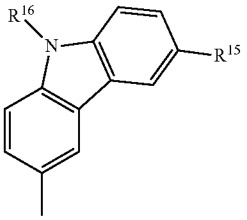

$R^6$ to $R^{15}$ separately represent any one of hydrogen, an alkyl group having 1 to 6 carbon atoms, and a substituted or unsubstituted phenyl group. In addition, $R^{16}$ represents any one of an alkyl group having 1 to 6 carbon atoms and a substituted or unsubstituted phenyl group. The groups represented by $R^6$ to $R^{15}$ and $R^{16}$ each may have a substituent as long as the substituent is a group that does not significantly change the characteristics of the compound, such as an alkyl group having 1 to 3 carbon atoms.

The compound of one embodiment of the present invention in which $Ht_{uni}$ is any one of the groups represented by General Formulae (Ht-1) to (Ht-6) is preferable because the compound has a high triplet excitation level ($T_1$ level) and a hole-transport property. The groups represented by General Formulae (Ht-1) to (Ht-6) each serve as an electron donor site when combined with a benzofuropyrimidine skeleton (benzofuropyrimidine serves as an electron acceptor site). Therefore, in view of an electric charge transport property of a film, the compound of one embodiment of the present invention in which $Ht_{uni}$ is any one of the groups represented by General Formulae (Ht-1) to (Ht-6) is preferably used as a material of a light-emitting element because the compound has a high conductive property in its bulk and a high carrier-injection property at its interface, which enables low-voltage driving.

It is preferable that $R^6$ to $R^{15}$ in the groups represented by General Formulae (Ht-1) to (Ht-6) be each hydrogen, in which case widely available raw materials can be used and the compound can be easily synthesized.

To obtain similar advantages, both $R^2$ and $R^4$ in the compound represented by General Formula (G2) preferably represent hydrogen. It is further preferable that $R^1$ to $R^5$ each represent hydrogen.

Typical examples of the above-described compound are shown below. Note that the compounds described in this embodiment are not limited to the examples shown below.

(100)

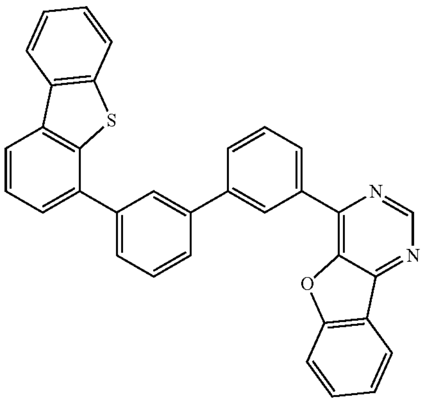

-continued
(101)
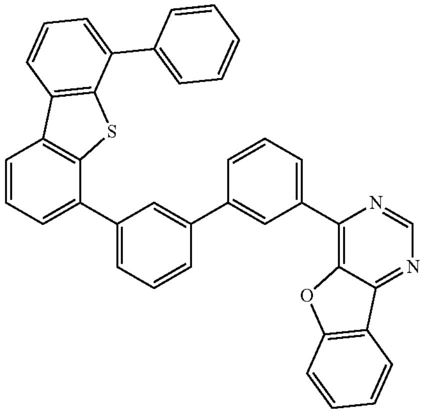
(102)
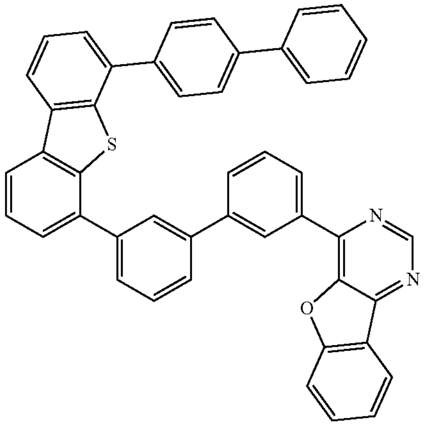
(103)
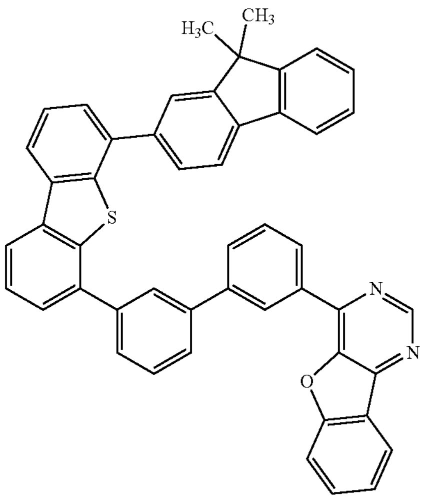
-continued
(104)
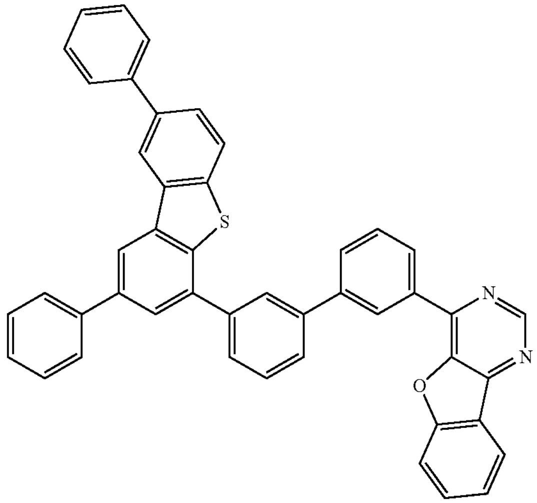
(105)
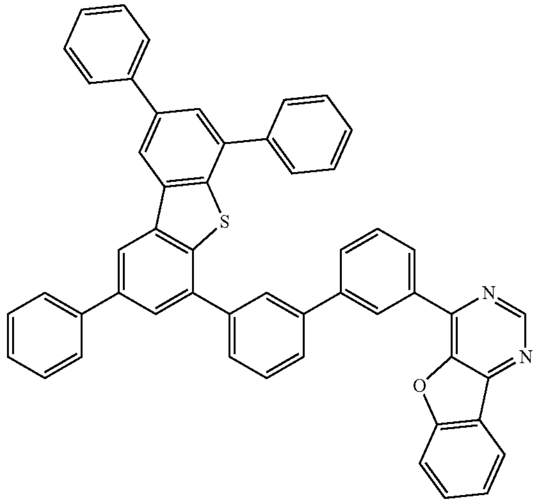
(106)
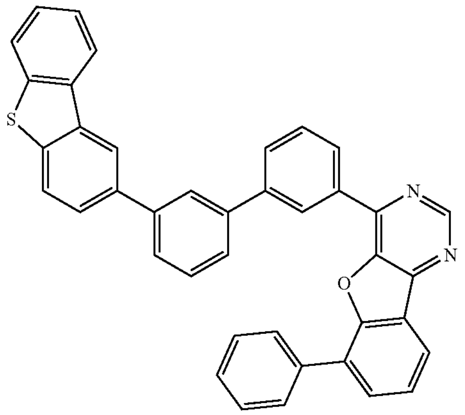

-continued
(107)
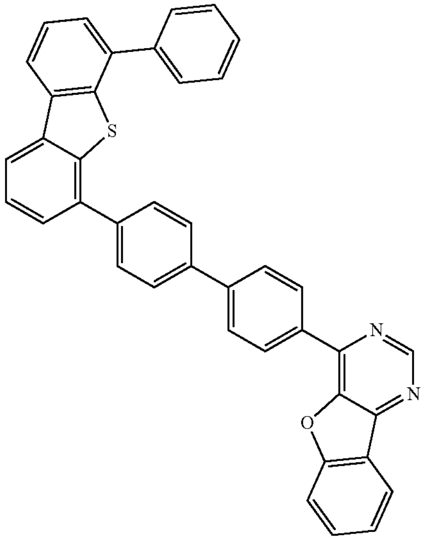
(108)
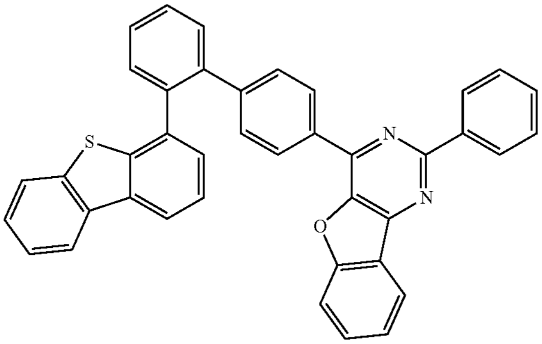
(109)
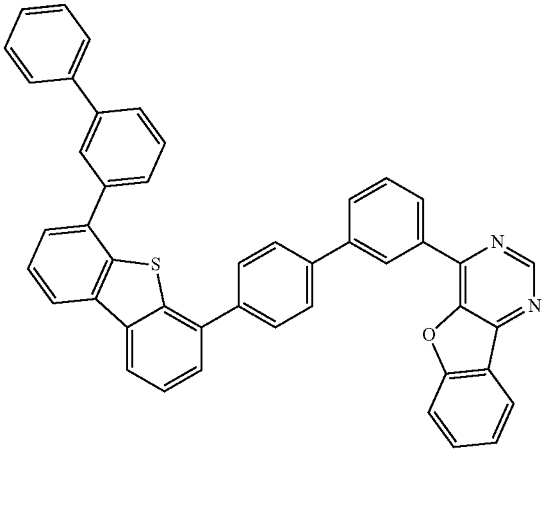
-continued
(110)
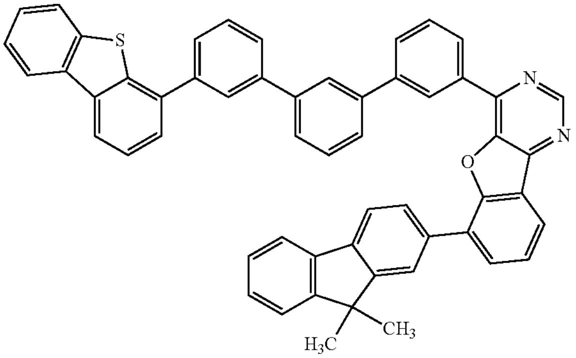
(111)
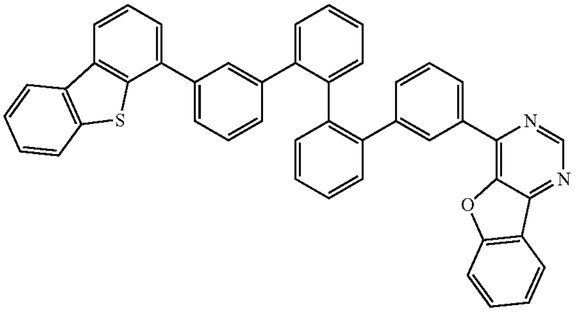
(112)
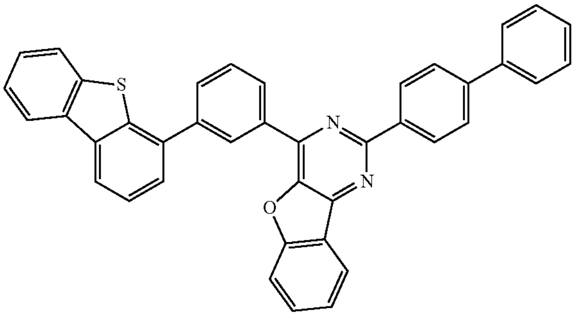
(113)
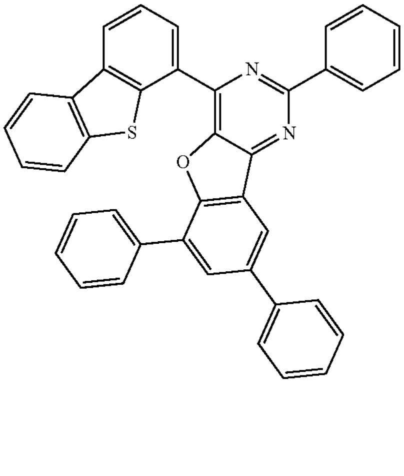

-continued
(114)
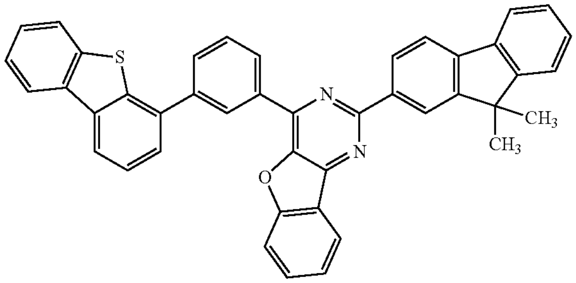
(115)
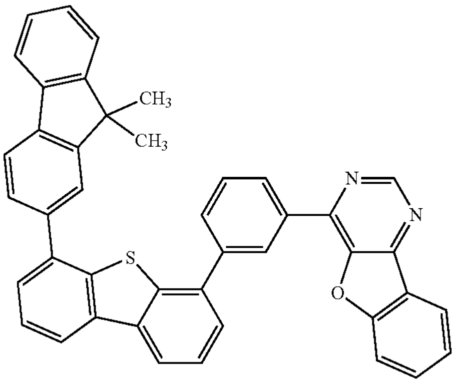
(200)
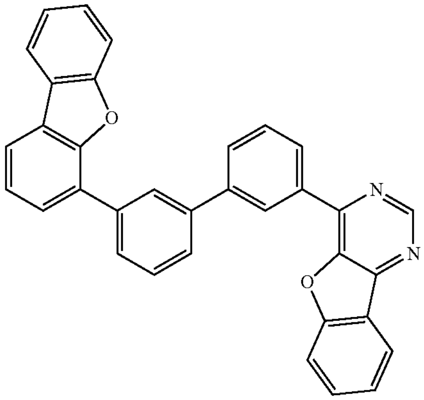
(201)
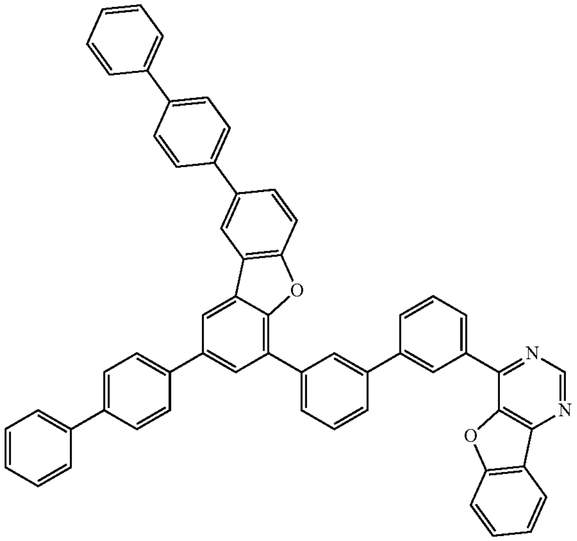
-continued
(202)
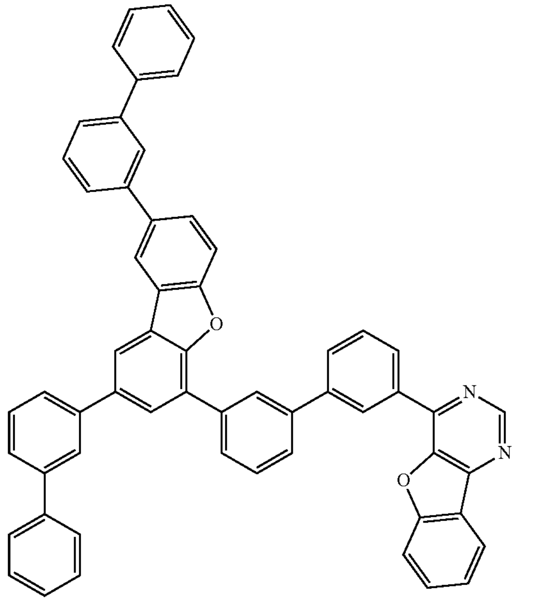
(203)
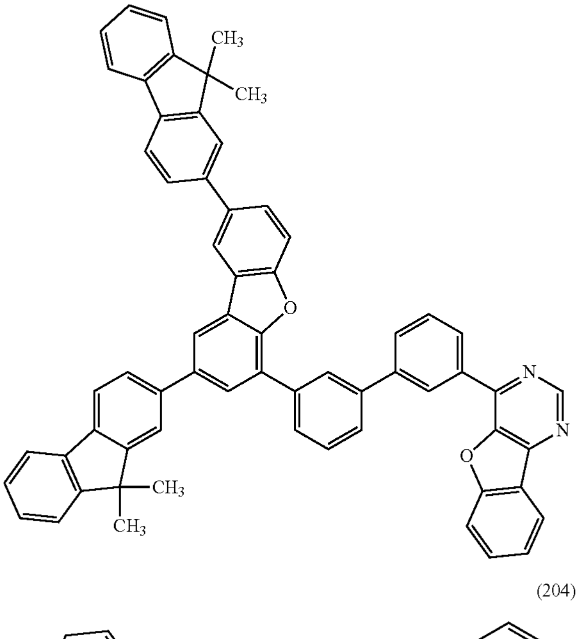
(204)
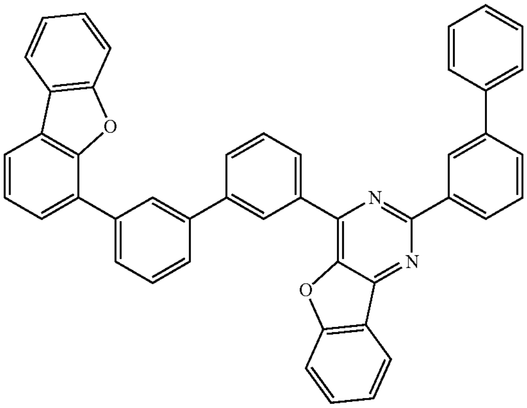

-continued (205)

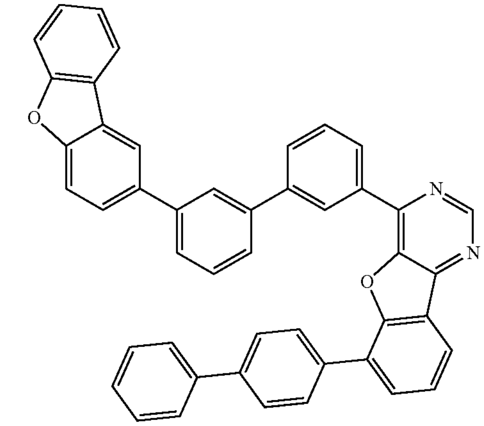

(300)

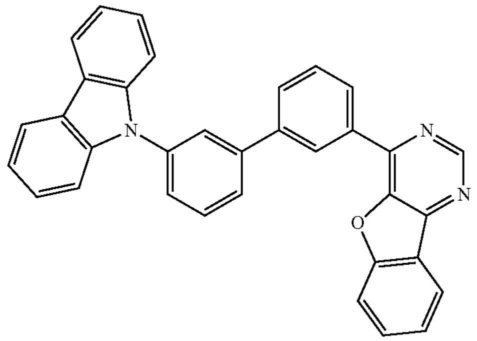

(301)

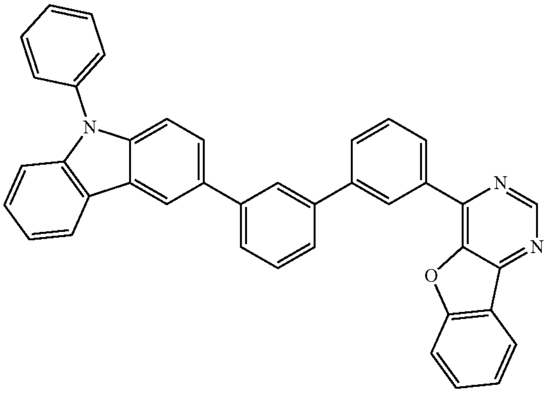

The above-described compound of one embodiment of the present invention has an excellent carrier-transport property and thus is suitable for a carrier-transport material or a host material. Owing to this, a light-emitting element driven at low voltage can also be provided. In addition, the compound of one embodiment of the present invention can have a high triplet excitation level ($T_1$ level), which makes it possible to provide a phosphorescent light-emitting element with high emission efficiency. Specifically, the compound can provide high emission efficiency even to a phosphorescent light-emitting element that has an emission peak on a shorter wavelength side than green. Moreover, the high triplet excitation level ($T_1$ level) means that the compound has a wide band gap, which allows a blue-emissive fluorescent light-emitting element to efficiently emit light.

Next, a method for synthesizing the compound represented by General Formula (G1) is described.

The compound represented by General Formula (G1) can be synthesized by a simple synthesis scheme as follows. For example, as shown in Synthesis Scheme (a), the compound can be synthesized by causing a reaction between a halide (A1) of a benzofuropyrimidine derivative and a boronic acid compound (A2) of an aryl group, a heteroaryl group, or a group including an aryl group and a heteroaryl group which is represented by $A^1$. In the formula, X represents a halogen element. B represents a boronic acid, a boronic ester, a cyclic-triolborate salt, or the like. As the cyclic-triolborate salt, a lithium salt, a potassium salt, or a sodium salt may be used.

(a)

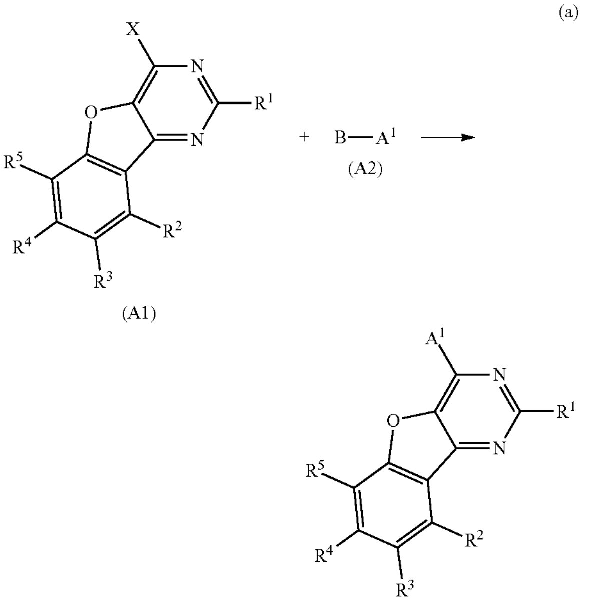

(A1) (A2) (G1)

Note that in Synthesis Scheme (a), $R^1$ to $R^5$ separately represent any one of hydrogen, an alkyl group having 1 to 6 carbon atoms, a substituted or unsubstituted monocyclic saturated hydrocarbon having 5 to 7 carbon atoms, a substituted or unsubstituted polycyclic saturated hydrocarbon having 7 to 10 carbon atoms, and a substituted or unsubstituted aryl group having 6 to 13 carbon atoms.

Note that it is also possible to cause a reaction between a boronic acid compound of a benzofuropyrimidine derivative and a halide of $A^1$.

A variety of the above compounds (A1) and (A2) can be synthesized, which means that a variety of the compound represented by General Formula (G1) can be synthesized. Thus, a feature of the compound of one embodiment of the present invention is the abundance of variations.

The above is the description of the example of a method for synthesizing the compound of one embodiment of the present invention; however, the present invention is not limited thereto and any other synthesis method may be employed.

A compound that includes the compound described in this embodiment as a partial structure is also one embodiment of the present invention. As an example of such a compound, an organometallic complex that includes the above structure as a ligand can be given.

That is, the compound includes the compound with the benzofuropyrimidine skeleton as a partial structure, and the partial structure is represented by General Formula (G1).

(G1)

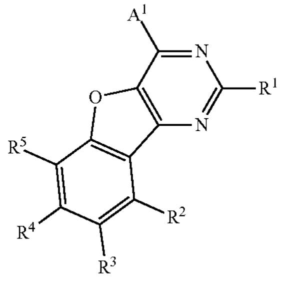

In General Formula (G1), $R^1$ to $R^5$ are similar to those described above and thus redundant description is omitted.

In General Formula (G1), $A^1$ represents any one of a substituted or unsubstituted aryl group having 6 to 100 carbon atoms, a substituted or unsubstituted heteroaryl group, and a group having 6 to 100 carbon atoms and including a substituted or unsubstituted aryl group and a substituted or unsubstituted heteroaryl group. Specific examples of a group that can be used as $A^1$ are already described above and thus redundant description is omitted.

Note that when the above compound including the partial structure represented by General Formula (G1) is an organometallic complex and its central metal is iridium or platinum, this compound can also be used as a phosphorescent substance.

EMBODIMENT 2

This embodiment will show an example in which the compound represented by General Formula (G1) in Embodiment 1 is used for an active layer of a vertical transistor (static induction transistor (SIT)), which is a kind of an organic semiconductor element.

(G1)

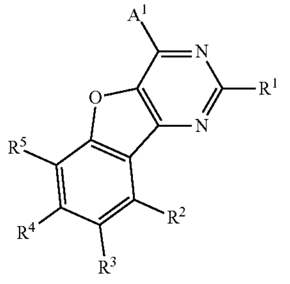

Figure 2:
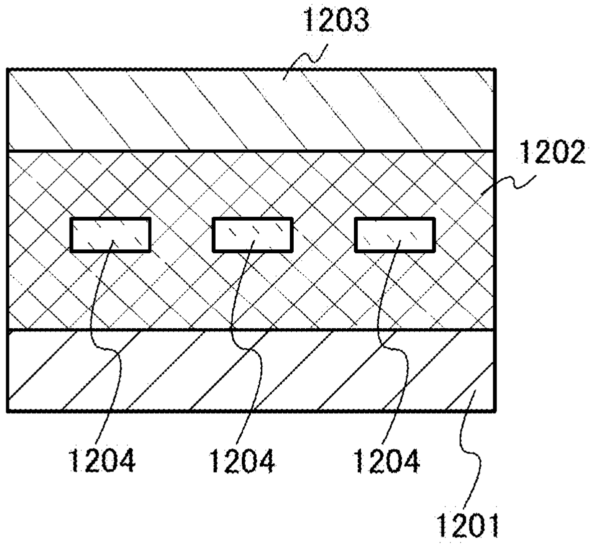
FIG. 2 is a schematic diagram of an organic semiconductor element.

The element has a structure in which a thin-film active layer 1202 containing the compound represented by General Formula (G1) is provided between a source electrode 1201 and a drain electrode 1203, and gate electrodes 1204 are embedded in the active layer 1202, as illustrated in FIG. 2. The gate electrodes 1204 are electrically connected to a unit for applying gate voltage, and the source electrode 1201 and the drain electrode 1203 are electrically connected to a unit for controlling the voltage between the source and the drain.

In such an element structure, when voltage is applied between the source and the drain under the condition where gate voltage is not applied, current flows (on state). Then, by application of voltage to the gate electrode in that state, a depletion layer is formed in the periphery of the gate electrode 1204, and the current ceases flowing (off state). With such a mechanism, the element operates as a transistor.

Like a light-emitting element, a vertical transistor should contain a material that can achieve both a high carrier-transport property and high film quality for an active layer; the compound represented by General Formula (G1) meets such a requirement and therefore can be suitably used.

EMBODIMENT 3

In this embodiment, one embodiment of a light-emitting element that includes a compound with a benzofuropyrimidine skeleton will be described with reference to FIG. 1A.

The light-emitting element of this embodiment has a plurality of layers between a pair of electrodes. In this embodiment, the light-emitting element includes a first electrode 101, a second electrode 102, and an EL layer 103 provided between the first electrode 101 and the second electrode 102. Note that in FIG. 1A, the first electrode 101 functions as an anode and the second electrode 102 functions as a cathode. In other words, when a voltage is applied between the first electrode 101 and the second electrode 102 such that the potential of the first electrode 101 is higher than that of the second electrode 102, light emission is obtained. Of course, a structure in which the first electrode functions as a cathode and the second electrode functions as an anode can be employed. In that case, the stacking order of layers in the EL layer is reversed from the stacking order described below. Note that in the light-emitting element of this embodiment, at least one of layers in the EL layer 103 contains the compound with a benzofuropyrimidine skeleton. Note that a layer that contains the compound with a benzofuropyrimidine skeleton is preferably a light-emitting layer or an electron-transport layer because the characteristics of the compound can be utilized and a light-emitting element having favorable characteristics can be obtained.

For the electrode functioning as an anode, any of metals, alloys, electrically conductive compounds, and mixtures thereof which have a high work function (specifically, a work function of 4.0 eV or more) or the like is preferably used. Specific examples are indium oxide-tin oxide (ITO: indium tin oxide), indium oxide-tin oxide containing silicon or silicon oxide, indium oxide-zinc oxide, indium oxide containing tungsten oxide and zinc oxide (IWZO), and the like. Films of these electrically conductive metal oxides are usually formed by sputtering but may be formed by a sol-gel method or the like. For example, indium oxide-zinc oxide can be formed by a sputtering method using a target in which zinc oxide is added to indium oxide at higher than or equal to 1 wt % and lower than or equal to 20 wt %. Moreover, indium oxide containing tungsten oxide and zinc oxide (IWZO) can be formed by a sputtering method using a target in which tungsten oxide is added to indium oxide at higher than or equal to 0.5 wt % and lower than or equal to 5 wt % and zinc oxide is added to indium oxide at higher than or equal to 0.1 wt % and lower than or equal to 1 wt %. Other examples are gold (Au), platinum (Pt), nickel (Ni), tungsten (W), chromium (Cr), molybdenum (Mo), iron (Fe), cobalt (Co), copper (Cu), palladium (Pd), a nitride of a metal material (such as titanium nitride), and the like. Graphene may also be used.

There is no particular limitation on the stacked structure of the EL layer 103. The EL layer 103 can be formed by combining a layer containing a substance having a high electron-transport property, a layer containing a substance having a high hole-transport property, a layer containing a substance having a high electron-injection property, a layer containing a substance having a high hole-injection property, a layer containing a bipolar substance (a substance having a high electron-transport and hole-transport property), a layer having a carrier-blocking property, and the like as appropriate. In this embodiment, the EL layer 103 has a structure in which a hole-injection layer 111, a hole-transport layer 112, a light-emitting layer 113, an electron-transport layer 114, and an electron-injection layer 115 are stacked in this order over the electrode functioning as an anode. Materials contained in the layers are specifically given below.

The hole-injection layer 111 is a layer containing a substance having a hole-injection property. The hole-injection layer 111 can be formed using molybdenum oxide, vanadium oxide, ruthenium oxide, tungsten oxide, manganese oxide, or the like. The hole-injection layer 111 can also be formed using a phthalocyanine-based compound such as phthalocyanine (abbreviation: $H_2Pc$) or copper phthalocyanine (abbreviation: CuPc); an aromatic amine compound such as 4,4'-bis[N-(4-diphenylaminophenyl)-N-phenylamino]biphenyl (abbreviation: DPAB) or N,N'-bis{4-[bis(3-methylphenyl)amino]phenyl}-N,N'-diphenyl-(1,1'-biphenyl)-4,4'-diamine (abbreviation: DNTPD); a high molecule compound such as poly(ethylenedioxythiophene)/poly(styrenesulfonic acid) (PEDOT/PSS), or the like.

The hole-injection layer 111 can be formed using a composite material in which a substance exhibiting an electron-accepting property (hereinafter, simply referred to as "electron-accepting substance") with respect to a substance having a hole-transport property is contained in the substance having a hole-transport property. In this specification, the composite material refers to not a material in which two materials are simply mixed but a material in the state where charge transfer between the materials can be caused by a mixture of a plurality of materials. This charge transfer includes the charge transfer that occurs only when an electric field exists.

Note that by using the composite material in which the electron-accepting substance is contained in the substance having a hole-transport property, a material used for forming the electrode can be selected regardless of the work function of the material. In other words, besides a material having a high work function, a material having a low work function can be used for the electrode functioning as an anode. Examples of the electron-accepting substance are 7,7,8,8-tetracyano-2,3,5,6-tetrafluoroquinodimethane (abbreviation: $F_4$-TCNQ), chloranil, and the like. A transition metal oxide can also be used. In particular, an oxide of a metal belonging to any of Groups 4 to 8 of the periodic table can be suitably used. Specifically, vanadium oxide, niobium oxide, tantalum oxide, chromium oxide, molybdenum oxide, tungsten oxide, manganese oxide, and rhenium oxide are preferable because of their high electron-accepting properties. Among these, molybdenum oxide is especially preferable as the electron-accepting substance because it is stable in the air, has a low hygroscopic property, and is easily handled.

As the substance with a hole-transport property used for the composite material, any of a variety of organic compounds such as an aromatic amine compound, a carbazole compound, an aromatic hydrocarbon, and a high molecular compound (such as an oligomer, a dendrimer, or a polymer) can be used. The organic compound used for the composite material is preferably an organic compound having a high hole-transport property. Specifically, a substance having a hole mobility of $1\times10^{-6}$ $cm^2/Vs$ or higher is preferably used. Note that any other substance may be used as long as the substance has a hole-transport property higher than an electron-transport property. Specific examples of the organic compound that can be used as a substance having a hole-transport property in the composite material are given below.

Examples of the aromatic amine compound are N,N-di(p-tolyl)-N,N-diphenyl-p-phenylenediamine (abbreviation: DTDPPA), 4,4'-bis[N-(4-diphenylaminophenyl)-N-phenylamino]biphenyl (abbreviation: DPAB), N,N'-bis{4-[bis(3-methylphenyl)amino]phenyl}-N,N'-diphenyl-(1,1'-biphenyl)-4,4'-diamine (abbreviation: DNTPD), 1,3,5-tris[N-(4-diphenylaminophenyl)-N-phenylamino]benzene (abbreviation: DPA3B), and the like.

Specific examples of the carbazole compound that can be used for the composite material are 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), and the like.

Other examples of the carbazole compound that can be used for the composite material are 4,4'-di(N-carbazolyl)biphenyl (abbreviation: CBP), 1,3,5-tris[4-(N-carbazolyl)phenyl]benzene (abbreviation: TCPB), 9-[4-(10-phenyl-9-anthryl)phenyl]-9H-carbazole (abbreviation: CzPA), 1,4-bis[4-(N-carbazolyl)phenyl]-2,3,5,6-tetraphenylbenzene, and the like.

Examples of the aromatic hydrocarbon that can be used for the composite material are 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 2-tert-butyl-9,10-bis[2-(1-naphthyl)phenyl]anthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, and the like. Other examples are pentacene, coronene, and the like. The aromatic hydrocarbon having a hole mobility of $1\times10^{-6}$ $cm^2/Vs$ or more and having 14 to 42 carbon atoms is particularly preferable.

The aromatic hydrocarbon that can be used for the composite material may have a vinyl skeleton. Examples of the aromatic hydrocarbon having a vinyl group are 4,4'-bis(2,2-diphenylvinyl)biphenyl (abbreviation: DPVBi), 9,10-bis[4-(2,2-diphenylvinyl)phenyl]anthracene (abbreviation: DPVPA), and the like.

Other examples are high molecular compounds such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide](abbreviation: PTPDMA), and poly[N,N-bis(4-butylphenyl)-N,N-bis(phenyl)benzidine] (abbreviation: poly-TPD).

The hole-transport layer 112 is a layer containing a substance having a hole-transport property. As the substance having a hole-transport property, those given above as the substances having hole-transport properties, which can be used for the above composite material, can be used. Note that detailed description is omitted to avoid repetition. Refer to the description of the composite material. Note that the compound with a benzofuropyrimidine skeleton that is described in Embodiment 1 may be contained in the hole-transport layer.

The light-emitting layer 113 is a layer containing a light-emitting substance. The light-emitting layer 113 may be formed using a film containing only a light-emitting substance or a film in which a light-emitting substance is dispersed in a host material.

There is no particular limitation on a material that can be used as the light-emitting substance in the light-emitting layer 113, and light emitted from the material may be either fluorescence or phosphorescence. Examples of the above light-emitting substance are fluorescent substances and phosphorescent substances. Examples of the fluorescent substance are N,N'-bis[4-(9-phenyl-9H-fluoren-9-yl)phenyl]-N,N'-diphenylpyrene-1,6-diamine (abbreviation: 1,6FLPAPrn), N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), perylene, 2,5,8,11-tetra(tert-butyl)perylene (abbreviation: TBP), 4-(10-phenyl-9-anthryl)-4'-(9-phenyl-9H-carbazol-3-yl)triphenylamine (abbreviation: PCBAPA), N,N''-(2-tert-butylanthracene-9,10-diyldi-4,1-phenylene)bis[N,N',N'-triphenyl-1,4-phenylenediamine](abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N',N'-triphenyl-1,4-phenylenediamine (abbreviation: 2DPAPPA), N,N,N',N',N'',N'',N''',N'''-octaphenyldibenzo[g,p]chrysene-2,7,10,15-tetraamine (abbreviation: DBC1), coumarin 30, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), coumarin 545T, N,N'-diphenylquinacridone (abbreviation: DPQd), rubrene, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), 2-{2-isopropyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTI), 2-{2-tert-butyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTB), 2-(2,6-bis{2-[4-(dimethylamino)phenyl]ethenyl}-4H-pyran-4-ylidene)propanedinitrile (abbreviation: BisDCM), 2-{2,6-bis[2-(8-methoxy-1,1,7,7-tetramethyl-2,3,6,7-tetrahydro-1H,5H-benzo[i]quinolizin-9-yl)ethenyl]-4H-pyran-4-ylidene}propanedinitrile (abbreviation: BisDCJTM), N,N'-bis[4-(9-phenyl-9H-fluoren-9-yl)phenyl]-N,N'-diphenylpyrene-1,6-diamine (abbreviation: 1,6FLPAPrn), and the like. Examples of blue-emissive phosphorescent substances include an organometallic iridium complex having a 4H-triazole skeleton, such as tris{2-[5-(2-methylphenyl)-4-(2,6-dimethylphenyl)-4H-1,2,4-triazol-3-yl-κN2]phenyl-κC}iridium(III) (abbreviation: $[Ir(mpptz\text{-}dmp)_3]$), tris(5-methyl-3,4-diphenyl-4H-1,2,4-triazolato)iridium(III) (abbreviation: $[Ir(Mptz)_3]$), or tris[4-(3-biphenyl)-5-isopropyl-3-phenyl-4H-1,2,4-triazolato]iridium(III) (abbreviation: $[Ir(iPrptz\text{-}3b)_3]$); an organometallic iridium complex having a 1H-triazole skeleton, such as tris[3-methyl-1-(2-methylphenyl)-5-phenyl-1H-1,2,4-triazolato]iridium(III) (abbreviation: $[Ir(Mptz1\text{-}mp)_3]$) or tris(1-methyl-5-phenyl-3-propyl-1H-1,2,4-triazolato)iridium(III) (abbreviation: $[Ir(Prptz1\text{-}Me)_3]$); an organometallic iridium complex having an imidazole skeleton, such as fac-tris[1-(2,6-diisopropylphenyl)-2-phenyl-1H-imidazole]iridium(III) (abbreviation: $[Ir(iPrpmi)_3]$), or tris[3-(2,6-dimethylphenyl)-7-methylimidazo[1,2-f]phenanthridinato]iridium(III) (abbreviation: $Ir(dmpimpt\text{-}Me)_3$); and an organometallic iridium complex in which a phenylpyridine derivative having an electron-withdrawing group is a ligand, such as bis[2-(4',6'-difluorophenyl)pyridinato-N,$C^{2'}$]iridium(III) tetrakis(1-pyrazolyl)borate (abbreviation: FIr6), bis[2-(4',6'-difluorophenyl)pyridinato-N,$C^{2'}$]iridium(III) picolinate (abbreviation: FIrpic), bis{2-[3',5'-bis(trifluoromethyl)phenyl]pyridinato-N,$C^{2'}$}iridium(III) picolinate (abbreviation: $[Ir(CF_3ppy)_2(pic)]$), or bis[2-(4',6'-difluorophenyl)pyridinato-N,$C^{2'}$]iridium(III) acetylacetonate (abbreviation: FIr(acac)). Note that an organometallic iridium complex having a 4H-triazole skeleton has excellent reliability and emission efficiency and thus is especially preferable. Examples of green-emissive phosphorescent substances include an organometallic iridium complex having a pyrimidine skeleton, such as tris(4-methyl-6-phenylpyrimidinato)iridium(III) (abbreviation: $[Ir(mppm)_3]$), tris(4-t-butyl-6-phenylpyrimidinato)iridium(III) (abbreviation: $[Ir(tBuppm)_3]$), (acetylacetonato)bis(6-methyl-4-phenylpyrimidinato)iridium(III) (abbreviation: $[Ir(mppm)_2(acac)]$), (acetylacetonato)bis(6-tert-butyl-4-phenylpyrimidinato)iridium(III) (abbreviation: $[Ir(tBuppm)_2(acac)]$), (acetylacetonato)bis[6-(2-norbornyl)-4-phenylpyrimidinato]iridium(III) (abbreviation: $[Ir(nbppm)_2(acac)]$), (acetylacetonato)bis[5-methyl-6-(2-methylphenyl)-4-phenylpyrimidinato]iridium(III) (abbreviation: $[Ir(mpmppm)_2(acac)]$), or (acetylacetonato)bis(4,6-diphenylpyrimidinato)iridium(III) (abbreviation: $[Ir(dppm)_2(acac)]$); an organometallic iridium complex having a pyrazine skeleton, such as (acetylacetonato)bis(3,5-dimethyl-2-phenylpyrazinato)iridium(III) (abbreviation: $[Ir(mppr\text{-}Me)_2(acac)]$) or (acetylacetonato)bis(5-isopropyl-3-methyl-2-phenylpyrazinato)iridium(III) (abbreviation: $[Ir(mppr\text{-}iPr)_2(acac)]$); an organometallic iridium complex having a pyridine skeleton, such as tris(2-phenylpyridinato-N,$C^{2'}$)iridium(III) (abbreviation: $[Ir(ppy)_3]$), bis(2-phenylpyridinato-N,$C^{2'}$)iridium(III) acetylacetonate (abbreviation: $[Ir(ppy)_2(acac)]$), bis(benzo[h]quinolinato)iridium(III) acetylacetonate (abbreviation: $[Ir(bzq)_2(acac)]$), tris(benzo[h]quinolinato)iridium(III) (abbreviation: $[Ir(bzq)_3]$), tris(2-phenylquinolinato-N,$C^{2'}$)iridium(III) (abbreviation: $[Ir(pq)_3]$), or bis(2-phenylquinolinato-N,$C^{2'}$)iridium(III) acetylacetonate (abbreviation: $[Ir(pq)_2(acac)]$); and a rare earth metal complex such as tris(acetylacetonato)(monophenanthroline)terbium(III) (abbreviation: $Tb(acac)_3(Phen)$). Note that an organometallic iridium complex having a pyrimidine skeleton has distinctively high reliability and emission efficiency and thus is especially preferable. Examples of red-emissive phosphorescent substances include an organometallic iridium complex having a pyrimidine skeleton, such as (diisobutyrylmethanato)bis[4,6-bis(3-methylphenyl)pyrimidinato]iridium(III) (abbreviation: [Ir(5mdppm)$_2$(dibm)]), bis[4,6-bis(3-methylphenyl)pyrimidinato](dipivaloylmethanato)iridium(III) (abbreviation: [Ir(5mdppm)$_2$(dpm)]), or bis[4,6-di(naphthalen-1-yl)pyrimidinato](dipivaloylmethanato)iridium(III) (abbreviation: [Ir(d1npm)$_2$(dpm)]); an organometallic iridium complex having a pyrazine skeleton, such as (acetylacetonato)bis(2,3,5-triphenylpyrazinato)iridium(III) (abbreviation: [Ir(tppr)$_2$(acac)]), bis(2,3,5-triphenylpyrazinato)(dipivaloylmethanato)iridium(III) (abbreviation: [Ir(tppr)$_2$(dpm)]), or (acetylacetonato)bis[2,3-bis(4-fluorophenyl)quinoxalinato]iridium(III) (abbreviation: [Ir(Fdpq)$_2$(acac)]); an organometallic iridium complex having a pyridine skeleton, such as tris(1-phenylisoquinolinato-N,C$^{2'}$)iridium(III) (abbreviation: [Ir(piq)$_3$]) or bis(1-phenylisoquinolinato-N,C$^{2'}$)iridium(III)acetylacetonate (abbreviation: [Ir(piq)$_2$(acac)]); a platinum complex such as 2,3,7,8,12,13,17,18-octaethyl-21H,23H-porphyrin platinum(II) (abbreviation: PtOEP); and a rare earth metal complex such as tris(1,3-diphenyl-1,3-propanedionato)(monophenanthroline)europium(III) (abbreviation: [Eu(DBM)$_3$(Phen)]) or tris[1-(2-thenoyl)-3,3,3-trifluoroacetonato](monophenanthroline)europium(III) (abbreviation: [Eu(TTA)$_3$(Phen)]). Note that an organometallic iridium complex having a pyrimidine skeleton has distinctively high reliability and emission efficiency and thus is especially preferable. Further, because an organometallic iridium complex having a pyrazine skeleton can provide red light emission with favorable chromaticity, the use of the organometallic iridium complex in a white light-emitting element improves a color rendering property of the white light-emitting element. Note that a compound with a benzofuropyrimidine skeleton exhibits light in blue to ultraviolet regions, and thus can be used as a light-emitting material. It is also possible to use a compound with a benzofuropyrimidine skeleton.

The material that can be used as the light-emitting substance may be selected from various substances as well as from the substances given above.

As a host material in which the light-emitting substance is dispersed, the compound with a benzofuropyrimidine skeleton is preferably used.

Since the compound with a benzofuropyrimidine skeleton has a wide band gap and a high triplet excitation level (T$_1$ level), the compound can be suitably used as a host material in which a light-emitting substance emitting high-energy light is dispersed, such as a fluorescent substance emitting blue or a phosphorescent substance emitting a color between green and blue. Needless to say, the compound can also be used as a host material in which a fluorescent substance emitting fluorescence having a wavelength longer than the blue light wavelength or a phosphorescent substance emitting phosphorescence having a wavelength longer than the green light wavelength is dispersed. The carrier-transport property (specifically, the electron-transport property) of the compound is high; accordingly, a light-emitting element with low driving voltage can be provided.

In addition, it is effective to use the compound with the benzofuropyrimidine skeleton as a material of a carrier-transport layer (preferably an electron-transport layer) adjacent to a light-emitting layer. Since the compound has a wide band gap or a high triplet excitation level (T$_1$ level), even when the light-emitting substance is a material emitting high-energy light, such as a material emitting blue fluorescence or a material emitting green to blue phosphorescence, the energy of carriers that have recombined in a host material can be effectively transferred to the light-emitting substance. Thus, a light-emitting element having high emission efficiency can be fabricated. Note that in the case where the compound is used as a host material or a material of a carrier-transport layer, the light-emitting material is preferably, but not limited to, a substance having a narrower band gap than the compound or a substance having a lower singlet excitation level (S$_1$ level) or a lower triplet excitation level (T$_1$ level) than the compound.

When the above compound with a benzofuropyrimidine skeleton is not used as the host material, the following materials can be alternatively used.

The following are examples of materials having an electron-transport property: a metal complex such as bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), or bis[2-(2-benzothiazolyl)phenolato]zinc(II) (abbreviation: ZnBTZ); a heterocyclic compound having a polyazole skeleton such as 2-(4-biphenylyl)-5-(4-tert-butylphenyl)-1,3,4-oxadiazole (abbreviation: PBD), 3-(4-biphenylyl)-4-phenyl-5-(4-tert-butylphenyl)-1,2,4-triazole (abbreviation: TAZ), 1,3-bis[5-(p-tert-butylphenyl)-1,3,4-oxadiazol-2-yl]benzene (abbreviation: OXD-7), 9-[4-(5-phenyl-1,3,4-oxadiazol-2-yl)phenyl]-9H-carbazole (abbreviation: CO11), 2,2',2"-(1,3,5-benzenetriyl)tris(1-phenyl-1H-benzimidazole) (abbreviation: TPBI), or 2-[3-(dibenzothiophen-4-yl)phenyl]-1-phenyl-1H-benzimidazole (abbreviation: mDBTBIm-II); a heterocyclic compound having a diazine skeleton such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[3'-(9H-carbazol-9-yl)biphenyl-3-yl]dibenzo[f,h]quinoxaline (abbreviation: 2mCzBPDBq), 4,6-bis[3-(phenanthren-9-yl)phenyl]pyrimidine (abbreviation: 4,6mPnP2Pm), or 4,6-bis[3-(4-dibenzothienyl)phenyl]pyrimidine (abbreviation: 4,6mDBTP2Pm-II); and a heterocyclic compound having a pyridine skeleton such as 3,5-bis[3-(9H-carbazol-9-yl)phenyl]pyridine (abbreviation: 35DCzPPy) or 1,3,5-tri[3-(3-pyridyl)phenyl]benzene (abbreviation: TmPyPB). Among the above materials, a heterocyclic compound having a diazine skeleton and a heterocyclic compound having a pyridine skeleton have high reliability and are thus preferable. Specifically, a heterocyclic compound having a diazine (pyrimidine or pyrazine) skeleton has a high electron-transport property to contribute to a reduction in driving voltage. Note that the above compound with a benzofuropyrimidine skeleton has a relatively high electron-transport property, and is classified as a material having an electron-transport property.

The following are examples of materials which have a hole-transport property and can be used as the host material: a compound having an aromatic amine skeleton such as 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), 4-phenyl-4'-(9-phenyl-9H-carbazol-3-yl)triphenylamine (abbreviation: PCBA1BP), 4,4'-diphenyl-4"-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4"-(9-phenyl-9H-carbazol-3-yl)triphenylamine (abbreviation: PCBNBB), 9,9-dimethyl-N-phenyl-N-[4-(9-phenyl-9H-carbazol-3-yl)phenyl]fluoren-2-amine (abbreviation: PCBAF), or N-phenyl-N-[4-(9-phenyl-9H-carbazol-3-yl)phenyl]spiro-9,9'-bifluoren-2-amine (abbreviation: PCBASF); a compound having a carbazole skeleton such as 1,3-bis(N-carbazolyl)benzene (abbreviation: mCP), 4,4'-di(N-carbazolyl)biphenyl (abbreviation: CBP), 3,6-bis(3,5-diphenylphenyl)-9-phenylcarbazole (abbreviation: CzTP), or 3,3'-bis(9-phenyl-9H-carbazole) (abbreviation: PCCP); a compound having a thiophene skeleton such as 4,4',4"-(benzene-1,3,5-triyl)tri(dibenzothiophene) (abbreviation: DBT3P-II), 2,8-diphenyl-4-[4-(9-phenyl-9H-fluoren-9-yl)phenyl]dibenzothiophene (abbreviation: DBTFLP-III), or 4-[4-(9-phenyl-9H-fluoren-9-yl)phenyl]-6-phenyldibenzothiophene (abbreviation: DBTFLP-IV); and a compound having a furan skeleton such as 4,4',4"-(benzene-1,3,5-triyl)tri(dibenzofuran) (abbreviation: DBF3P-II) or 4-{3-[3-(9-phenyl-9H-fluoren-9-yl)phenyl]phenyl}dibenzofuran (abbreviation: mmDBFFLBi-II). Among the above materials, a compound having an aromatic amine skeleton and a compound having a carbazole skeleton are preferable because these compounds are highly reliable and have high hole-transport properties to contribute to a reduction in driving voltage.

Note that when the light-emitting substance is a phosphorescent substance, a substance having a higher triplet excitation level ($T_1$ level) than the phosphorescent substance is preferably selected as the host material, and when the light-emitting substance is a fluorescent substance, a substance having a wider band gap than the fluorescent substance is preferably selected as the host material. The light-emitting layer may contain a third substance in addition to the host material and the phosphorescent substance.

Here, to achieve high emission efficiency of a light-emitting element that uses a phosphorescent substance, energy transfer between the host material and the phosphorescent substance will be considered. Carrier recombination occurs in both the host material and the phosphorescent substance; thus, efficient energy transfer from the host material to the phosphorescent substance is necessary to increase emission efficiency.

As mechanisms of the energy transfer from the host material to the phosphorescent substance, two mechanisms have been proposed: one is Dexter mechanism, and the other is Förster mechanism. Each mechanism is described below. Here, a molecule providing excitation energy is referred to as a host molecule, while a molecule receiving the excitation energy is referred to as a guest molecule.

<<Förster Mechanism (Dipole-Dipole Interaction)>>

Förster mechanism (also referred to as Förster resonance energy transfer) does not require direct contact between molecules for energy transfer. Through a resonant phenomenon of dipolar oscillation between a host molecule and a guest molecule, energy transfer occurs. By the resonant phenomenon of dipolar oscillation, the host molecule provides energy to the guest molecule, and thus, the host molecule returns to a ground state and the guest molecule reaches an excited state. The rate constant $k_{h^* \rightarrow g}$ of Forster mechanism is expressed by Formula (1).

[Formula 1]

$$k_{h^* \rightarrow g} = \frac{9000 c^4 K^2 \phi \ln 10}{128 \pi^5 n^4 N \tau R^6} \int \frac{f_h'(v) \varepsilon_g(v)}{v^4} dv \qquad (1)$$

In Formula (1), v denotes a frequency, $f'_h(v)$ denotes a normalized emission spectrum of a host molecule (a fluorescence spectrum in energy transfer from a singlet excited state, and a phosphorescence spectrum in energy transfer from a triplet excited state), $\varepsilon_g(v)$ denotes a molar absorption coefficient of a guest molecule, N denotes Avogadro's number, n denotes a refractive index of a medium, R denotes an intermolecular distance between the host molecule and the guest molecule, $\tau$ denotes a measured lifetime of an excited state (fluorescence lifetime or phosphorescence lifetime), c denotes the speed of light, $\phi$ denotes a luminescence quantum yield (a fluorescence quantum yield in energy transfer from a singlet excited state, and a phosphorescence quantum yield in energy transfer from a triplet excited state), and $K^2$ denotes a coefficient (0 to 4) of orientation of a transition dipole moment between the host molecule and the guest molecule. Note that $K^2$'⅔ in random orientation.

<<Dexter Mechanism (Electron Exchange Interaction)>>

In Dexter mechanism (also referred to as Dexter electron transfer), a host molecule and a guest molecule are close to a contact effective range where their orbitals can overlap, and the host molecule in an excited state and the guest molecule in a ground state exchange their electrons, which leads to energy transfer. The rate constant $k_{h^* \rightarrow g}$ of Dexter mechanism is expressed by Formula (2).

[Formula 2]

$$k_{h^* \rightarrow g} = \left(\frac{2\pi}{h}\right) K^2 \exp\left(-\frac{2R}{L}\right) \int f_h'(v) \varepsilon_g'(v) dv \qquad (2)$$

In Formula (2), h denotes a Planck constant, K denotes a constant having an energy dimension, v denotes a frequency, $f'_h(v)$ denotes a normalized emission spectrum of a host molecule (a fluorescence spectrum in energy transfer from a singlet excited state, and a phosphorescence spectrum in energy transfer from a triplet excited state), $\varepsilon'_g(v)$ denotes a normalized absorption spectrum of a guest molecule, L denotes an effective molecular radius, and R denotes an intermolecular distance between the host molecule and the guest molecule.

Here, the efficiency of energy transfer from the host molecule to the guest molecule (energy transfer efficiency $\Phi_{ET}$) is expressed by Formula (3). In the formula, $k_r$ denotes a rate constant of a light-emission process (fluorescence in energy transfer from a singlet excited state, and phosphorescence in energy transfer from a triplet excited state), $k_n$ denotes a rate constant of a non-light-emission process (thermal deactivation or intersystem crossing), and $\tau$ denotes a measured lifetime of an excited state.

[Formula 3]

$$\Phi_{ET} = \frac{k_{h^* \rightarrow g}}{k_r + k_n + k_{h^* \rightarrow g}} = \frac{k_{h^* \rightarrow g}}{\left(\frac{1}{\tau}\right) + k_{h^* \rightarrow g}} \qquad (3)$$

First, according to Formula (3), it is understood that the energy transfer efficiency $\Phi_{ET}$ can be increased by significantly increasing the rate constant $k_{h^* \rightarrow g}$ of energy transfer as compared with another competing rate constant $k_r + k_n$ ($=1/\tau$). Then, in order to increase the rate constant $k_{h^* \rightarrow g}$ of energy transfer, based on Formulae (1) and (2), in Forster mechanism and Dexter mechanism, it is preferable that an emission spectrum of a host molecule (a fluorescence spectrum in energy transfer from a singlet excited state, and a phosphorescence spectrum in energy transfer from a triplet excited state) has a large overlap with an absorption spectrum of a guest molecule.

Here, a longest-wavelength-side (lowest-energy-side) absorption band in the absorption spectrum of the guest molecule is important in considering the overlap between the emission spectrum of the host molecule and the absorption spectrum of the guest molecule.

In this embodiment, a phosphorescent compound is used as the guest material. In an absorption spectrum of the phosphorescent compound, an absorption band that is considered to contribute to light emission most greatly is at an absorption wavelength corresponding to direct transition from a ground state to a triplet excited state and a vicinity of the absorption wavelength, which is on the longest wavelength side. Therefore, it is considered preferable that the emission spectrum (a fluorescence spectrum and a phosphorescence spectrum) of the host material overlap with the absorption band on the longest wavelength side in the absorption spectrum of the phosphorescent compound.

For example, most organometallic complexes, especially light-emitting iridium complexes, have a broad absorption band around 500 nm to 600 nm as the absorption band on the longest wavelength side. This absorption band is mainly based on a triplet MLCT (metal to ligand charge transfer) transition. Note that it is considered that the absorption band also includes absorptions based on a triplet $\pi$-$\pi^*$ transition and a singlet MLCT transition, and that these absorptions overlap each other to form a broad absorption band on the longest wavelength side in the absorption spectrum. Therefore, when an organometallic complex (especially iridium complex) is used as the guest material, it is preferable to make the broad absorption band on the longest wavelength side have a large overlap with the emission spectrum of the host material as described above.

Here, first, energy transfer from a host material in a triplet excited state will be considered. From the above-described discussion, it is preferable that, in energy transfer from a triplet excited state, the phosphorescence spectrum of the host material and the absorption band on the longest wavelength side of the guest material have a large overlap.

However, a question here is energy transfer from the host molecule in the singlet excited state. In order to efficiently perform not only energy transfer from the triplet excited state but also energy transfer from the singlet excited state, it is clear from the above-described discussion that the host material needs to be designed such that not only its phosphorescence spectrum but also its fluorescence spectrum overlaps with the absorption band on the longest wavelength side of the guest material. In other words, unless the host material is designed so as to have its fluorescence spectrum in a position similar to that of its phosphorescence spectrum, it is not possible to achieve efficient energy transfer from the host material in both the singlet excited state and the triplet excited state.

However, in general, the $S_1$ level differs greatly from the $T_1$ level ($S_1$ level>$T_1$ level); therefore, the fluorescence emission wavelength also differs greatly from the phosphorescence emission wavelength (fluorescence emission wavelength<phosphorescence emission wavelength). For example, 4,4'-di(N-carbazolyl)biphenyl (abbreviation: CBP), which is commonly used in a light-emitting element containing a phosphorescent compound, has a phosphorescence spectrum around 500 nm and has a fluorescence spectrum around 400 nm, which are largely different by about 100 nm. This example also shows that it is extremely difficult to design a host material so as to have its fluorescence spectrum in a position similar to that of its phosphorescence spectrum.

Also, since the $S_1$ level is higher than the $T_1$ level, the $T_1$ level of a host material whose fluorescence spectrum corresponds to a wavelength close to an absorption spectrum of a guest material on the longest wavelength side is lower than the $T_1$ level of the guest material.

Thus, in the case where a phosphorescent substance is used as the light-emitting substance, it is preferable that the light-emitting layer include a third substance in addition to the host material and the light-emitting substance and a combination of the host material and the third substance form an exciplex (also referred to as an excited complex).

In that case, at the time of recombination of carriers (electrons and holes) in the light-emitting layer, the host material and the third substance form an exciplex. A fluorescence spectrum of the exciplex is on a longer wavelength side than a fluorescence spectrum of the host material alone or the third substance alone. Therefore, energy transfer from a singlet excited state can be maximized while the $T_1$ levels of the host material and the third substance are kept higher than the $T_1$ level of the guest material. In addition, the exciplex is in a state where the $T_1$ level and the $S_1$ level are close to each other; therefore, the fluorescence spectrum and the phosphorescence spectrum exist at substantially the same position. Accordingly, both the fluorescence spectrum and the phosphorescence spectrum of the exciplex can have a large overlap with an absorption corresponding to transition of the guest molecule from the singlet ground state to the triplet excited state (a broad absorption band of the guest molecule existing on the longest wavelength side in the absorption spectrum), and thus a light-emitting element having high energy transfer efficiency can be obtained.

As the third substance, the above material which can be used as the host material or additives can be used. There is no particular limitation on the host materials and the third substance as long as they can form an exciplex; a combination of a compound which readily accepts electrons (a compound having an electron-transport property) and a compound which readily accepts holes (a compound having a hole-transport property) is preferably employed.

In the case where a compound having an electron-transport property and a compound having a hole-transport property are used for the host material and the third substance, carrier balance can be controlled by the mixture ratio of the compounds. Specifically, the ratio of the host material to the third substance (or additive) is preferably from 1:9 to 9:1. Note that in that case, the following structure may be employed: a light-emitting layer in which one kind of a light-emitting substance is dispersed is divided into two layers, and the two layers have different mixture ratios of the host material to the third substance. With this structure, the carrier balance of the light-emitting element can be optimized, so that the lifetime of the light-emitting element can be improved. Furthermore, one of the light-emitting layers may be a hole-transport layer and the other of the light-emitting layers may be an electron-transport layer.

In the case where the light-emitting layer having the above-described structure is formed using a plurality of materials, the light-emitting layer can be formed using co-evaporation by a vacuum evaporation method; or an inkjet method, a spin coating method, a dip coating method, or the like with a solution of the materials.

The electron-transport layer 114 is a layer containing a substance having an electron-transport property. For example, the electron-transport layer 114 is formed using a metal complex having a quinoline skeleton or a benzoquinoline skeleton, such as tris(8-quinolinolato)aluminum (abbreviation: Alq), tris(4-methyl-8-quinolinolato)aluminum (abbreviation: $Almq_3$), bis(10-hydroxybenzo[h]quinolinato) beryllium (abbreviation: $BeBq_2$), or bis(2-methyl-8-quinolinolato)(4-phenylphenolato)aluminum (abbreviation: BAlq), or the like. A metal complex having an oxazole-based or thiazole-based ligand, such as bis[2-(2-hydroxyphenyl)benzoxazolato]zinc (abbreviation: $Zn(BOX)_2$) or bis [2-(2-hydroxyphenyl)benzothiazolato]zinc (abbreviation: $Zn(BTZ)_2$), or the like can also be used. Other than the metal complexes, 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), bathophenanthroline (abbreviation: BPhen), bathocuproine (abbreviation: BCP), or the like can also be used. The substances given here are mainly ones having an electron mobility of $10^{-6}$ $cm^2/Vs$ or higher. Note that any substance other than the above substances may be used for the electron-transport layer as long as the substance has an electron-transport property higher than a hole-transport property.

The compound with a benzofuropyrimidine skeleton may also be used as a material contained in the electron-transport layer 114. The compound with a benzofuropyrimidine skeleton has a wide band gap and a high triplet excitation level ($T_1$ level) and thus can effectively prevent transfer of excitation energy in the light-emitting layer to the electron-transport layer 114 to inhibit a reduction in emission efficiency due to the excitation energy transfer, and allow a light-emitting element having high emission efficiency to be fabricated. Moreover, the compound with a benzofuropyrimidine skeleton has a high carrier-transport property; thus, a light-emitting element having low driving voltage can be provided.

The electron-transport layer is not limited to a single layer, and may be a stack including two or more layers containing any of the above substances.

Between the electron-transport layer and the light-emitting layer, a layer that controls transport of electron carriers may be provided. This is a layer formed by addition of a small amount of a substance having a high electron-trapping property to the aforementioned materials having a high electron-transport property, and the layer is capable of adjusting carrier balance by retarding transport of electron carriers. Such a structure is very effective in preventing a problem (such as a reduction in element lifetime) caused when electrons pass through the light-emitting layer.

It is preferable that the host material in the light-emitting layer and a material of the electron-transport layer have the same skeleton, in which case transfer of carriers can be smooth and thus the driving voltage can be reduced. Moreover, it is effective that the host material and the material of the electron-transport layer be the same material.

The electron-injection layer 115 may be provided in contact with the second electrode 102 between the electron-transport layer 114 and the second electrode 102. For the electron-injection layer 115, lithium, calcium, lithium fluoride (LiF), cesium fluoride (CsF), or calcium fluoride ($CaF_2$) can be used. A composite material of a substance having an electron-transport property and a substance exhibiting an electron-donating property (hereinafter, simply referred to as electron-donating substance) with respect to the substance having an electron-transport property can also be used. Examples of the electron-donating substance include an alkali metal, an alkaline earth metal, and compounds thereof. Note that such a composite material is preferably used for the electron-injection layer 115, in which case electrons are injected efficiently from the second electrode 102. With this structure, a conductive material as well as a material having a low work function can be used for the cathode.

For the electrode functioning as a cathode, any of metals, alloys, electrically conductive compounds, and mixtures thereof which have a low work function (specifically, a work function of 3.8 eV or less) or the like can be used. Specific examples of such a cathode material include elements that belong to Groups 1 and 2 of the periodic table, i.e., alkali metals such as lithium (Li) and cesium (Cs), and alkaline earth metals such as magnesium (Mg), calcium (Ca), and strontium (Sr), alloys thereof (e.g., MgAg or AlLi), rare earth metals such as europium (Eu) and ytterbium (Yb), alloys thereof, and the like. However, when the electron-injection layer is provided between the second electrode 102 and the electron-transport layer, for the second electrode 102, any of a variety of conductive materials such as Al, Ag, ITO, or indium oxide-tin oxide containing silicon or silicon oxide can be used regardless of the work function. Films of these electrically conductive materials can be formed by a sputtering method, an inkjet method, a spin coating method, or the like.

Any of a variety of methods can be used to form the EL layer 103 regardless whether it is a dry process or a wet process. For example, a vacuum evaporation method, an inkjet method, a spin coating method, or the like may be used. Different formation methods may be used for the electrodes or the layers.

In addition, the electrode may be formed by a wet method using a sol-gel method, or by a wet method using paste of a metal material. Alternatively, the electrode may be formed by a dry method such as a sputtering method or a vacuum evaporation method.

Note that the structure of the EL layer provided between the first electrode 101 and the second electrode 102 is not limited to the above structure. However, it is preferable that a light-emitting region where holes and electrons recombine be positioned away from the first electrode 101 and the second electrode 102 so as to prevent quenching due to the proximity of the light-emitting region and a metal used for an electrode or a carrier-injection layer.

Further, in order that transfer of energy from an exciton generated in the light-emitting layer can be inhibited, preferably, the hole-transport layer and the electron-transport layer which are in direct contact with the light-emitting layer, particularly a carrier-transport layer in contact with a side closer to the light-emitting region in the light-emitting layer 113 is formed with a substance having a wider energy gap than the light-emitting substance of the light-emitting layer or the light-emitting substance included in the light-emitting layer.

In the light-emitting element having the above-described structure, current flows due to a potential difference between the first electrode 101 and the second electrode 102, and holes and electrons recombine in the light-emitting layer 113 which contains a substance having a high light-emitting property, so that light is emitted. In other words, a light-emitting region is formed in the light-emitting layer 113.

Light is extracted out through one or both of the first electrode 101 and the second electrode 102. Therefore, one or both of the first electrode 101 and the second electrode 102 are light-transmitting electrodes. In the case where only the first electrode 101 is a light-transmitting electrode, light is extracted from the substrate side through the first electrode 101. In contrast, when only the second electrode 102 is a light-transmitting electrode, light is extracted from the side opposite to the substrate side through the second electrode 102. In the case where both the first electrode 101 and the second electrode 102 are light-transmitting electrodes, light is extracted from both the substrate side and the side opposite to the substrate side through the first electrode 101 and the second electrode 102.

Since the light-emitting element of this embodiment is formed using the compound with a benzofuropyrimidine skeleton, which has a wide energy gap, efficient light emission can be obtained even if a light-emitting substance is any of a fluorescent substance emitting blue and a phosphorescent substance emitting a color between green and blue, which have a wide energy gap, and the light-emitting element can have high emission efficiency. Thus, a light-emitting element with lower power consumption can be provided. Further, the compound with a benzofuropyrimidine skeleton has a high carrier-transport property; thus, a light-emitting element having low driving voltage can be provided.

Such a light-emitting element may be fabricated using a substrate made of glass, plastic, or the like as a support. A plurality of such light-emitting elements are formed over one substrate, thereby forming a passive matrix light-emitting device. Alternatively, a transistor may be formed over a substrate made of glass, plastic, or the like, and the light-emitting element may be fabricated over an electrode electrically connected to the transistor. In this manner, an active matrix light-emitting device in which the driving of the light-emitting element is controlled by the transistor can be fabricated. Note that a structure of the transistor is not particularly limited. Either a staggered TFT or an inverted staggered TFT may be employed. In addition, the crystallinity of a semiconductor used for the TFT is not particularly limited. In addition, a driver circuit formed in a TFT substrate may be formed with n-type TFTs and p-type TFTs, or with either n-type TFTs or p-type TFTs. The semiconductor layer for forming the TFTs may be formed using any material as long as the material exhibits semiconductor characteristics; for example, an element belonging to Group 14 of the periodic table such as silicon (Si) and germanium (Ge), a compound such as gallium arsenide and indium phosphide, an oxide such as zinc oxide and tin oxide, and the like can be given. For the oxide exhibiting semiconductor characteristics (oxide semiconductor), composite oxide of an element selected from indium, gallium, aluminum, zinc, and tin can be used. Examples thereof are zinc oxide (ZnO), indium oxide containing zinc oxide (indium zinc oxide), and oxide containing indium oxide, gallium oxide, and zinc oxide (IGZO: indium gallium zinc oxide). An organic semiconductor may also be used. The semiconductor layer may have either a crystalline structure or an amorphous structure. Specific examples of the crystalline semiconductor layer are a single crystal semiconductor, a polycrystalline semiconductor, and a microcrystalline semiconductor.

EMBODIMENT 4

In this embodiment is described one mode of a light-emitting element having a structure in which a plurality of light-emitting units are stacked (hereinafter, also referred to as stacked-type element), with reference to FIG. 1B. This light-emitting element includes a plurality of light-emitting units between a first electrode and a second electrode. Each light-emitting unit can have the same structure as the EL layer 103 which is described in Embodiment 3. In other words, the light-emitting element described in Embodiment 3 is a light-emitting element having one light-emitting unit while the light-emitting element described in this embodiment is a light-emitting element having a plurality of light-emitting units.

Figure 1B:
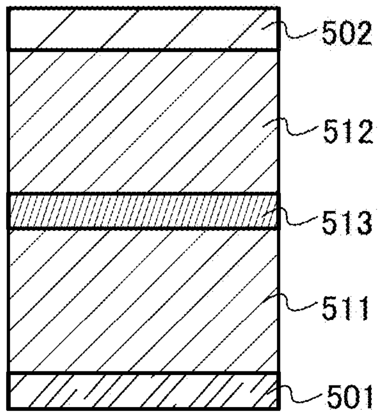

In FIG. 1B, a first light-emitting unit 511 and a second light-emitting unit 512 are stacked between a first electrode 501 and a second electrode 502, and a charge generation layer 513 is provided between the first light-emitting unit 511 and the second light-emitting unit 512. The first electrode 501 and the second electrode 502 respectively correspond to the first electrode 101 and the second electrode 102 in Embodiment 3, and materials described in Embodiment 3 can be used. Further, the structures of the first light-emitting unit 511 and the second light-emitting unit 512 may be the same or different.

The charge generation layer 513 includes a composite material of an organic compound and a metal oxide. As this composite material of an organic compound and a metal oxide, the composite material that can be used for the hole-injection layer and described in Embodiment 3 can be used. As the organic compound, any of a variety of compounds such as aromatic amine compounds, carbazole compounds, aromatic hydrocarbons, and high molecular compounds (oligomers, dendrimers, polymers, or the like) can be used. Note that the organic compound preferably has a hole mobility of $1\times10^{-6}$ $cm^2/Vs$ or more. However, any other substance may be used as long as the substance has a hole-transport property higher than an electron-transport property. Since a composite material of an organic compound and a metal oxide is excellent in carrier-injection property and carrier-transport property, low voltage driving and low current driving can be achieved. Note that in the light-emitting unit whose anode side surface is in contact with the charge generation layer, a hole-transport layer is not necessarily provided because the charge generation layer can also function as the hole-transport layer.

The charge generation layer 513 may have a stacked-layer structure of a layer containing the composite material of an organic compound and a metal oxide and a layer containing another material. For example, a layer containing the composite material of an organic compound and a metal oxide may be combined with a layer containing a compound of a substance selected from electron-donating substances and a compound having a high electron-transport property. Moreover, the charge generation layer 513 may be formed by combining a layer containing the composite material of an organic compound and a metal oxide with a transparent conductive film.

The charge generation layer 513 provided between the first light-emitting unit 511 and the second light-emitting unit 512 may have any structure as long as electrons can be injected to a light-emitting unit on one side and holes can be injected to a light-emitting unit on the other side when a voltage is applied between the first electrode 501 and the second electrode 502. For example, in FIG. 1B, any layer can be used as the charge generation layer 513 as long as the layer injects electrons into the first light-emitting unit 511 and holes into the second light-emitting unit 512 when a voltage is applied such that the potential of the first electrode is higher than that of the second electrode.

Although the light-emitting element having two light-emitting units is described in this embodiment, the present invention can be similarly applied to a light-emitting element in which three or more light-emitting units are stacked. With a plurality of light-emitting units partitioned by the charge generation layer between a pair of electrodes, as in the light-emitting element according to this embodiment, light with high luminance can be obtained while current density is kept low; thus, a light-emitting element having a long lifetime can be obtained. In addition, a low power consumption light-emitting device which can be driven at low voltage can be achieved.

By making the light-emitting units emit light of different colors from each other, the light-emitting element can provide light emission of a desired color as a whole. For example, by forming a light-emitting element having two light-emitting units such that the emission color of the first light-emitting unit and the emission color of the second light-emitting unit are complementary colors, the light-emitting element can provide white light emission as a whole. Note that the word “complementary” means color relationship in which an achromatic color is obtained when colors are mixed. In other words, when lights obtained from substances which emit light of complementary colors are mixed, white light emission can be obtained. Further, the same can be applied to a light-emitting element having three light-emitting units. For example, the light-emitting element as a whole can provide white light emission when the emission color of the first light-emitting unit is red, the emission color of the second light-emitting unit is green, and the emission color of the third light-emitting unit is blue. Alternatively, in the case of employing a light-emitting element in which a phosphorescent substance is used for a light-emitting layer of one light-emitting unit and a fluorescent substance is used for a light-emitting layer of the other light-emitting unit, both fluorescence and phosphorescence can be efficiently emitted from the light-emitting element. For example, when red phosphorescence and green phosphorescence are obtained from one light-emitting unit and blue fluorescence is obtained from the other light-emitting unit, white light with high emission efficiency can be obtained.

Since the light-emitting element of this embodiment contains the compound with a benzofuropyrimidine skeleton, the light-emitting element can have high emission efficiency or operate at low driving voltage. In addition, since light emission with high color purity which is derived from the light-emitting substance can be obtained from the light-emitting unit including the compound, color adjustment of the light-emitting element as a whole is easy.

Note that this embodiment can be combined with any of the other embodiments as appropriate.

EMBODIMENT 5

In this embodiment, a light-emitting device that uses a light-emitting element including a compound with a benzofuropyrimidine skeleton will be described.

Figure 3A:
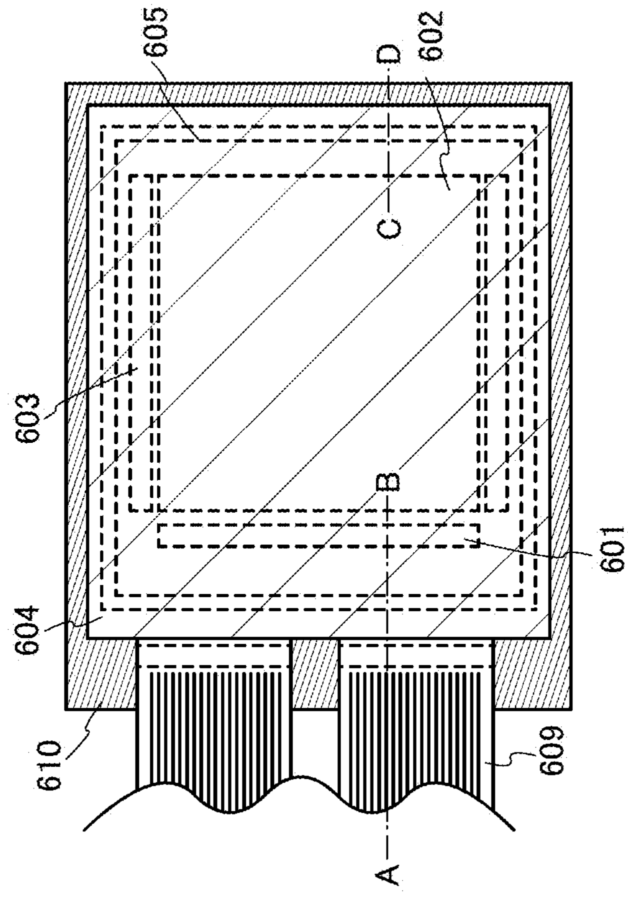
FIGS. 3A and 3B are schematic diagrams of an active matrix light-emitting device.
Figure 3B:
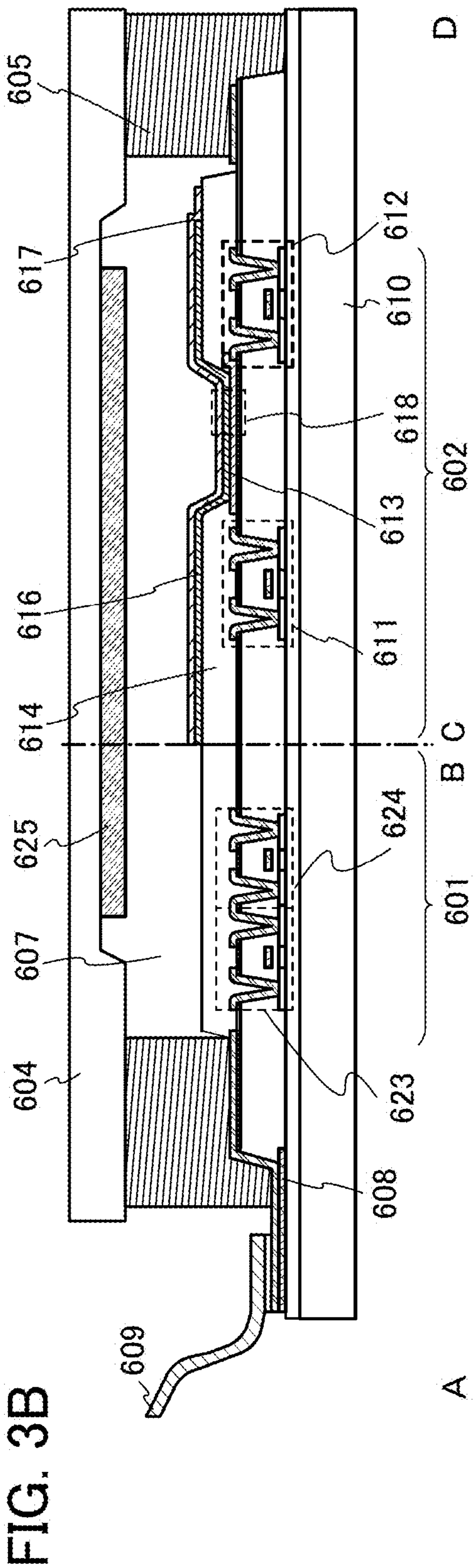

In this embodiment, explanation will be given with reference to FIGS. 3A and 3B of an example of the light-emitting device fabricated using a light-emitting element including a compound with a benzofuropyrimidine skeleton. Note that FIG. 3A is a top view of the light-emitting device and FIG. 3B is a cross-sectional view taken along the lines A-B and C-D in FIG. 3A. This light-emitting device includes a driver circuit portion (source side driver circuit) 601, a pixel portion 602, and a driver circuit portion (gate side driver circuit) 603, which control light emission of a light-emitting element 618 and denoted by dotted lines. A reference numeral 604 denotes a sealing substrate; 625, a desiccant; 605, a sealing material; and 607, a space surrounded by the sealing material 605.

Reference numeral 608 denotes a wiring for transmitting signals to be input to the source side driver circuit 601 and the gate side driver circuit 603 and receiving signals such as a video signal, a clock signal, a start signal, and a reset signal from an FPC (flexible printed circuit) 609 serving as an external input terminal. Although only the FPC is illustrated here, a printed wiring board (PWB) may be attached to the FPC. The light-emitting device in the present specification includes, in its category, not only the light-emitting device itself but also the light-emitting device provided with the FPC or the PWB.

Next, a cross-sectional structure is explained with reference to FIG. 3B. The driver circuit portion and the pixel portion are formed over an element substrate 610; here, the source line driver circuit 601, which is a driver circuit portion, and one of the pixels in the pixel portion 602 are shown.

As the source line driver circuit 601, a CMOS circuit in which an n-channel TFT 623 and a p-channel TFT 624 are combined is formed. In addition, the driver circuit may be formed with any of a variety of circuits such as a CMOS circuit, a PMOS circuit, and an NMOS circuit. Although a driver integrated type in which the driver circuit is formed over the substrate is illustrated in this embodiment, the driver circuit is not necessarily formed over the substrate, and the driver circuit can be formed outside, not over the substrate.

The pixel portion 602 includes a plurality of pixels including a switching TFT 611, a current controlling TFT 612, and a first electrode 613 electrically connected to a drain of the current controlling TFT 612. Note that to cover an end portion of the first electrode 613, an insulator 614 is formed, for which a positive photosensitive resin film is used here.

In order to improve coverage of a film formed over the insulator 614, the insulator 614 is formed to have a curved surface with curvature at its upper or lower end portion. For example, in the case where a positive photosensitive acrylic resin is used for a material of the insulator 614, only the upper end portion of the insulator 614 preferably has a surface with a curvature radius (0.2 μm to 3 μm). As the insulator 614, either a negative photosensitive material or a positive photosensitive material can be used.

An EL layer 616 and a second electrode 617 are formed over the first electrode 613. As a material used for the first electrode 613 which functions as an anode, a material having a high work function is preferably used. For example, a single-layer film of an ITO film, an indium tin oxide film containing silicon, an indium oxide film containing zinc oxide at 2 wt % to 20 wt %, a titanium nitride film, a chromium film, a tungsten film, a Zn film, a Pt film, or the like, a stack including a titanium nitride film and a film containing aluminum as its main component, a stack including three layers of a titanium nitride film, a film containing aluminum as its main component, and a titanium nitride film, or the like can be used. The stacked structure achieves low wiring resistance, a favorable ohmic contact, and a function as an anode.

The EL layer 616 is formed by any of a variety of methods such as an evaporation method using an evaporation mask, an inkjet method, and a spin coating method. The EL layer 616 contains the compound with a benzofuropyrimidine skeleton. Further, for another material included in the EL layer 616, any of low molecular-weight compounds and polymeric compounds (including oligomers and dendrimers) may be used.

As a material used for the second electrode 617, which is formed over the EL layer 616 and functions as a cathode, a material having a low work function (e.g., Al, Mg, Li, Ca, or an alloy or compound thereof, such as MgAg, MgIn, or AlLi) is preferably used. In the case where light generated in the EL layer 616 passes through the second electrode 617, a stack including a thin metal film and a transparent conductive film (e.g., ITO, indium oxide containing zinc oxide at 2 wt % to 20 wt %, indium tin oxide containing silicon, or zinc oxide (ZnO)) is preferably used for the second electrode 617.

Note that the light-emitting element is formed with the first electrode 613, the EL layer 616, and the second electrode 617. The light-emitting element has the structure described in Embodiment 3 or 4. In the light-emitting device of this embodiment, the pixel portion, which includes a plurality of light-emitting elements, may include both the light-emitting element with the structure described in Embodiment 3 or 4 and a light-emitting element with a structure other than those.

The sealing substrate 604 is attached to the element substrate 610 with the sealing material 605, so that the light-emitting element 618 is provided in the space 607 surrounded by the element substrate 610, the sealing substrate 604, and the sealing material 605. The space 607 is filled with filler. The filler may be an inert gas (such as nitrogen or argon), a resin, or a resin and/or a desiccant.

An epoxy-based resin or glass frit is preferably used for the sealing material 605. It is preferable that such a material do not transmit moisture or oxygen as much as possible. As the sealing substrate 604, a glass substrate, a quartz substrate, or a plastic substrate formed of fiber reinforced plastic (FRP), poly(vinyl fluoride) (PVF), a polyester, an acrylic resin, or the like can be used.

As described above, the light-emitting device fabricated by using the light-emitting element that contains the compound with a benzofuropyrimidine skeleton can be obtained.

Figure 4A:
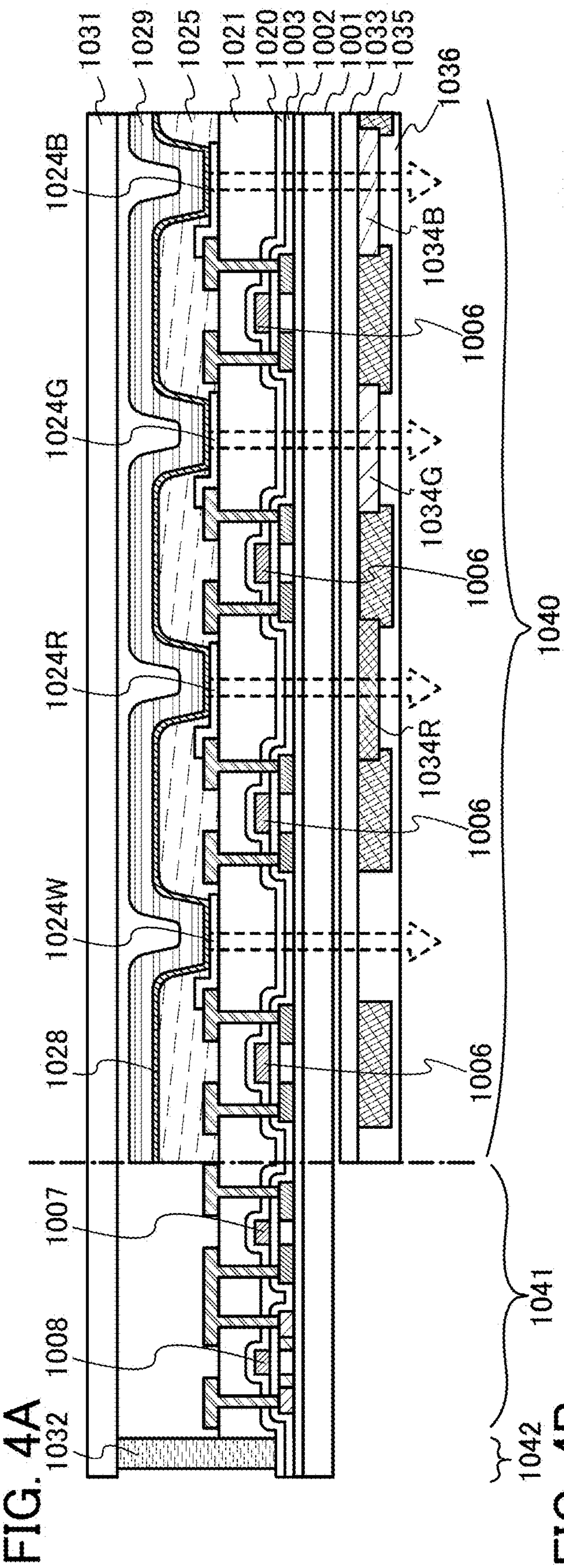
FIGS. 4A and 4B are schematic diagrams of active matrix light-emitting devices.
Figure 4B:
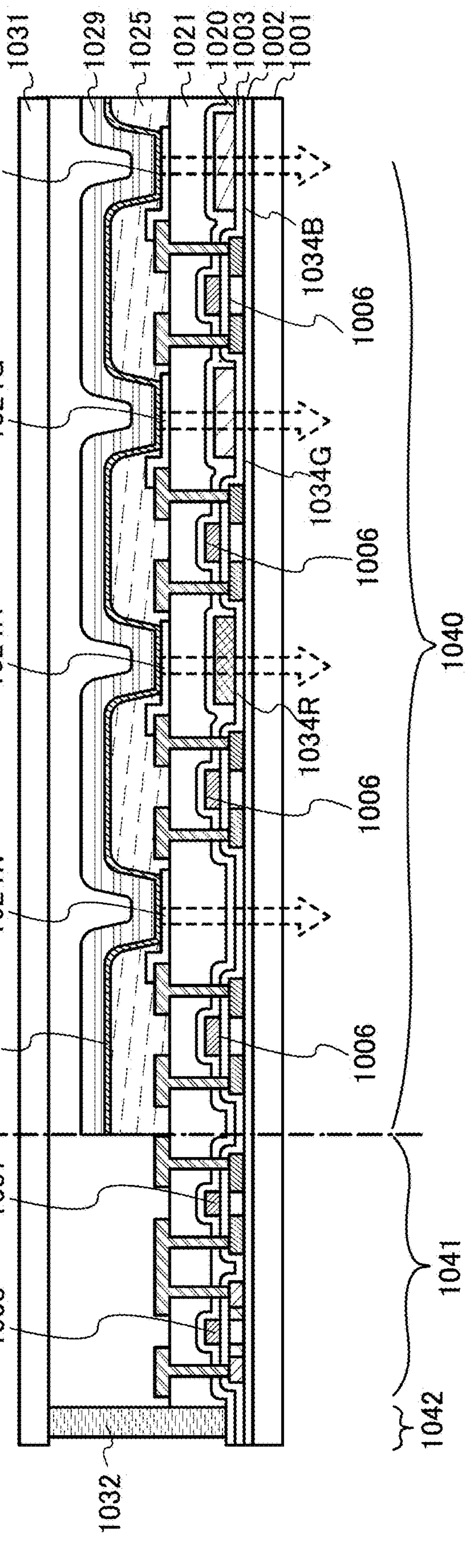

FIGS. 4A and 4B illustrates examples of light-emitting devices in which full color display is achieved by forming a light-emitting element exhibiting white light emission and providing a coloring layer (a color filter) and the like. In FIG. 4A, a substrate 1001, a base insulating film 1002, a gate insulating film 1003, gate electrodes 1006, 1007, and 1008, a first interlayer insulating film 1020, a second interlayer insulating film 1021, a peripheral portion 1042, a pixel portion 1040, a driver circuit portion 1041, first electrodes 1024W, 1024R, 1024G, and 1024B of light-emitting elements, a partition wall 1025, an EL layer 1028, a second electrode 1029 of the light-emitting elements, a sealing substrate 1031, a sealant 1032, and the like are illustrated.

In FIG. 4A, coloring layers (a red coloring layer 1034R, a green coloring layer 1034G, and a blue coloring layer 1034B) are provided on a transparent base material 1033. Further, a black layer (a black matrix) 1035 may be additionally provided. The transparent base material 1033 provided with the coloring layers and the black layer is positioned and fixed to the substrate 1001. Note that the coloring layers and the black layer are covered with an overcoat layer 1036. In FIG. 4A, light emitted from some of the light-emitting layers does not pass through the coloring layers, while light emitted from the others of the light-emitting layers passes through the coloring layers. Since light which does not pass through the coloring layers is white and light which passes through any one of the coloring layers is red, blue, or green, an image can be displayed using pixels of the four colors.

FIG. 4B illustrates an example in which coloring layers (a red coloring layer 1034R, a green coloring layer 1034G, and a blue coloring layer 1034B) are formed between the gate insulating film 1003 and the first interlayer insulating film 1020. As shown in FIG. 4B, the coloring layers may be provided between the substrate 1001 and the sealing substrate 1031.

Figure 5:
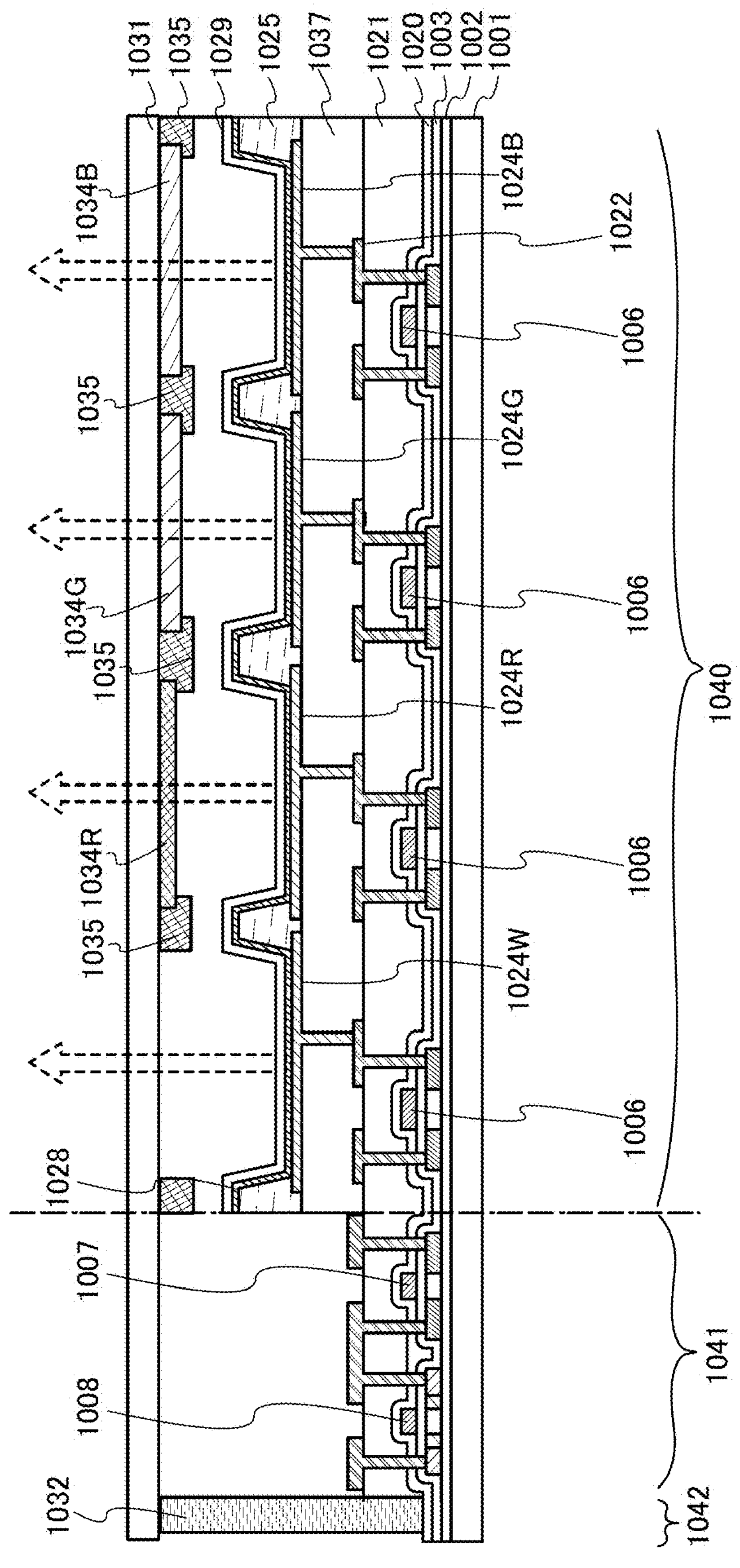
FIG. 5 is a schematic diagram of an active matrix light-emitting device.

The above-described light-emitting device has a structure in which light is extracted from the substrate 1001 side where the TFTs are formed (a bottom emission structure), but may have a structure in which light is extracted from the sealing substrate 1031 side (a top emission structure). FIG. 5 is a cross-sectional view of a light-emitting device having a top emission structure. In this case, a substrate which does not transmit light can be used as the substrate 1001. The process up to the step of forming a connection electrode which connects the TFT and the anode of the light-emitting element is performed in a manner similar to that of the light-emitting device having a bottom emission structure. Then, a third interlayer insulating film 1037 is formed to cover an electrode 1022. This insulating film may have a planarization function. The third interlayer insulating film 1037 can be formed using a material similar to that of the second interlayer insulating film, and can alternatively be formed using any other known material.

The first electrodes 1024W, 1024R, 1024G, and 1024B of the light-emitting elements each serve as an anode here, but may serve as a cathode. Further, in the case of a light-emitting device having a top emission structure as illustrated in FIG. 5, the first electrodes are preferably reflective electrodes. The EL layer 1028 is formed to have a structure similar to the structure described in Embodiments 3 and 4, with which white light emission can be obtained.

In FIGS. 4A and 4B and FIG. 5, the structure of the EL layer for providing white light emission can be achieved by, for example, using a plurality of light-emitting layers or using a plurality of light-emitting units. Note that the structure to provide white light emission is not limited to the above.

In the case of a top emission structure as illustrated in FIG. 5, sealing can be performed with the sealing substrate 1031 on which the coloring layers (the red coloring layer 1034R, the green coloring layer 1034G, and the blue coloring layer 1034B) are provided. The sealing substrate 1031 may be provided with the black layer (the black matrix) 1035 which is positioned between pixels. The coloring layers (the red coloring layer 1034R, the green coloring layer 1034G, and the blue coloring layer 1034B) and the black layer (the black matrix) may be covered with the overcoat layer as described in FIG. 4A. Note that a light-transmitting substrate is used as the sealing substrate 1031.

Although an example in which full color display is performed using four colors of red, green, blue, and white is shown here, there is no particular limitation and full color display using three colors of red, green, and blue may be performed.

Since the light-emitting device of this embodiment uses the light-emitting element described in Embodiment 3 or 4 (the light-emitting element including the compound with a benzofuropyrimidine skeleton), the light-emitting device can have favorable characteristics. Specifically, the compound with a benzofuropyrimidine skeleton has a wide energy gap and a high triplet excitation level ($T_1$ level) and can inhibit energy transfer from a light-emitting substance; thus, a light-emitting element having high emission efficiency can be provided, leading to a light-emitting device having reduced power consumption. Furthermore, the compound with a benzofuropyrimidine skeleton has a high carrier-transport property, so that a light-emitting element with low driving voltage can be provided, leading to a light-emitting device with low driving voltage.

Figure 6A:
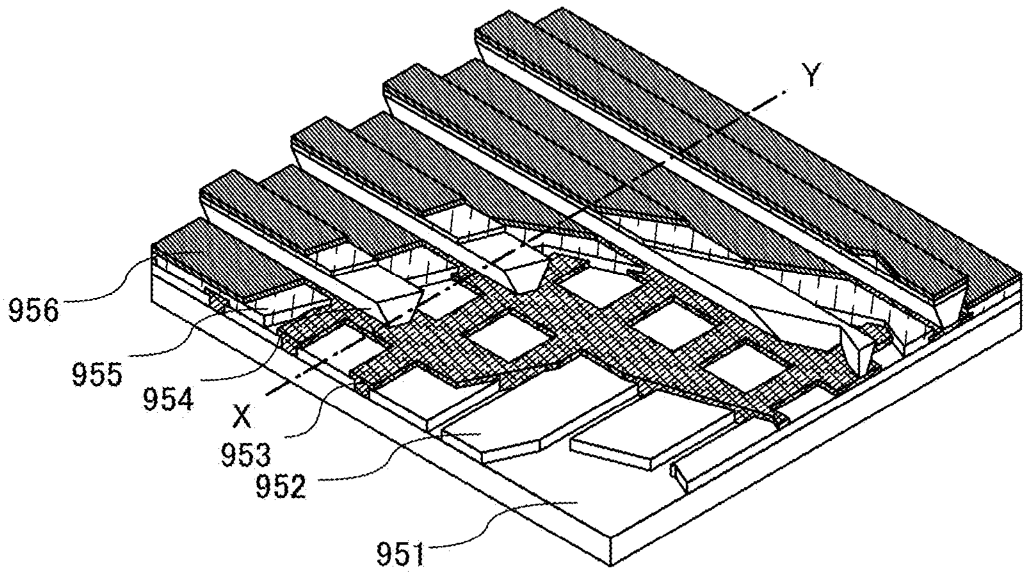
FIGS. 6A and 6B are schematic diagrams of a passive matrix light-emitting device.
Figure 6B:
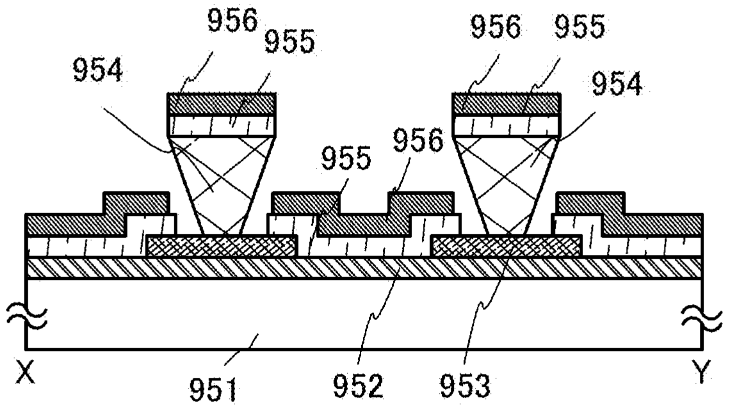

An active matrix light-emitting device is described above, whereas a passive matrix light-emitting device is described below. FIGS. 6A and 6B illustrate a passive matrix light-emitting device fabricated by application of the present invention. FIG. 6A is a perspective view of the light-emitting device, and FIG. 6B is a cross-sectional view of FIG. 6A taken along line X-Y In FIGS. 6A and 6B, over a substrate 951, an EL layer 955 is provided between an electrode 952 and an electrode 956. An edge portion of the electrode 952 is covered with an insulating layer 953. A partition layer 954 is provided over the insulating layer 953. The sidewalls of the partition layer 954 slope so that the distance between one sidewall and the other sidewall gradually decreases toward the surface of the substrate. In other words, a cross section taken along the direction of the short side of the partition layer 954 is trapezoidal, and the base (a side which is in the same direction as a plane direction of the insulating layer 953 and in contact with the insulating layer 953) is shorter than the upper side (a side which is in the same direction as the plane direction of the insulating layer 953 and not in contact with the insulating layer 953). By providing the partition layer 954 in such a manner, a defect of the light-emitting element due to static electricity or the like can be prevented. The passive matrix light-emitting device can also be driven with low power consumption, by including the light-emitting element described in Embodiment 3 or 4 (the light-emitting element including the compound with a benzofuropyrimidine skeleton) capable of operating at low driving voltage.

Since many minute light-emitting elements arranged in a matrix in the light-emitting device described above can each be controlled, the light-emitting device can be suitably used as a display device for displaying images.

EMBODIMENT 6

In this embodiment, electronic devices each including the light-emitting element described in Embodiment 3 or 4 will be described. The light-emitting element described in Embodiment 3 or 4 includes the compound with a benzofuropyrimidine skeleton and thus has reduced power consumption; as a result, the electronic devices described in this embodiment can each include a display portion having reduced power consumption. In addition, the electronic devices can have low driving voltage since the light-emitting element described in Embodiment 3 or 4 has low driving voltage.

Examples of the electronic device to which the above light-emitting element is applied include television devices (also referred to as TV or television receivers), monitors for computers and the like, cameras such as digital cameras and digital video cameras, digital photo frames, cellular phones (also referred to as mobile phones or mobile phone devices), portable game machines, portable information terminals, audio playback devices, large game machines such as pachinko machines, and the like. Specific examples of these electronic devices are given below.

Figure 7A:
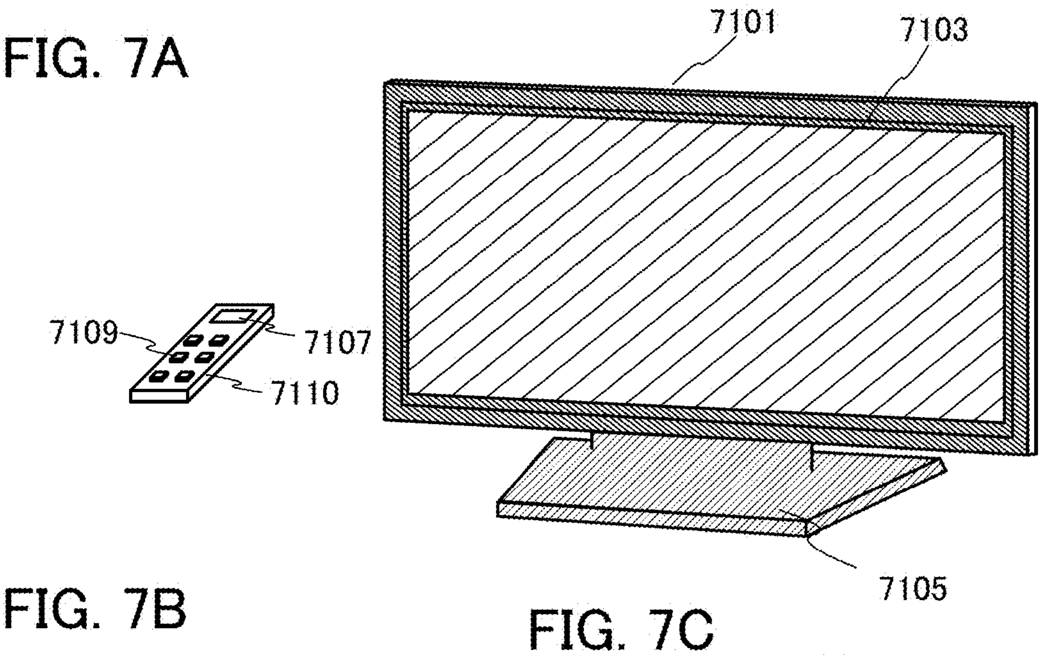
FIGS. 7A to 7D illustrate electronic devices.

FIG. 7A illustrates an example of a television device. In the television device, a display portion 7103 is incorporated in a housing 7101. In addition, here, the housing 7101 is supported by a stand 7105. The display portion 7103 enables display of images and includes light-emitting elements which are the same as the light-emitting element described in Embodiment 3 or 4 and arranged in a matrix. The light-emitting elements each include the compound with a benzofuropyrimidine skeleton and thus can have high emission efficiency and low driving voltage. Therefore, the television device including the display portion 7103 which is formed using the light-emitting elements can have reduced power consumption and low driving voltage.

The television device can be operated with an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television device is provided with a receiver, a modem, and the like. With the use of the receiver, general television broadcasting can be received. Moreover, when the television device is connected to a communication network with or without wires via the modem, one-way (from a sender to a receiver) or two-way (between a sender and a receiver or between receivers) information communication can be performed.

Figure 7B:
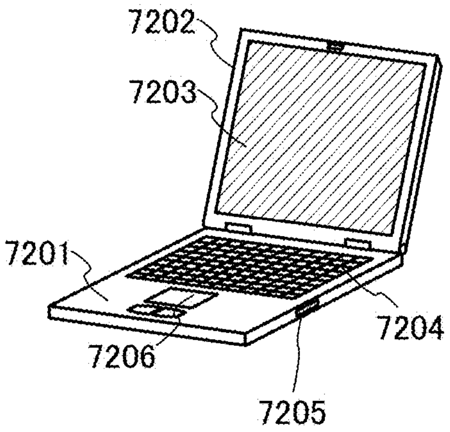

FIG. 7B illustrates a computer, which includes a main body 7201, a housing 7202, a display portion 7203, a keyboard 7204, an external connection port 7205, a pointing device 7206, and the like. Note that this computer is fabricated by using light-emitting elements arranged in a matrix in the display portion 7203, which are the same as that described in Embodiment 3 or 4. The light-emitting elements each include the compound with a benzofuropyrimidine skeleton and thus can have high emission efficiency and low driving voltage. Therefore, the computer including the display portion 7203 which is formed using the light-emitting elements can have reduced power consumption and low driving voltage.

Figure 7C:
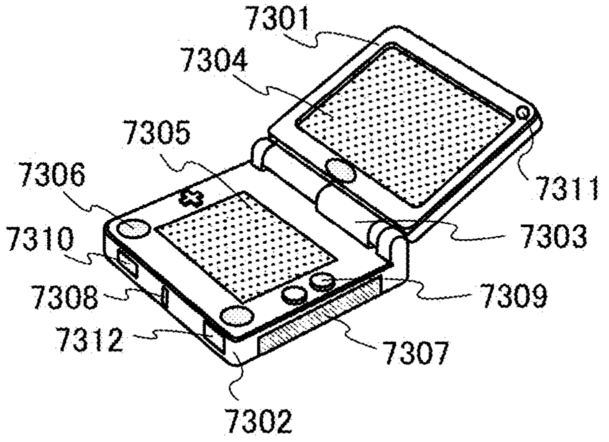

FIG. 7C illustrates a portable game machine having two housings, a housing 7301 and a housing 7302, which are connected with a joint portion 7303 so that the portable game machine can be opened or folded. A display portion 7304 including light-emitting elements which are the same as that described in Embodiment 3 or 4 and arranged in a matrix is incorporated in the housing 7301, and a display portion 7305 is incorporated in the housing 7302. In addition, the portable game machine illustrated in FIG. 7C includes a speaker portion 7306, a recording medium insertion portion 7307, an LED lamp 7308, an input unit (an operation key 7309, a connection terminal 7310, a sensor 7311 (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), and a microphone 7312), and the like. Needless to say, the structure of the portable game machine is not limited to the above as far as the display portion including light-emitting elements which are the same as that described in Embodiment 3 or 4 and arranged in a matrix is used as at least either the display portion 7304 or the display portion 7305, or both, and the structure can include other accessories as appropriate. The portable game machine illustrated in FIG. 7C has a function of reading out a program or data stored in a storage medium to display it on the display portion, and a function of sharing information with another portable game machine by wireless communication. The portable game machine illustrated in FIG. 7C can have a variety of functions without limitation to the above. Since the light-emitting elements used in the display portion 7304 have high emission efficiency by including the compound with a benzofuropyrimidine skeleton, the portable game machine including the above-described display portion 7304 can be a portable game machine having reduced power consumption. Since the light-emitting elements used in the display portion 7304 each have low driving voltage by including the compound with a benzofuropyrimidine skeleton, the portable game machine can also be a portable game machine having low driving voltage.

Figure 7D:
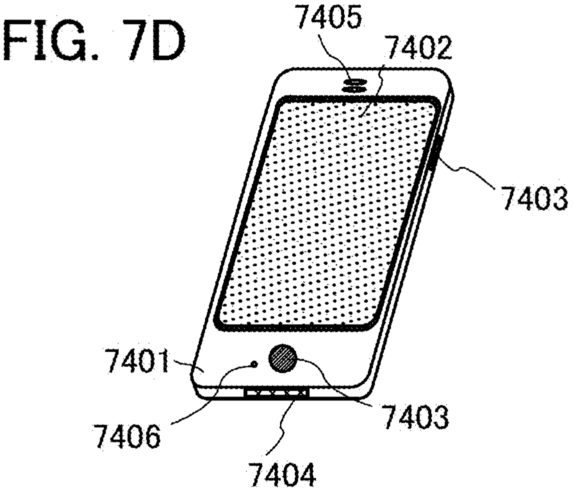

FIG. 7D illustrates an example of a mobile phone. A mobile phone is provided with a display portion 7402 incorporated in a housing 7401, operation buttons 7403, an external connection port 7404, a speaker 7405, a microphone 7406, and the like. Note that the mobile phone has the display portion 7402 including light-emitting elements which are the same as that described in Embodiment 3 or 4 and arranged in a matrix. The light-emitting elements each include the compound with a benzofuropyrimidine skeleton and thus can have high emission efficiency and low driving voltage. Therefore, the mobile phone including the display portion 7402 which is formed using the light-emitting elements can have reduced power consumption and low driving voltage.

When the display portion 7402 of the mobile phone illustrated in FIG. 7D is touched with a finger or the like, data can be input into the mobile phone. In this case, operations such as making a call and creating e-mail can be performed by touching the display portion 7402 with a finger or the like.

There are mainly three screen modes of the display portion 7402. The first mode is a display mode mainly for displaying an image. The second mode is an input mode mainly for inputting information such as characters. The third mode is a display-and-input mode in which two modes of the display mode and the input mode are combined.

For example, in the case of making a call or creating e-mail, a character input mode mainly for inputting characters is selected for the display portion 7402 so that characters displayed on a screen can be input. In this case, it is preferable to display a keyboard or number buttons on almost the entire screen of the display portion 7402.

When a detection device including a sensor for detecting inclination, such as a gyroscope or an acceleration sensor, is provided inside the cellular phone, display on the screen of the display portion 7402 can be automatically changed by determining the orientation of the cellular phone (whether the cellular phone is placed horizontally or vertically for a landscape mode or a portrait mode).

The screen modes are switched by touch on the display portion 7402 or operation with the operation buttons 7403 of the housing 7401. The screen modes can be switched depending on the kind of images displayed on the display portion 7402. For example, when a signal of an image displayed on the display portion is a signal of moving image data, the screen mode is switched to the display mode. When the signal is a signal of text data, the screen mode is switched to the input mode.

Moreover, in the input mode, when input by touching the display portion 7402 is not performed for a certain period while a signal detected by an optical sensor in the display portion 7402 is detected, the screen mode may be controlled so as to be switched from the input mode to the display mode.

The display portion 7402 may function as an image sensor. For example, an image of a palm print, a fingerprint, or the like is taken by touch on the display portion 7402 with the palm or the finger, whereby personal authentication can be performed. Further, by providing a backlight or a sensing light source which emits a near-infrared light in the display portion, an image of a finger vein, a palm vein, or the like can be taken.

Note that the structure described in this embodiment can be combined with any of the structures described in Embodiments 1 to 5 as appropriate.

As described above, the application range of the light-emitting device having the light-emitting element described in Embodiment 3 or 4 which includes the compound with a benzofuropyrimidine skeleton is wide so that this light-emitting device can be applied to electronic devices in a variety of fields. By using the compound with a benzofuropyrimidine skeleton, an electronic device having reduced power consumption and low driving voltage can be obtained.

The light-emitting element including the compound with a benzofuropyrimidine skeleton can also be used for alight source device. One mode of application of the light-emitting element including the compound with a benzofuropyrimidine skeleton to a light source device is described with reference to FIG. 8. Note that the light source device includes a light-emitting element including the compound with a benzofuropyrimidine skeleton as a light irradiation unit and at least includes an input-output terminal portion which supplies current to the light-emitting element. Further, the light-emitting element is preferably shielded from the outside atmosphere by sealing.

Figure 8:
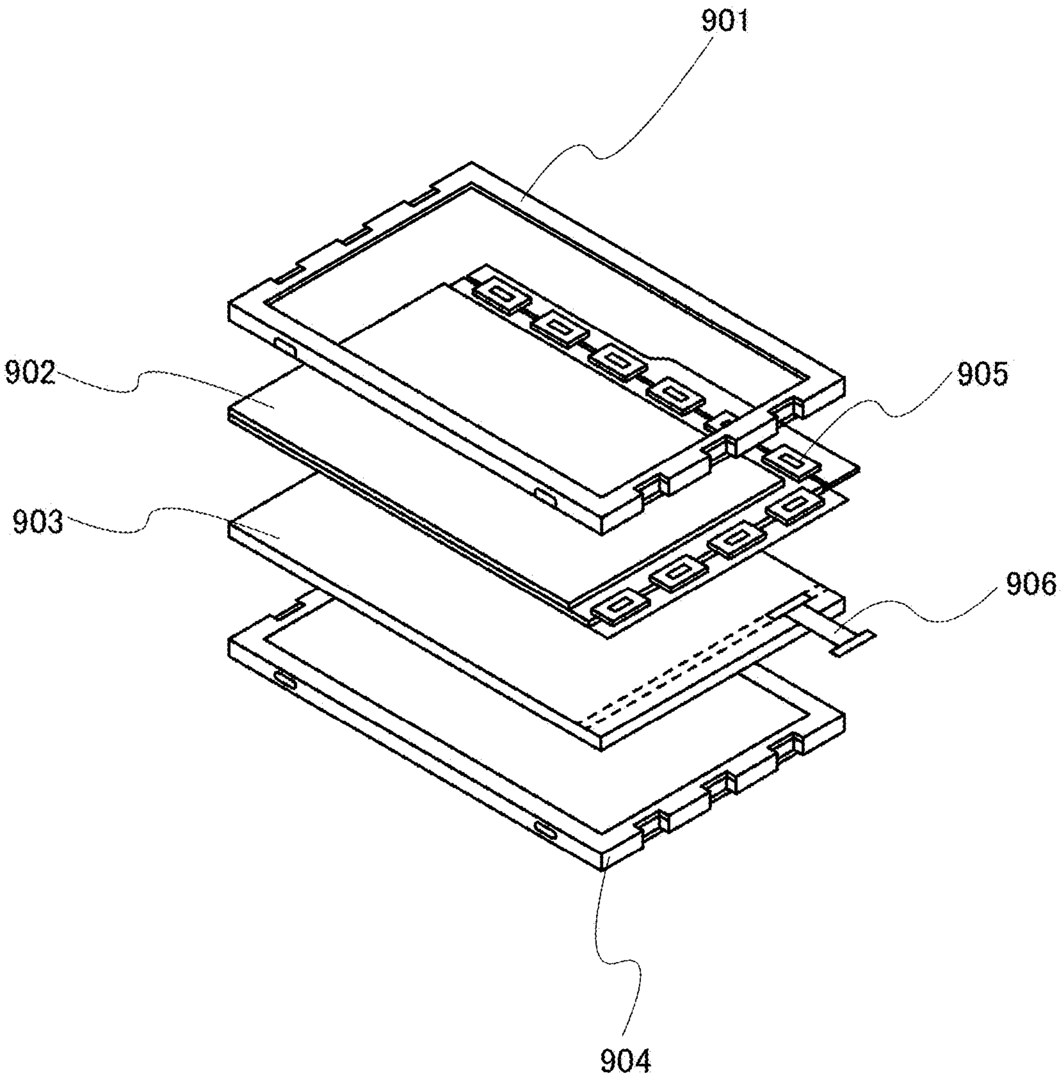
FIG. 8 illustrates a light source device.

FIG. 8 illustrates an example of a liquid crystal display device using the light-emitting elements including the compound with a benzofuropyrimidine skeleton for a backlight. The liquid crystal display device illustrated in FIG. 8 includes a housing 901, a liquid crystal layer 902, a backlight 903, and a housing 904. The liquid crystal layer 902 is connected to a driver IC 905. The light-emitting element including the above compound is used in the backlight 903, to which current is supplied through a terminal 906.

The light-emitting element including the above compound is used for the backlight of the liquid crystal display device; thus, the backlight can have reduced power consumption. In addition, the use of the light-emitting element including the above compound enables fabrication of a planar-emission lighting device and further a larger-area planar-emission lighting device; therefore, the backlight can be a larger-area backlight, and the liquid crystal display device can also be a larger-area device. Furthermore, the backlight using the light-emitting element including the above compound can be thinner than a conventional one; accordingly, the display device can also be thinner.

Figure 9:
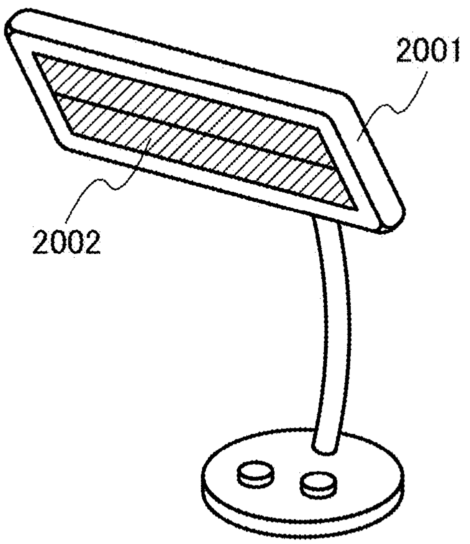
FIG. 9 illustrates a lighting device.

FIG. 9 illustrates an example in which the light-emitting element including the compound with a benzofuropyrimidine skeleton is used for a table lamp which is a lighting device. The table lamp illustrated in FIG. 9 includes a housing 2001 and a light source 2002, and the light-emitting element including the above compound is used for the light source 2002.

Figure 10:
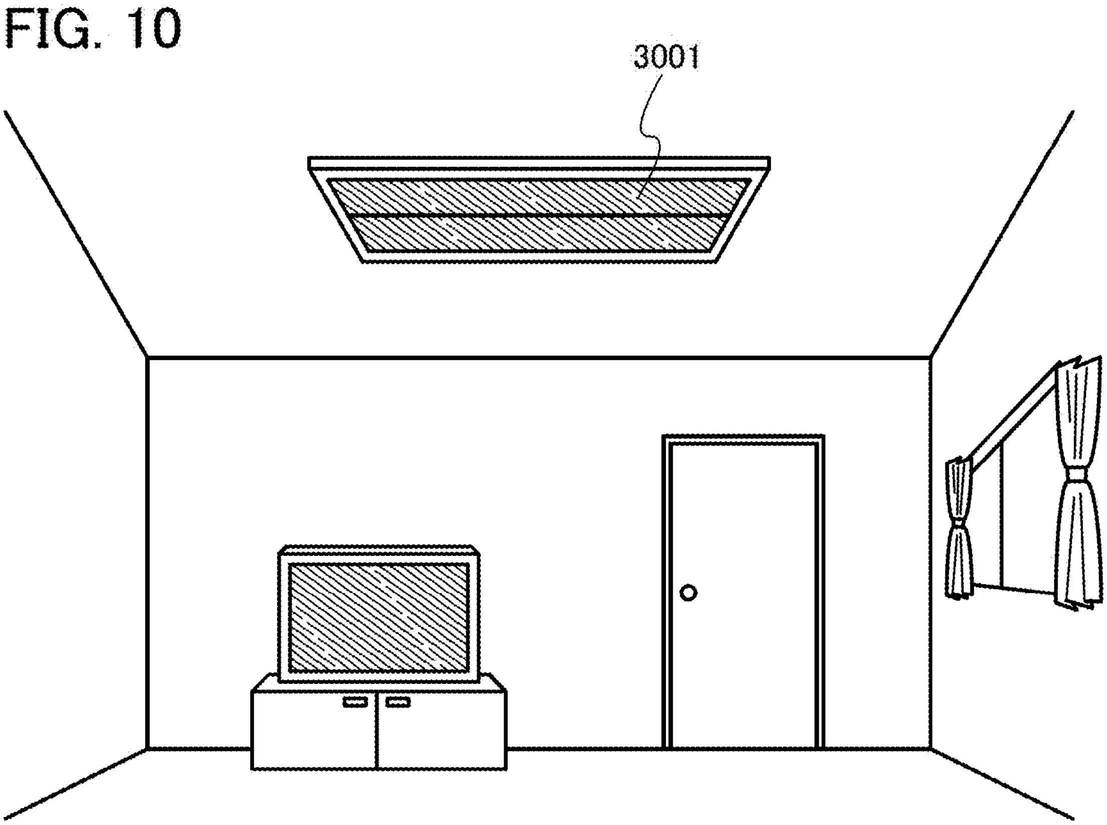
FIG. 10 illustrates a lighting device and an electronic device.

FIG. 10 illustrates an example in which the light-emitting element including the compound with a benzofuropyrimidine skeleton is used for an indoor lighting device 3001. Since the light-emitting element including the above compound has reduced power consumption, a lighting device that has reduced power consumption can be obtained. Further, since the light-emitting element including the above compound can have a large area, the light-emitting element can be used for a large-area lighting device. Furthermore, since the light-emitting element including the above compound is thin, a lighting device having a reduced thickness can be fabricated.

Figure 11:
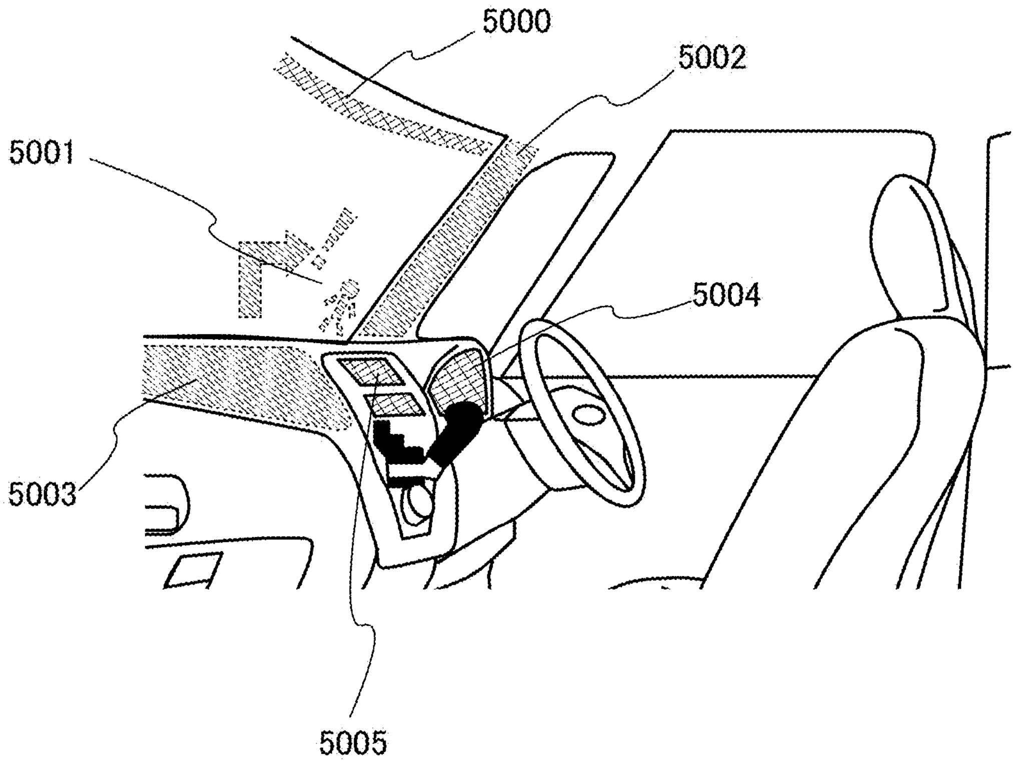
FIG. 11 illustrates in-vehicle display devices and lighting devices.

The light-emitting element including the compound with a benzofuropyrimidine skeleton can also be used for an automobile windshield or an automobile dashboard. FIG. 11 illustrates one mode in which the light-emitting elements including the above compound are used for an automobile windshield and an automobile dashboard. Display regions 5000 to 5005 each include the light-emitting element including the above compound.

The display regions 5000 and 5001 are display devices which are provided in the automobile windshield and in which light-emitting elements including the above compound are incorporated. The light-emitting element including the above compound can be formed into a so-called see-through display device, through which the opposite side can be seen, by including a first electrode and a second electrode formed of electrodes having light-transmitting properties. Such see-through display devices can be provided even in the windshield of the car, without hindering the vision. Note that in the case where a transistor for driving the light-emitting element is provided, a transistor having a light-transmitting property, such as an organic transistor using an organic semiconductor material or a transistor using an oxide semiconductor, is preferably used.

The display region 5002 is a display device which is provided in a pillar portion and in which the light-emitting element including the above compound is incorporated. The display region 5002 can compensate for the view hindered by the pillar portion by showing an image taken by an imaging unit provided in the car body. Similarly, the display region 5003 provided in the dashboard can compensate for the view hindered by the car body by showing an image taken by an imaging unit provided in the outside of the car body, which leads to elimination of blind areas and enhancement of safety. Showing an image so as to compensate for the area which a driver cannot see makes it possible for the driver to confirm safety easily and comfortably.

The display region 5004 and the display region 5005 can provide a variety of kinds of information such as navigation data, a speedometer, a tachometer, a mileage, a fuel meter, a gearshift indicator, and air-condition setting. The content or layout of the display can be changed freely by a user as appropriate. Note that such information can also be shown by the display regions 5000 to 5003. The display regions 5000 to 5005 can also be used as lighting devices.

By including the compound with a benzofuropyrimidine skeleton, the light-emitting element including the above compound has low driving voltage and lower power consumption. Therefore, load on a battery is small even when a number of large screens such as the display regions 5000 to 5005 are provided, which provides comfortable use. For that reason, the light-emitting device and the lighting device each of which includes the light-emitting element including the above compound can be suitably used as an in-vehicle light-emitting device and lighting device.

Figure 12A:
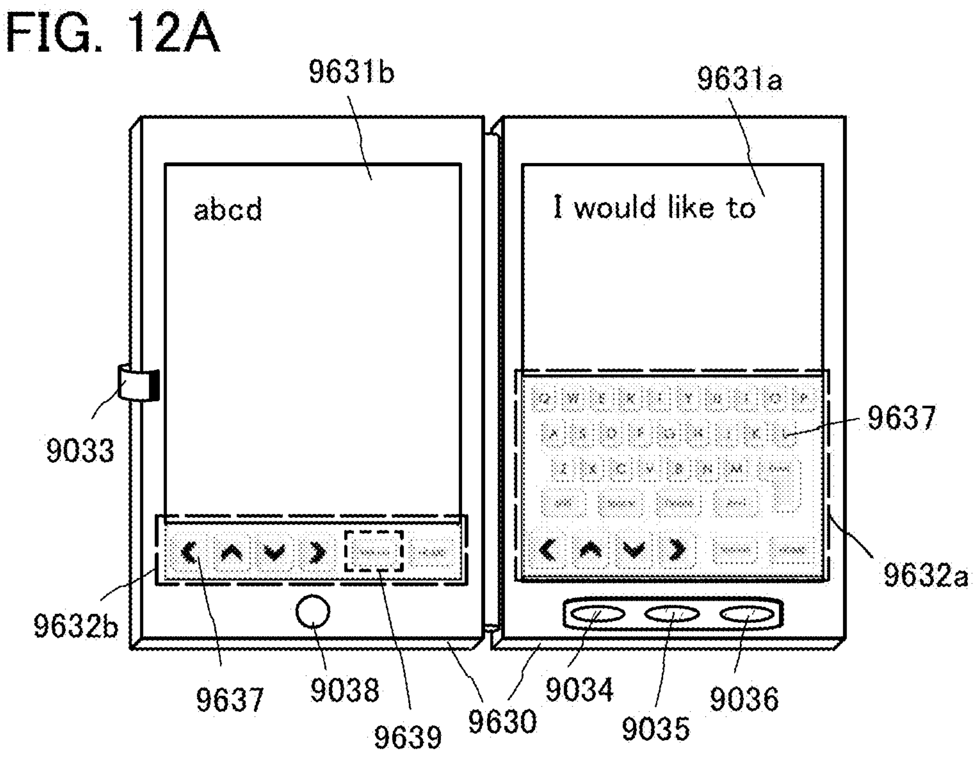
FIGS. 12A to 12C illustrate an electronic device.
Figure 12B:
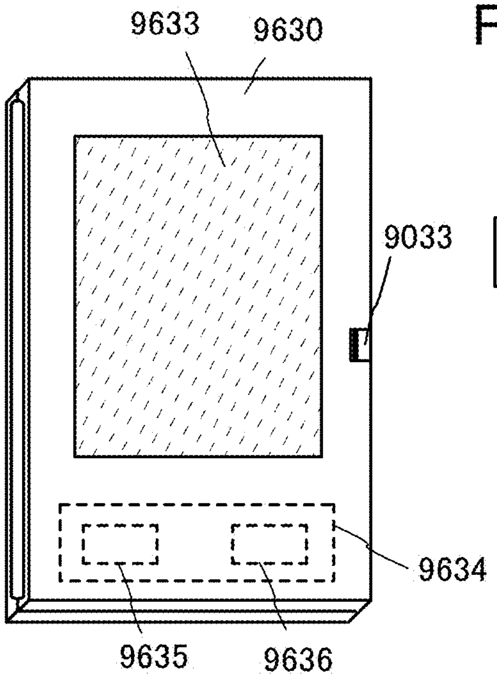

FIGS. 12A and 12B illustrate an example of a foldable tablet terminal. FIG. 12A illustrates the tablet terminal which is unfolded. The tablet terminal includes a housing 9630, a display portion 9631*a*, a display portion 9631*b*, a display mode switch 9034, a power switch 9035, a power-saving mode switch 9036, a clasp 9033, and an operation switch 9038. Note that in the tablet terminal, one or both of the display portion 9631*a* and the display portion 9631*b* is/are formed using a light-emitting device which includes a light-emitting element including the above compound.

Part of the display portion 9631*a* can be a touchscreen region 9632*a* and data can be input when a displayed operation key 9637 is touched. Although half of the display portion 9631*a* has only a display function and the other half has a touchscreen function, one embodiment of the present invention is not limited to the structure. The whole display portion 9631*a* may have a touchscreen function. For example, a keyboard is displayed on the entire region of the display portion 9631*a* so that the display portion 9631*a* is used as a touchscreen; thus, the display portion 9631*b* can be used as a display screen.

Like the display portion 9631*a*, part of the display portion 9631*b* can be a touchscreen region 9632*b*. When a keyboard display switching button 9639 displayed on the touchscreen is touched with a finger, a stylus, or the like, the keyboard can be displayed on the display portion 9631*b*.

Touch input can be performed in the touchscreen region 9632*a* and the touchscreen region 9632*b* at the same time.

The display mode switch 9034 can switch the display between portrait mode, landscape mode, and the like, and between monochrome display and color display, for example. The power-saving switch 9036 can control display luminance in accordance with the amount of external light in use of the tablet terminal detected by an optical sensor incorporated in the tablet terminal. Another detection device including a sensor for detecting inclination, such as a gyroscope or an acceleration sensor, may be incorporated in the tablet terminal, in addition to the optical sensor.

Although FIG. 12A illustrates an example in which the display portion 9631*a* and the display portion 9631*b* have the same display area, one embodiment of the present invention is not limited to the example. The display portion 9631*a* and the display portion 9631*b* may have different display areas and different display quality. For example, one display panel may be capable of higher-definition display than the other display panel.

FIG. 12B illustrates the tablet terminal which is folded. The tablet terminal includes the housing 9630, a solar cell 9633, a charge and discharge control circuit 9634, a battery 9635, and a DC-to-DC converter 9636. As an example, FIG. 12B illustrates the charge and discharge control circuit 9634 including the battery 9635 and the DC-to-DC converter 9636.

Since the tablet terminal is foldable, the housing 9630 can be closed when the tablet terminal is not in use. As a result, the display portion 9631*a* and the display portion 9631*b* can be protected, thereby providing a tablet terminal with high endurance and high reliability for long-term use.

The tablet terminal illustrated in FIGS. 12A and 12B can have other functions such as a function of displaying various kinds of data (e.g., a still image, a moving image, and a text image), a function of displaying a calendar, a date, the time, or the like on the display portion, a touch-input function operating or editing the data displayed on the display portion by touch input, and a function controlling processing by various kinds of software (programs).

The solar cell 9633 provided on a surface of the tablet terminal can supply power to the touchscreen, the display portion, a video signal processing portion, or the like. Note that the solar cell 9633 is preferably provided on one or two surfaces of the housing 9630, in which case the battery 9635 can be charged efficiently.

Figure 12C:
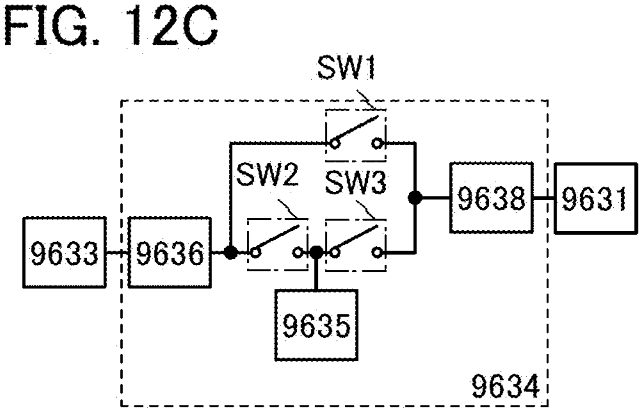

The structure and operation of the charge and discharge control circuit 9634 illustrated in FIG. 12B will be described with reference to a block diagram of FIG. 12C. FIG. 12C illustrates the solar cell 9633, the battery 9635, the DC-to-DC converter 9636, a converter 9638, switches SW1 to SW3, and the display portion 9631. The battery 9635, the DC-to-DC converter 9636, the converter 9638, and the switches SW1 to SW3 correspond to the charge and discharge control circuit 9634 illustrated in FIG. 12B.

First, description is made on an example of the operation in the case where power is generated by the solar cell 9633 with the use of external light. The voltage of the power generated by the solar cell is raised or lowered by the DC-to-DC converter 9636 so as to be voltage for charging the battery 9635. Then, when power supplied from the battery 9635 charged by the solar cell 9633 is used for the operation of the display portion 9631, the switch SW1 is turned on and the voltage of the power is raised or lowered by the converter 9638 so as to be voltage needed for the display portion 9631. When images are not displayed on the display portion 9631, the switch SW1 is turned off and the switch SW2 is turned on so that the battery 9635 is charged.

Although the solar cell 9633 is described as an example of a power generation unit, the power generation unit is not particularly limited, and the battery 9635 may be charged by another power generation unit such as a piezoelectric element or a thermoelectric conversion element (Peltier element). The battery 9635 may be charged by a non-contact power transmission module which is capable of charging by transmitting and receiving power by wireless (without contact), or another charge unit used in combination, and the power generation unit is not necessarily provided.

Needless to say, one embodiment of the present invention is not limited to the electronic device having the shape illustrated in FIGS. 12A to 12C as long as the display portion 9631 is included.

EXAMPLE 1

Synthesis Example 1

In this synthesis example, a method for synthesizing 4-[3'-(dibenzothiophen-4-yl)biphenyl-3-yl]benzofuro[3,2-d]pyrimidine (abbreviation: 4mDBTBPBfpm-II) that is a compound having a benzofuropyrimidine skeleton and represented by Structural Formula (100) in Embodiment 1 will be described. The structural formula of 4mDBTBPBfpm-II is shown below.

(100)

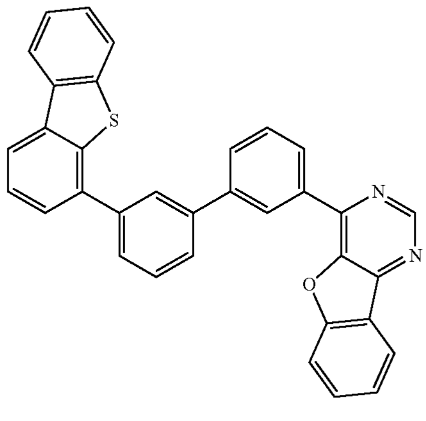

Step 1: Synthesis of 4-(3'-Bromobiphenyl-3-yl)dibenzothiophene

First, 48 g of 3-(dibenzothiophen-4-yl)phenylboronic acid, 54 g of 3-iodobromobenzene, 1.9 g of tris(2-methylphenyl)phosphine (abbreviation: P(o-tolyl)$_3$), 160 mL of a 2M aqueous solution of potassium carbonate, 800 mL of toluene, and 80 mL of ethanol were put in a 3-L three-neck flask equipped with a reflux pipe. The air in the flask was replaced with nitrogen, and heating to 80° C. was performed for dissolution. To this mixed solution, 0.38 g of palladium (II) acetate was added and stirring was performed for 8 hours. Then, 0.92 g of tris(2-methylphenyl)phosphine and 0.18 g of palladium(II) acetate were further added and stirring was performed for 6 hours. After that, water was added to this solution and extraction with toluene was performed to obtain an organic layer. The organic layer was dried over magnesium sulfate, and the dried solution was filtered. The solvent in this solution was distilled off, and the resulting residue was dissolved in hot toluene. The hot toluene solution was subjected to hot filtration through a filter aid in which Celite (Catalog No. 531-16855, manufactured by Wako Pure Chemical Industries, Ltd. (the same applies to Celite in the following description)), alumina, Florisil (Catalog No. 540-00135, manufactured by Wako Pure Chemical Industries, Ltd. (the same applies to Florisil in the following description)), and Celite were stacked in this order. The solvent was distilled off and the resulting solid was recrystallized from a mixed solvent of toluene and methanol, so that a white solid was obtained in a yield of 34%. Synthesis Scheme (a-1) of Step 1 is shown below.

(a-1)

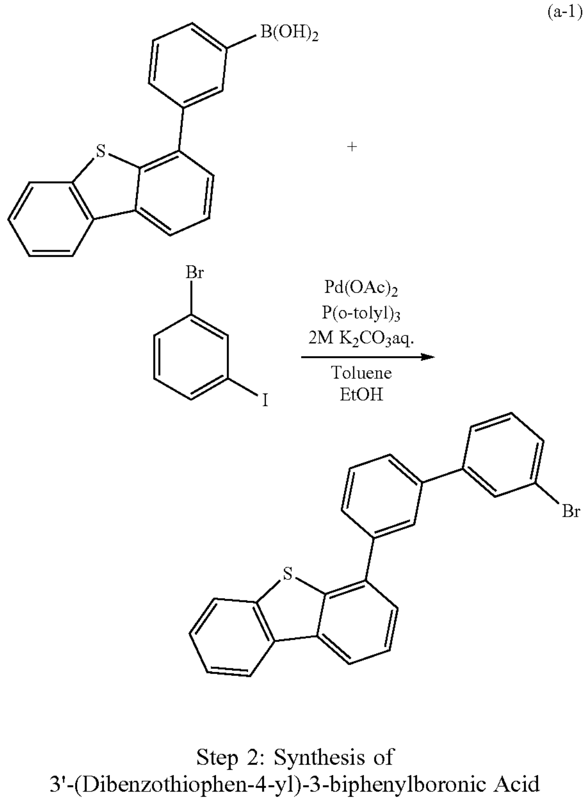

Step 2: Synthesis of 3'-(Dibenzothiophen-4-yl)-3-biphenylboronic Acid

In a 1-L three-neck flask equipped with a dropping funnel was put 30 g of 4-(3'-bromobiphenyl-3-yl)dibenzothiophene obtained in Step 1, and the air in the flask was replaced with nitrogen. To the flask, 300 mL of tetrahydrofuran (dehydrated) was added, and the flask was cooled down to −78° C. in a cryostat. After that, 50 mL of a 1.6 M hexane solution of n-butyl lithium was dropped with a dropping funnel, and 64 mL of tetrahydrofuran (dehydrated) was put in the dropping funnel to be poured into the reacted solution, which was then stirred at −78° C. for 1 hour. Then, 11 mL of trimethyl borate was dropped and the temperature was raised to room temperature, at which stirring was performed for 18 hours. To this solution, 48 mL of 1 M hydrochloric acid was added and stirring was performed for 1 hour. Water was added into the resulting mixture, and extraction with ethyl acetate was performed to give an organic layer. The organic layer was washed with water and a saturated aqueous solution of sodium chloride, and dried over magnesium sulfate. The solution obtained by the drying was filtered. The solvent in this solution was distilled off, and the resulting solid was washed with toluene; thus, a white solid was obtained in a yield of 40%. Synthesis Scheme (b-1) of Step 2 is shown below.

(b-1)

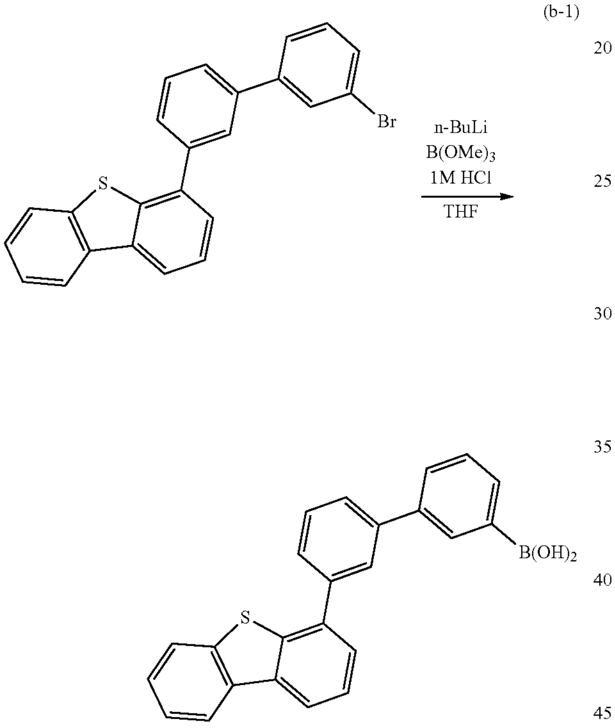

Step 3: Synthesis of 4-[3'-(Dibenzothiophen-4-yl)biphenyl-3-yl]benzofuro[3,2-d]pyrimidine (abbreviation: 4mDBTBPBfpm-II)

Into a 100-mL three-neck flask equipped with a reflux pipe were put 2.3 g of 3'-(dibenzothiophen-4-yl)-3-biphenylboronic acid obtained in Step 2, 1.2 g of 4-chlorobenzofuro[3,2-d]pyrimidine, 5.4 mL of a 2 M aqueous solution of potassium carbonate, 27 mL of toluene, and 2.7 mL of ethanol. Degasification by stirring under a reduced pressure was performed and the air in the flask was replaced with nitrogen. To this mixture, 68 mg of tetrakis(triphenylphosphine)palladium(0) (abbreviation: $Pd(PPh_3)_4$) was added and the mixture was heated at 80° C. for 2 hours to cause a reaction. The resulting mixture was washed with water and ethanol and recrystallized from toluene, so that 1.8 g of a white solid was obtained in a yield of 60%. Synthesis Scheme (c-1) of Step 3 is shown below.

(c-1)

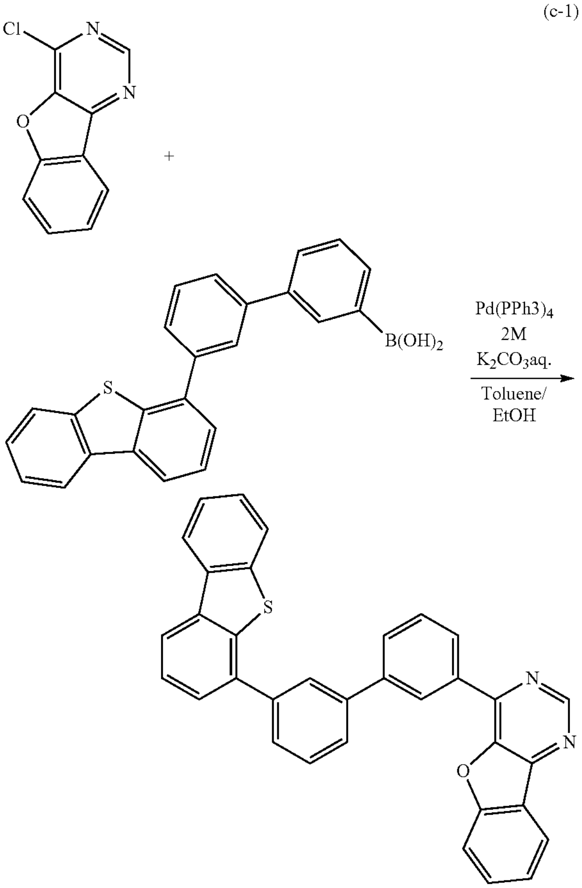

By a train sublimation method, 2.3 g of the white solid was purified by sublimation. The sublimation purification was conducted under the conditions where the pressure was 3.2 Pa, the flow rate of an argon gas was 15 mL/min, and the solid was heated at 235° C. After the sublimation purification, 0.5 g of a white solid which was a target substance was obtained at a collection rate of 22%.

By a train sublimation method, 1.5 g of a solid that was not purified by the previous sublimation purification was subject to sublimation purification. The sublimation purification was conducted under the conditions where the pressure was 2.7 Pa, the flow rate of an argon gas was 5.0 mL/min, and the heating temperature was 245° C. After the sublimation purification, 1.4 g of a white solid which was a target substance was obtained at a collection rate of 92%.

Analysis results by nuclear magnetic resonance ($^1H$-NMR) spectroscopy of the white solid obtained in Step 3 are described below. The results revealed that 4mDBTBPBfpm-II was obtained.

$^1H$-NMR. δ($CDCl_3$): 7.44-7.54 (m, 4H), 7.60-7.61 (m, 2H), 7.66-7.51 (m, 4H), 7.78-7.84 (m, 2H), 7.91-7.92 (d, 1H), 8.17 (ts, 1H), 8.20-8.23 (m, 2H), 8.31-8.32 (d, 1H), 8.62-8.63 (d, 1H), 8.96-8.97 (t, 1H), 9.30 (s, 1H).

Figure 13A:
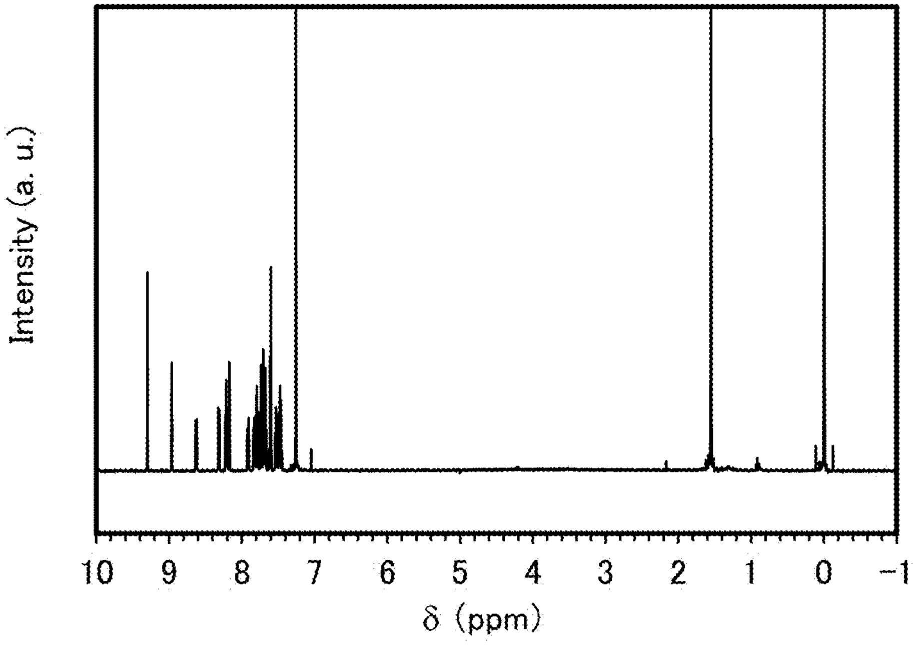
FIGS. 13A and 13B are NMR charts of 4mDBTBPBfpm-II.
Figure 13B:
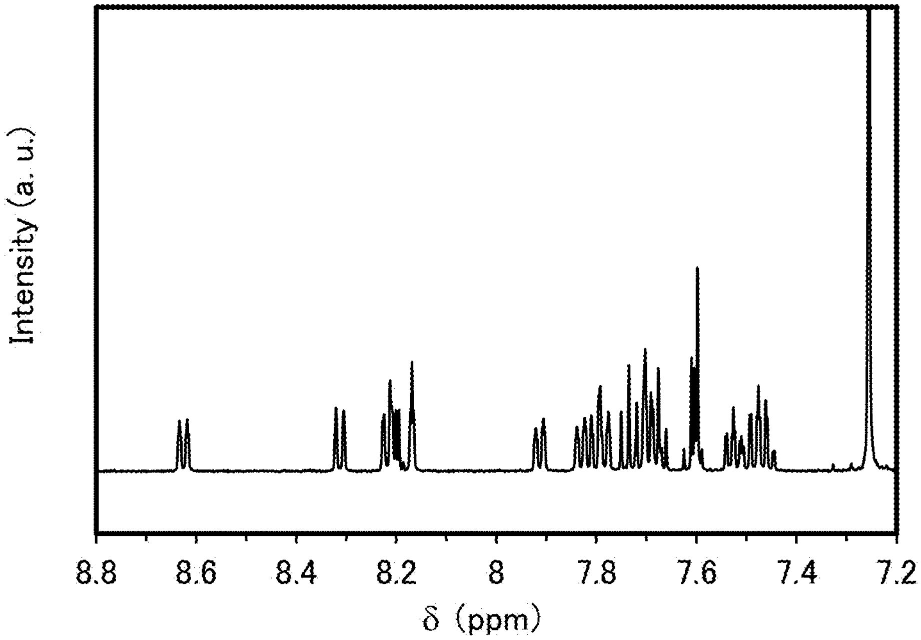

FIGS. 13A and 13B are $^1H$ NMR charts. Note that FIG. 13B shows an enlarged part of FIG. 13A in the range of 7.2 ppm to 8.8 ppm. The measurement results reveal that 4mDBTBPBfpm-II, which was the target substance, was obtained.

<<Physical Properties of 4mDBTBPBfpm-II>

Figure 14A:
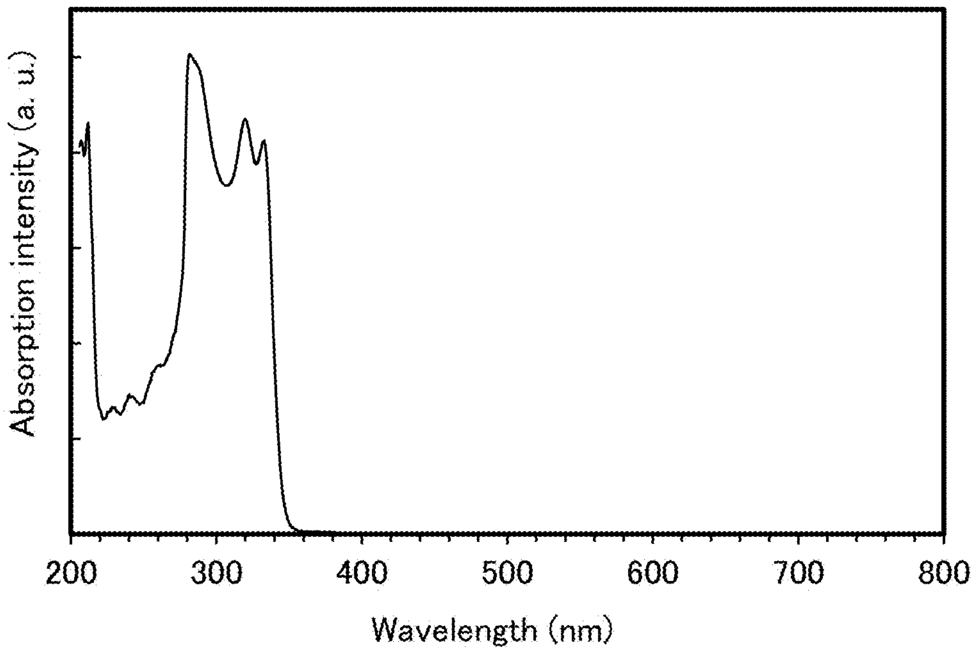
FIGS. 14A and 14B show an absorption spectrum and an emission spectrum of 4mDBTBPBfpm-II.
Figure 14B:
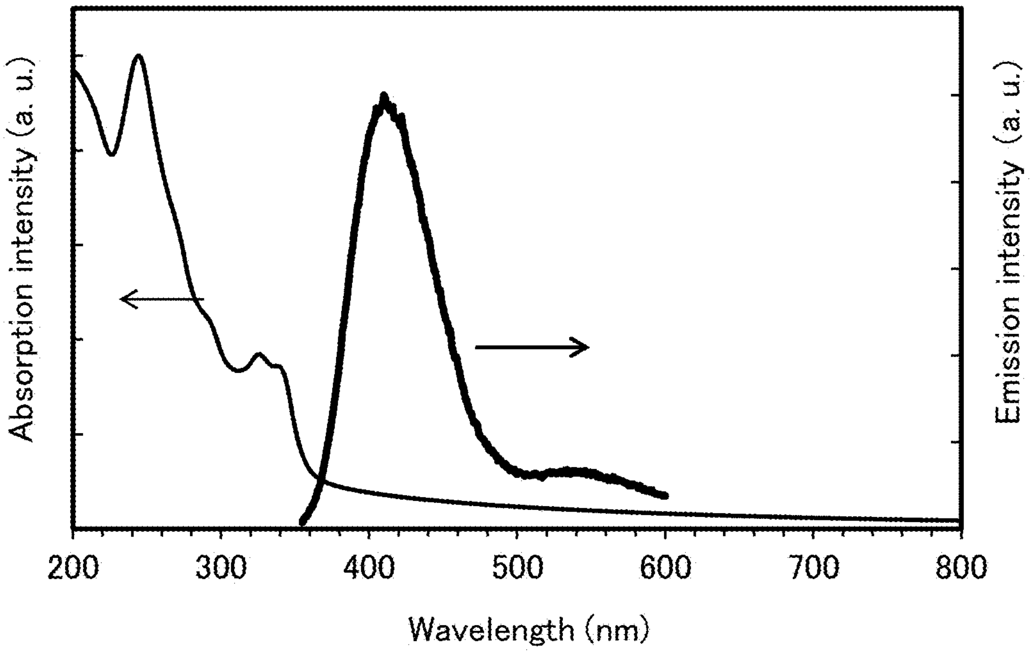

FIG. 14A shows an absorption spectrum and an emission spectrum of 4mDBTBPBfpm-II in a toluene solution of 4mDBTBPBfpm-II, and FIG. 14B shows an absorption spectrum and an emission spectrum of a thin film of 4mDBTBPBfpm-II. The spectra were measured with a UV-visible spectrophotometer (V550, produced by JASCO Corporation). The spectra of 4mDBTBPBfpm-II in the toluene solution of 4mDBTBPBfpm-II were measured with a toluene solution of 4mDBTBPBfpm-II put in a quartz cell. The spectra of the thin film were measured with a sample prepared by deposition of 4mDBTBPBfpm-II on a quartz substrate by evaporation. Note that in the case of the absorption spectrum of 4mDBTBPBfpm-II in the toluene solution of 4mDBTBPBfpm-II, the absorption spectrum obtained by subtraction of the absorption spectra of quartz and toluene from the measured spectra is shown in the drawing and that in the case of the absorption spectrum of the thin film of 4mDBTBPBfpm-II, the absorption spectrum obtained by subtraction of the absorption spectrum of the quartz substrate from the measured spectra is shown in the drawing.

As shown in FIG. 14A, in the case of 4mDBTBPBfpm-II in the toluene solution, absorption peaks were observed at approximately 282 nm and 320 nm. As shown in FIG. 14B, in the case of the thin film of 4mDBTBPBfpm-II, absorption peaks were observed at approximately 244 nm, 268 nm, 290 nm, 326 nm, and 340 nm, and an emission wavelength peak was observed at 410 nm (excitation wavelength: 340 nm). Thus, it was found that absorption and light emission of 4mDBTBPBfpm-II occur in extremely short wavelength regions.

The ionization potential of 4mDBTBPBfpm-II in a thin film state was measured by a photoelectron spectrometer (AC-2, manufactured by Riken Keiki, Co., Ltd.) in the air. The obtained value of the ionization potential was converted into a negative value, so that the HOMO level of 4mDBTBPBfpm-II was −6.38 eV. From the data of the absorption spectrum of the thin film in FIG. 14B, the absorption edge of 4mDBTBPBfpm-II, which was obtained from Tauc plot with an assumption of direct transition, was 3.50 eV. Therefore, the optical energy gap of 4mDBTBPBfpm-II in a solid state was estimated at 3.50 eV; from the values of the HOMO level obtained above and this energy gap, the LUMO level of 4mDBTBPBfpm-II was estimated at −2.88 eV. This reveals that 4mDBTBPBfpm-II in the solid state has an energy gap as wide as 3.50 eV.

Furthermore, 4mDBTBPBfpm-II was analyzed by liquid chromatography mass spectrometry (LC/MS).

The analysis by LC/MS was carried out with Acquity UPLC (produced by Waters Corporation) and Xevo G2 Tof MS (produced by Waters Corporation).

In the MS analysis, ionization was carried out by an electrospray ionization (ESI) method. Capillary voltage and sample cone voltage were set to 3.0 kV and 30 V, respectively. Detection was performed in a positive mode. A component which underwent the ionization under the above-mentioned conditions was collided with an argon gas in a collision cell to dissociate into product ions. Energy (collision energy) for the collision with argon was 50 eV and 70 eV. A mass range for the measurement was m/z=100 to 1200.

Figure 15A:
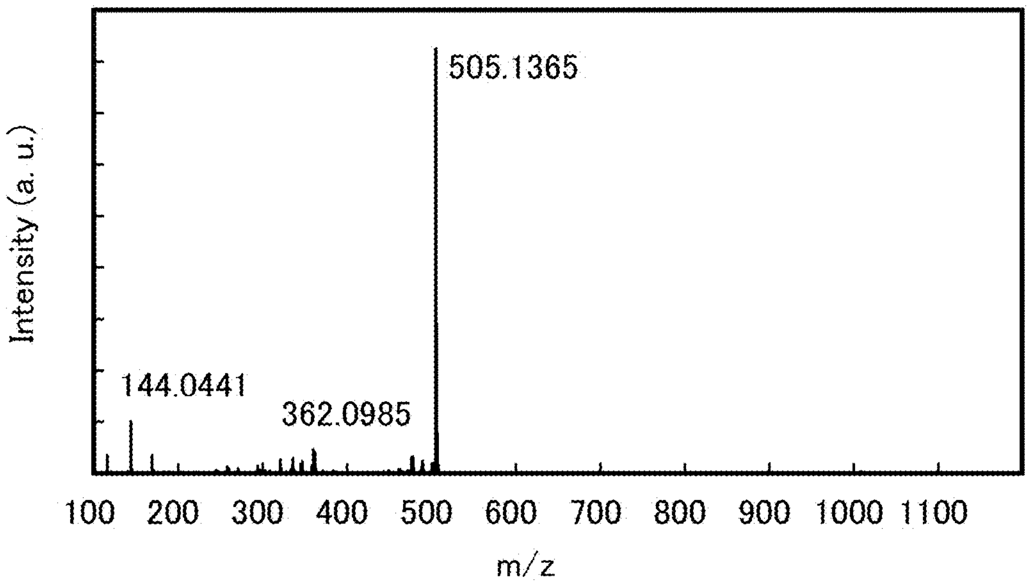
FIGS. 15A and 15B show results of LC/MS analysis of 4mDBTBPBfpm-II.
Figure 15B:
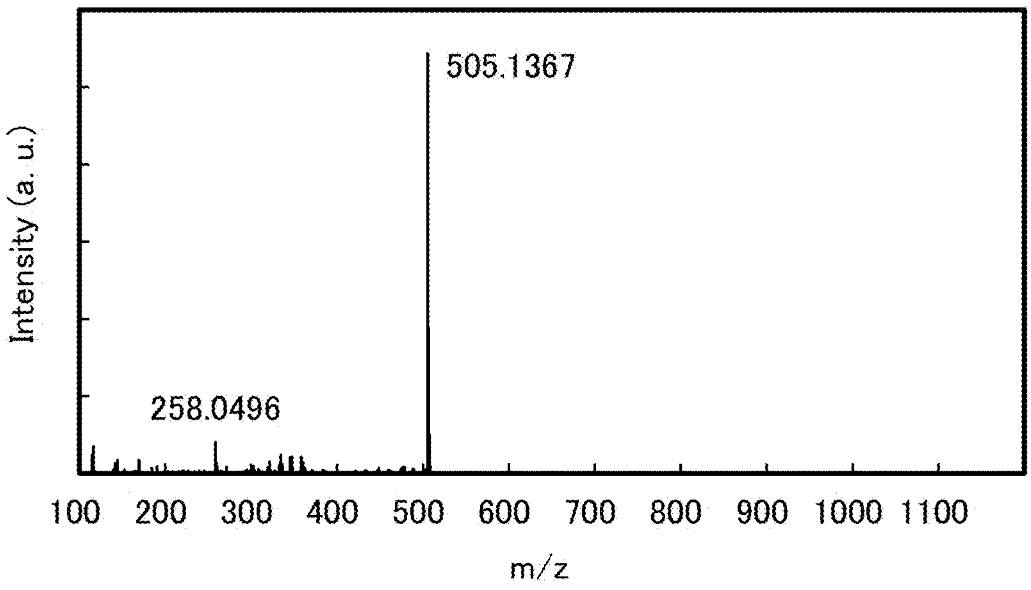

FIGS. 15A and 15B show the results. FIG. 15A shows the results at the time when the collision energy was 50 eV FIG. 15B shows the results at the time when the collision energy was 70 eV.

EXAMPLE 2

Synthesis Example 2

In this synthesis example, a synthesis example of 4-{3-[3'-(9H-carbazol-9-yl)]biphenyl-3-yl}benzofuro[3,2-d]pyrimidine (abbreviation: 4mCzBPBfpm) that is a compound having a benzofuropyrimidine skeleton and represented by Structural Formula (300) in Embodiment 1 will be specifically described. The structural formula of 4mCzBPBfpm is shown below.

(300)

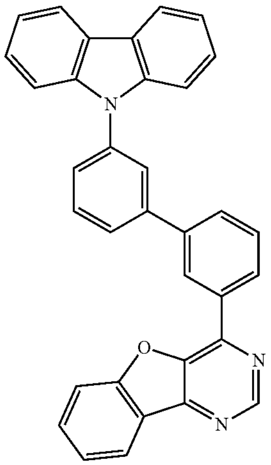

Step 1: Synthesis of 9-[3-(3-Bromophenyl)phenyl]-9H-carbazole

First, 16 g (56 mmol) of 3-(9H-carbazol-9-yl)phenylboronic acid, 19 g (67 mmol) of 3-iodobromobenzene, 0.68 g (2.2 mmol) of tri(ortho-tolyl)phosphine, 56 mL of a 2 M aqueous solution of potassium carbonate, 250 mL of toluene, and 30 mL of ethanol were put into a 1-L three-neck flask, and the air in the flask was replaced with nitrogen. To this mixture was added 0.13 g (0.56 mmol) of palladium acetate, and the mixture was heated and stirred at 80° C. for 14 hours. The aqueous layer of the obtained reaction mixture was subjected to extraction with toluene, and the resulting solution of the extract and the organic layer were combined and washed with water and a saturated aqueous solution of sodium chloride. Magnesium sulfate was added to the organic layer for drying, and the resulting mixture was subjected to gravity filtration to give a filtrate. This filtrate was concentrated to give an oily substance. The oily substance was purified by recycling preparative HPLC using LC-SakuraNEXT. The resulting fraction was concentrated and washed with toluene and methanol; thus, 9-[3-(3-bromophenyl)phenyl]-9H-carbazole was obtained as 13 g of a white solid in a yield of 58%. Synthesis Scheme (a-2) of Step 1 is shown below.

(a-2)

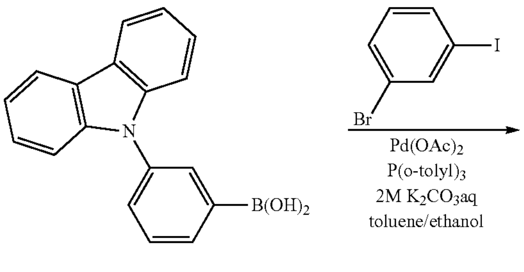

-continued

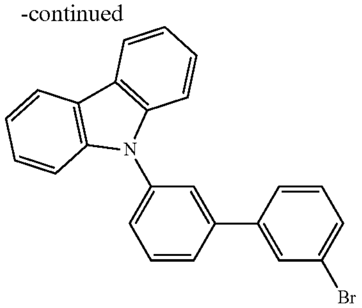

Step 2: Synthesis of 3-[3'-(9H-Carbazol-9-yl)]biphenylboronic Acid

In a 500-mL three-neck flask was put 13 g (33 mmol) of 9-[3-(3-bromophenyl)phenyl]-9H-carbazole, the flask was degassed, and the air in the flask was replaced with nitrogen. Then, 160 mL of tetrahydrofuran was added and stirring was performed at −78° C. To this mixed solvent, 24 mL (40 mmol) of n-butyl lithium (1.65 mol/L hexane solution) was dropped and stirring was performed at −78° C. for 1 hour. After the predetermined time elapsed, 4.7 mL (43 mmol) of trimethyl borate was added to this mixed solution, and stirring was performed for 18 hours while the temperature was raised to 20° C. After the predetermined time elapsed, 100 mL of 1 mol/L hydrochloric acid was added to the reacted solution, and stirring was performed at room temperature for 30 minutes. The aqueous layer of this mixture was subjected to extraction with ethyl acetate, and the resulting solution of the extract was washed with a saturated aqueous solution of sodium chloride. Anhydrous magnesium sulfate was added to the organic layer for drying, and the resulting mixture was subjected to gravity filtration. The filtrate was concentrated to give a solid. This solid was washed with toluene, so that 3-[3'-(9H-carbazol-9-yl)]biphenylboronic acid was obtained as 6.0 g of a white solid in a yield of 51%. Synthesis Scheme (b-2) of Step 2 is shown below.

(b-2)

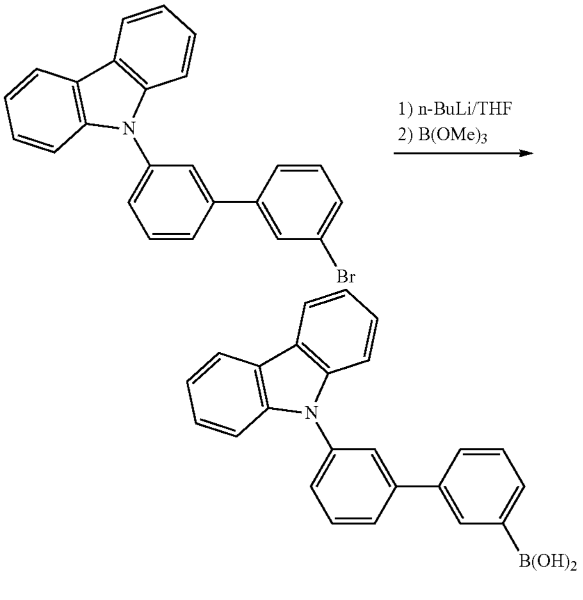

Step 3: Synthesis of 4-{3-[3'-(9H-Carbazol-9-yl)]biphenyl-3-yl}benzofuro[3,2-d]pyrimidine (abbreviation: 4mCzBPBfpm)

In a 200-mL three-neck flask were put 3.0 g (8.3 mmol) of 3-[3'-(9H-carbazol-9-yl)]biphenylboronic acid, 1.7 g (8.3 mmol) of 4-chlorobenzofuro[3,2-d]pyrimidine, 8.3 mL of a 2 M aqueous solution of potassium carbonate, 40 mL of toluene, and 4 mL of ethanol, and the air in the flask was replaced with nitrogen. To this mixture was added 68.3 mg (0.059 mmol) of bis(triphenylphosphine)palladium(II) dichloride ($Pd(PPh_3)_2Cl_2$), and the mixture was heated and stirred at 80° C. for 6 hours. The aqueous layer of the obtained reaction solution was subjected to extraction with toluene, and the resulting solution of the extract and the organic layer were combined and washed with a saturated aqueous solution of sodium chloride. Anhydrous magnesium sulfate was added to the organic layer for drying, and the resulting mixture was subjected to gravity filtration to give a filtrate. The filtrate was concentrated to give a solid. The solid was dissolved in toluene and this solution was filtered through Celite, alumina, and Celite. The filtrate was concentrated to give a solid. The solid was recrystallized from toluene, so that 2.0 g of a white solid was obtained in a yield of 50%. Then, 2.0 g of the white solid was purified by sublimation using a train sublimation method. The sublimation purification was conducted under the conditions where the pressure was 2.3 Pa, the flow rate of an argon gas was 10 mL/min, and the solid was heated at 250° C. After the sublimation purification, 1.3 g of a white solid which was a target substance was obtained at a collection rate of 65%. Synthesis Scheme (c-2) of Step 2 is shown below.

(c-2)

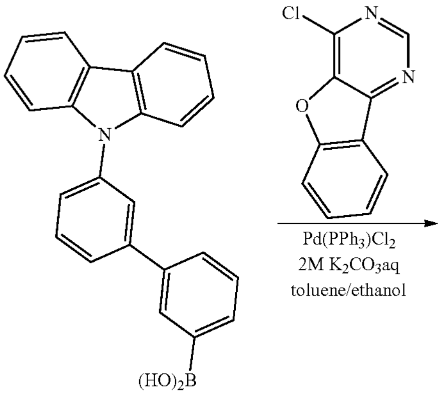

-continued

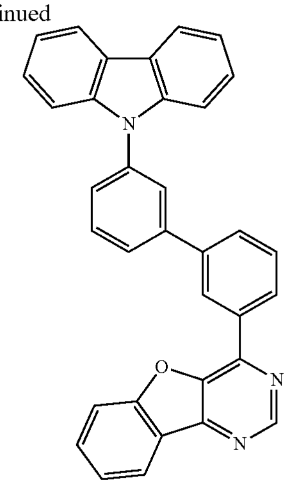

Analysis results by nuclear magnetic resonance ($^1$H-NMR) spectroscopy of the white solid obtained in Step 3 are described below.

$^1$H-NMR. δ($CDCl_3$): 7.32 (m, 2H), 7.44 (m, 2H), 7.52-7.55 (m, 3H), 7.63-7.64 (m, 1H), 7.69-7.77 (m, 4H), 7.85-7.88 (m, 2H), 7.97 (t, 1H), 8.18 (d, 2H), 8.31 (d, 1H), 8.65 (m, 1H), 8.92 (t, 1H), 9.27 (s, 1H).

Figure 16A:
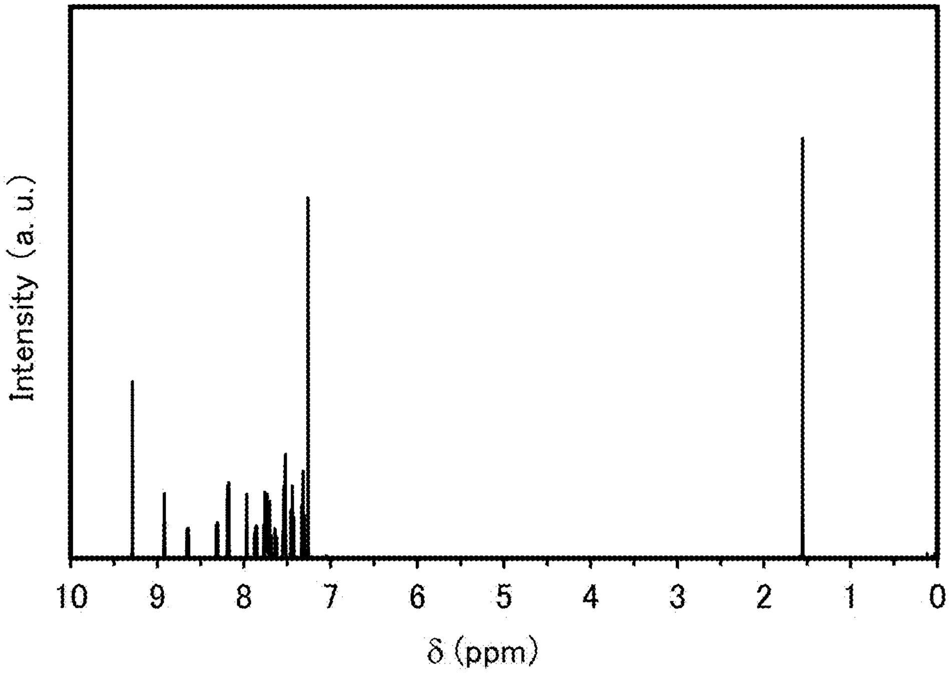
FIGS. 16A and 16B are NMR charts of 4mCzBPBfpm.
Figure 16B:
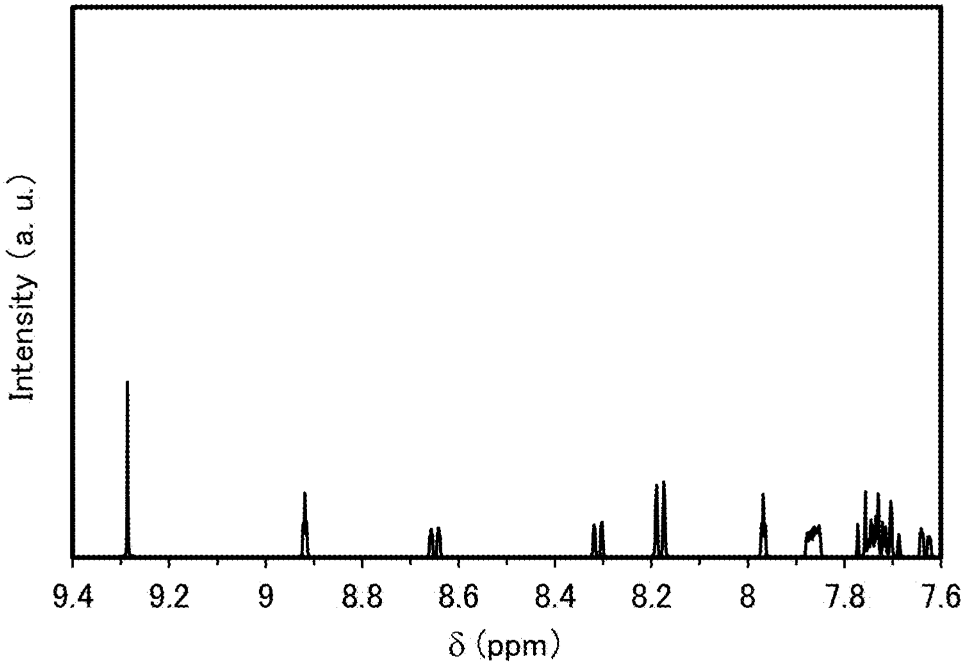

FIGS. 16A and 16B are $^1$H NMR charts. Note that FIG. 16B shows an enlarged part of FIG. 16A in the range of 7.6 ppm to 9.4 ppm. The measurement results reveal that 4mCzBPBfpm, which was the target substance, was obtained.

<<Physical Properties of 4mCzBPBfpm>>

Figure 17A:
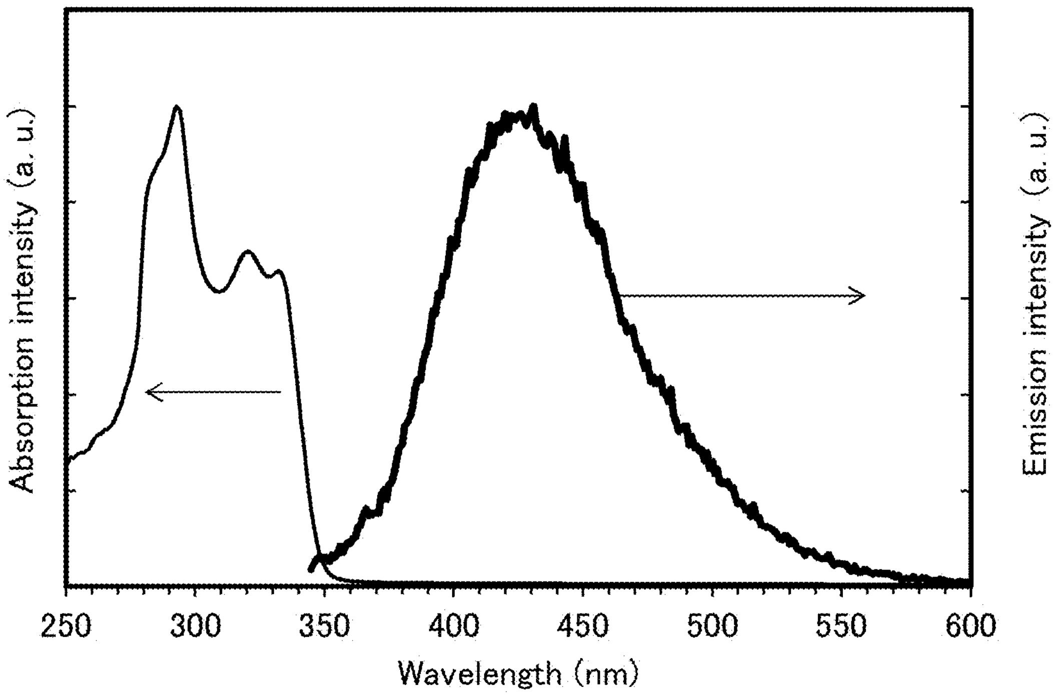
FIGS. 17A and 17B show an absorption spectrum and an emission spectrum of 4mCzBPBfpm.
Figure 17B:
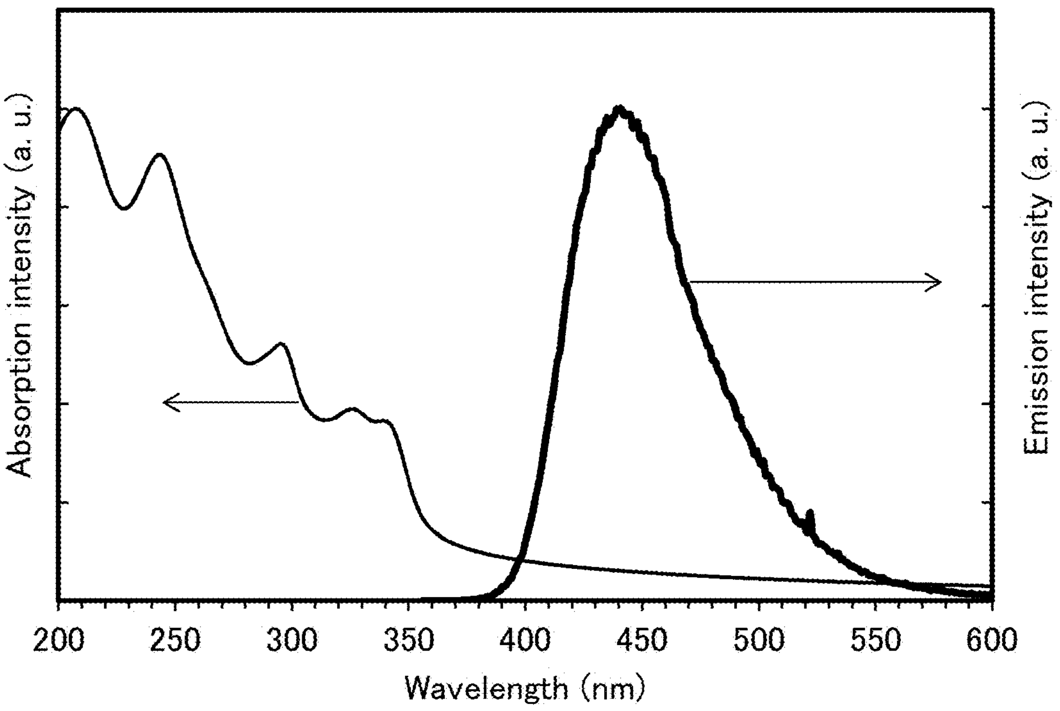

FIG. 17A shows an absorption spectrum and an emission spectrum of 4mCzBPBfpm in a toluene solution of 4mCzBPBfpm, and FIG. 17B shows an absorption spectrum and an emission spectrum of a thin film of 4mCzBPBfpm. The spectra were measured with a UV-visible spectrophotometer (V550, produced by JASCO Corporation). The spectra of 4mCzBPBfpm in the toluene solution of 4mCzBPBfpm were measured with a toluene solution of 4mCzBPBfpm put in a quartz cell. The spectra of the thin film were measured with a sample prepared by deposition of 4mCzBPBfpm on a quartz substrate by evaporation. Note that in the case of the absorption spectrum of 4mCzBPBfpm in the toluene solution of 4mCzBPBfpm, the absorption spectrum obtained by subtraction of the absorption spectra of quartz and toluene from the measured spectra is shown in the drawing and that in the case of the absorption spectrum of the thin film of 4mCzBPBfpm, the absorption spectrum obtained by subtraction of the absorption spectrum of the quartz substrate from the measured spectra is shown in the drawing.

As shown in FIG. 17A, in the case of 4mCzBPBfpm in the toluene solution, absorption peaks were observed at approximately 294 nm, 324 nm and 334 nm, and the peak of the emission wavelength was at 422 nm (at an excitation wavelength of 330 nm). As shown in FIG. 17B, in the case of the thin film of 4mCzBPBfpm, absorption peaks were observed at approximately 207 nm, 243 nm, 262 nm, 289 nm, 295 nm, 326 nm, and 341 nm and an emission wavelength peak was observed at 440 nm (excitation wavelength: 341 nm). Thus, it was found that absorption and light emission of 4mCzBPBfpm occur in extremely short wavelength regions.

The ionization potential of 4mCzBPBfpm in a thin film state was measured by a photoelectron spectrometer (AC-2, manufactured by Riken Keiki, Co., Ltd.) in the air. The obtained value of the ionization potential was converted into a negative value, so that the HOMO level of 4mCzBPBfpm was −6.13 eV. From the data of the absorption spectrum of the thin film in FIG. 17B, the absorption edge of 4mCzBPBfpm, which was obtained from Tauc plot with an assumption of direct transition, was 3.49 eV. Therefore, the optical energy gap of 4mCzBPBfpm in a solid state was estimated at 3.49 eV; from the values of the HOMO level obtained above and this energy gap, the LUMO level of 4mCzBPBfpm was estimated at −2.64 eV. This reveals that 4mCzBPBfpm in the solid state has an energy gap as wide as 3.49 eV.

Furthermore, 4mCzBPBfpm was analyzed by liquid chromatography mass spectrometry (LC/MS).

The analysis by LC/MS was carried out with Acquity UPLC (produced by Waters Corporation) and Xevo G2 Tof MS (produced by Waters Corporation).

In the MS analysis, ionization was carried out by an electrospray ionization (ESI) method. Capillary voltage and sample cone voltage were set to 3.0 kV and 30 V, respectively. Detection was performed in a positive mode. A component which underwent the ionization under the above-mentioned conditions was collided with an argon gas in a collision cell to dissociate into product ions. Energy (collision energy) for the collision with argon was 50 eV and 70 eV. A mass range for the measurement was m/z=100 to 1200.

Figure 18A:
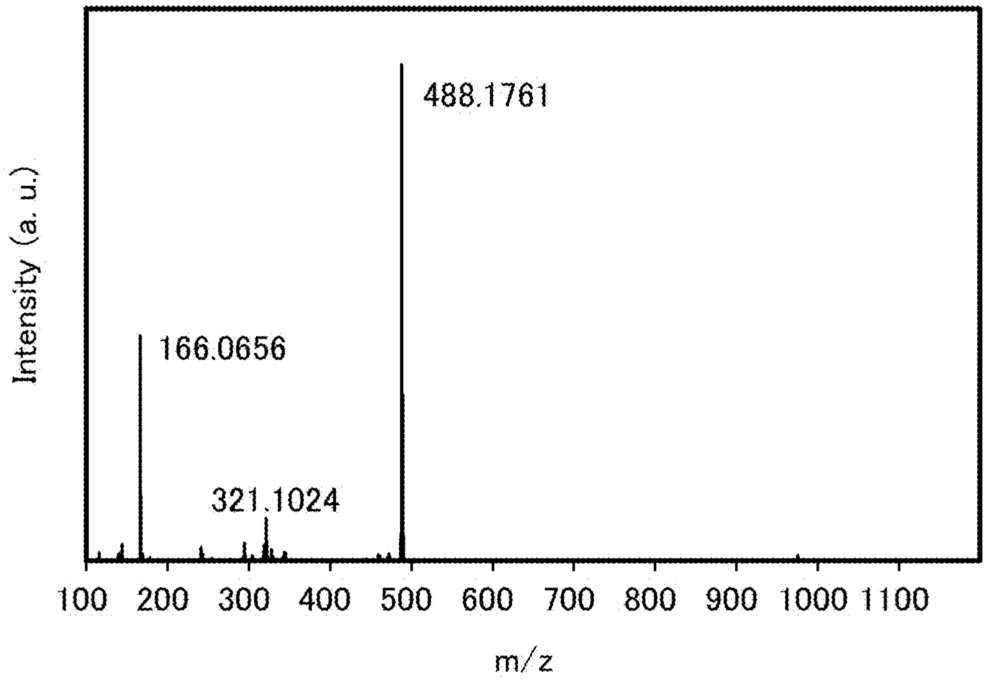
FIGS. 18A and 18B show results of LC/MS analysis of 4mCzBPBfpm.
Figure 18B:
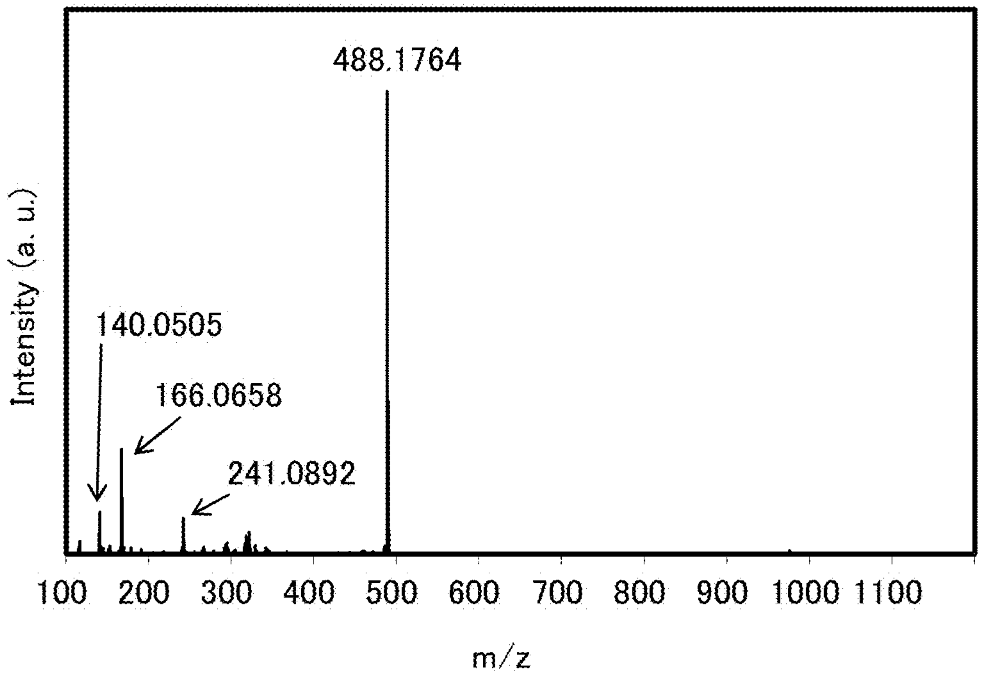

FIGS. 18A and 18B show the results. FIG. 18A shows the results at the time when the collision energy was 50 eV FIG. 18B shows the results at the time when the collision energy was 70 eV.

EXAMPLE 3

This example will explain a light-emitting element (a light-emitting element 1). In the light-emitting element, 4mDBTBPBfpm-II that is the compound having the benzofuropyrimidine skeleton and described in Embodiment 1 was used as a host material in a light-emitting layer that contained a phosphorescent substance emitting green.

The molecular structures of compounds used in this example are shown in Structural Formulae (i) to (v) and (100) below. The element structure in FIG. 1A was employed.

(i)

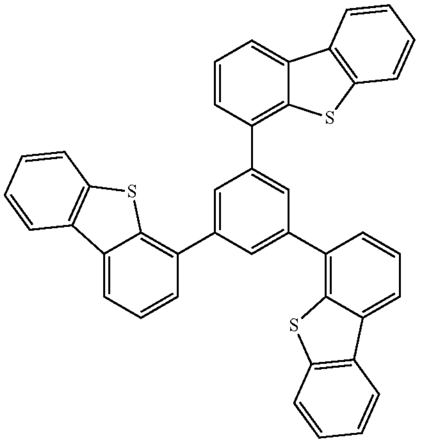

DBT3P-II

-continued (ii)

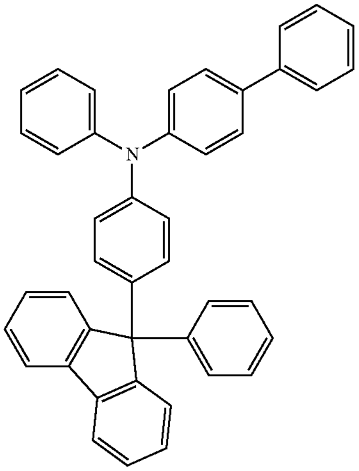

BPAFLP (100)

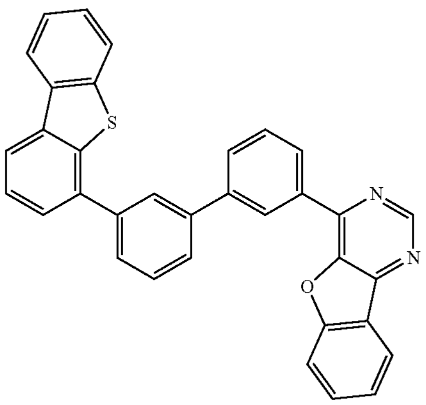

4mDBTBPBfpm-II (iii)

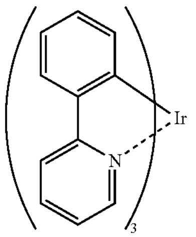

$Ir(ppy)_3$ (iv)

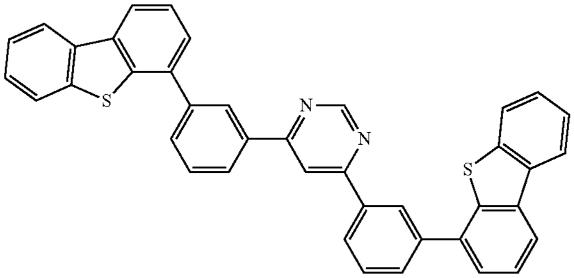

4,6DBTP2Pm-II

-continued (v)

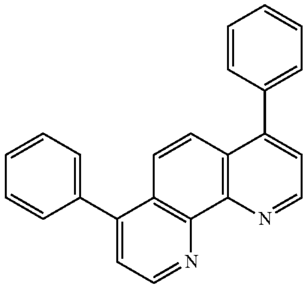

BPhen

<<Fabrication of Light-Emitting Element 1>>

First, a glass substrate, over which a film of indium tin oxide containing silicon (ITSO) was formed to a thickness of 110 nm as the first electrode 101, was prepared. A surface of the ITSO film was covered with a polyimide film so that an area of 2 mm×2 mm of the surface was exposed. As pretreatment for forming the light-emitting element over the substrate, the surface of the substrate was washed with water and baked at 200° C. for 1 hour, and then UV-ozone treatment was performed for 370 seconds. After that, the substrate was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate was cooled down for about 30 minutes.

Then, the substrate was fixed to a holder provided in the vacuum evaporation apparatus so that the surface provided with ITSO faced downward.

The pressure in the vacuum evaporation apparatus was reduced to $10^{-4}$ Pa. Then, 4,4',4"-(benzene-1,3,5-triyl)tri(dibenzothiophene) (abbreviation: DBT3P-II) represented by Structural Formula (i) and molybdenum(VI) oxide were deposited by co-evaporation so that the weight ratio of DBT3P-II to molybdenum oxide was 4:2, whereby the hole-injection layer 111 was formed. The thickness was set to 20 nm. Note that co-evaporation is an evaporation method in which a plurality of different substances are concurrently vaporized from respective different evaporation sources.

Next, 4-phenyl-4'-(9-phenylfluoren-9-yl)triphenylamine (abbreviation: BPAFLP) represented by Structural Formula (ii) was deposited by evaporation to a thickness of 20 nm, whereby the hole-transport layer 112 was formed.

Then, 4-[3'-(dibenzothiophen-4-yl)biphenyl-3-yl]benzofuro[3,2-d]pyrimidine (abbreviation: 4mDBTBPBfpm-II) represented by Structural Formula (100) and tris(2-phenylpyridinato-N,$C^{2'}$)iridium(III) (abbreviation: $[Ir(ppy)_3]$) represented by Structural Formula (iii) were deposited by co-evaporation to a thickness of 20 nm on the hole-transport layer 112 so that the weight ratio of 4mDBTBPBfpm-II to $[Ir(ppy)_3]$ was 1:0.08, and then, 4mDBTBPBfpm-II and $[Ir(ppy)_3]$ were deposited by co-evaporation to a thickness of 20 nm so that the weight ratio of 4mDBTBPBfpm-II to $[Ir(ppy)_3]$ was 1:0.04, whereby the light-emitting layer 113 was formed.

Next, 4,6-bis[3-(4-dibenzothienyl)phenyl]pyrimidine (abbreviation: 4,6mDBTP2Pm-II) represented by Structural Formula (iv) was deposited by evaporation to a thickness of 10 nm, and then bathophenanthroline (abbreviation: BPhen) represented by Structural Formula (v) was deposited by evaporation to a thickness of 15 nm, whereby the electron-transport layer 114 was formed.

Then, lithium fluoride was deposited by evaporation to a thickness of 1 nm on the electron-transport layer 114, whereby the electron-injection layer 115 was formed. Lastly, a film of aluminum was formed to a thickness of 200 nm as the second electrode 102 which serves as a cathode. Thus, the light-emitting element 1 was completed. Note that in all the above evaporation steps, evaporation was performed by a resistance-heating method.

<<Operation Characteristics of Light-Emitting Element 1>>

The light-emitting element 1 obtained as described above was sealed in a glove box containing a nitrogen atmosphere so as not to be exposed to the air. Then, the operating characteristics of the light-emitting element 1 were measured. Note that the measurement was carried out at room temperature (in an atmosphere kept at 25° C.).

Figure 19:
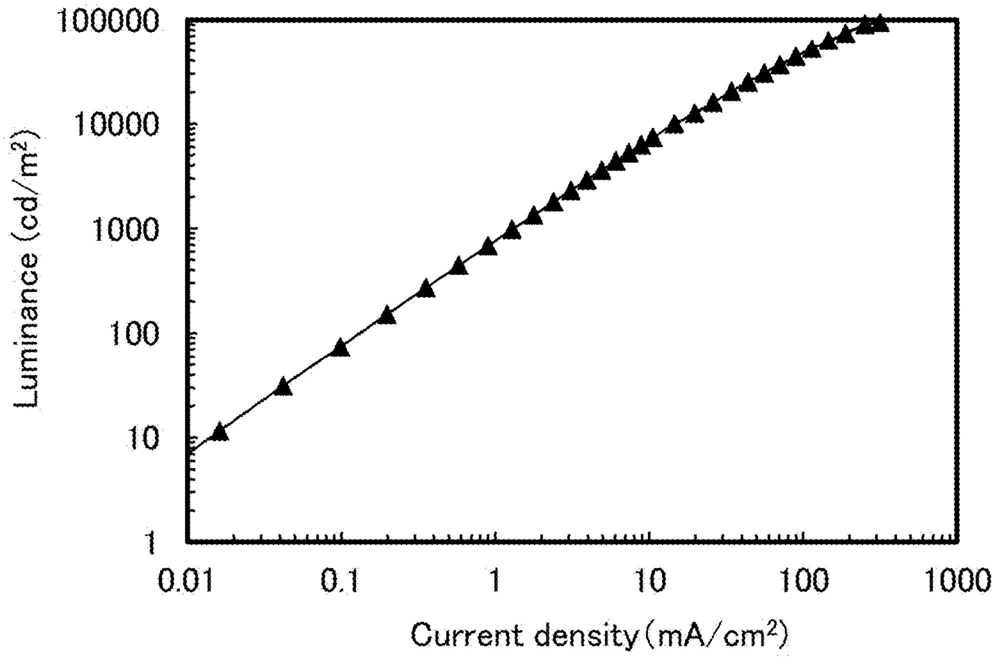
FIG. 19 shows current density-luminance characteristics of a light-emitting element 1.
Figure 20:
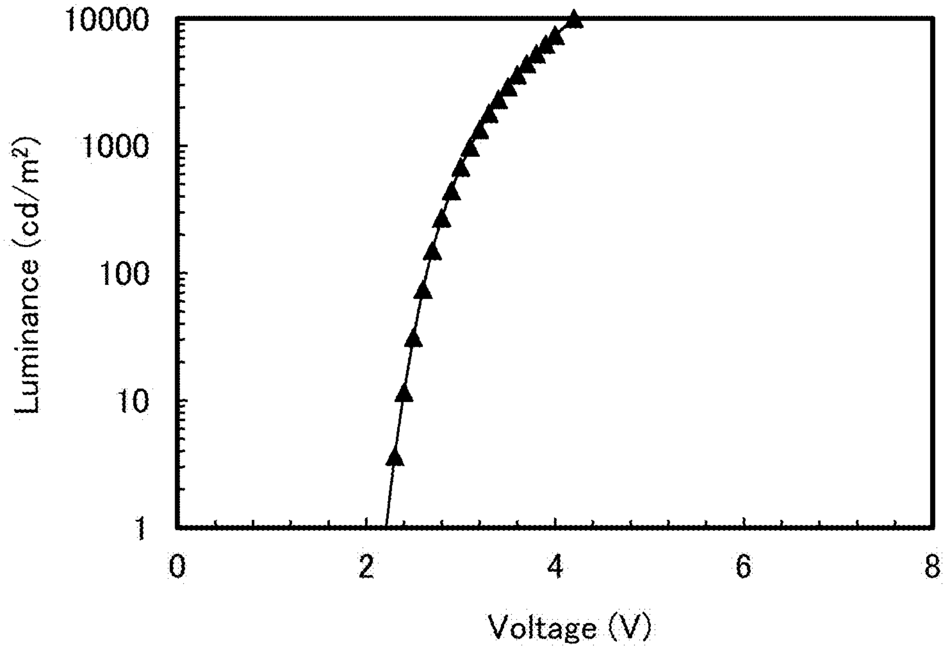
FIG. 20 shows voltage-luminance characteristics of a light-emitting element 1.
Figure 21:
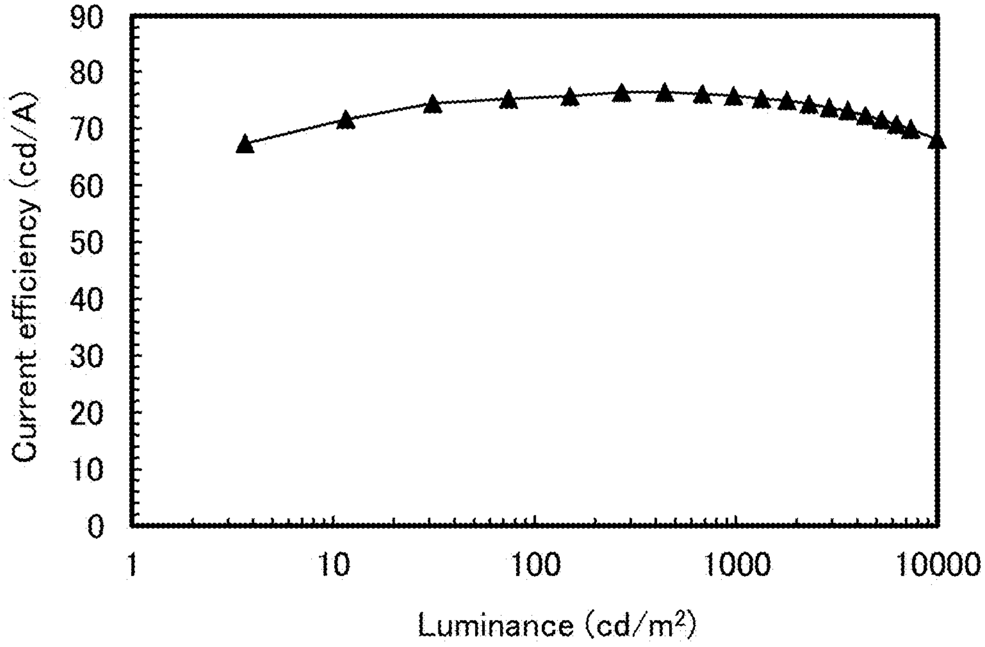
FIG. 21 shows luminance-current efficiency characteristics of a light-emitting element 1.
Figure 22:
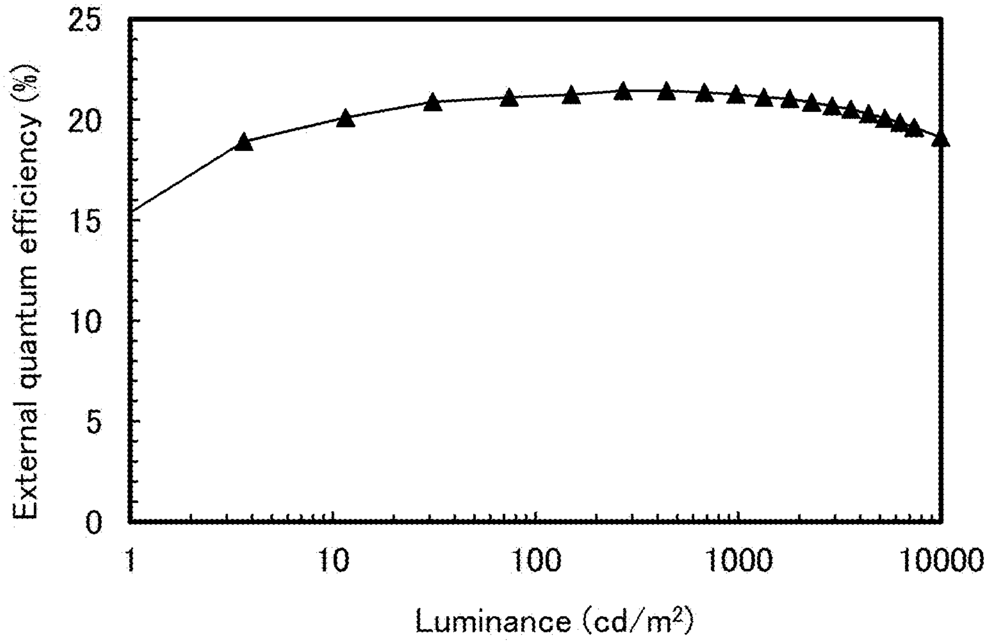
FIG. 22 shows luminance-external quantum efficiency characteristics of a light-emitting element 1.
Figure 23:
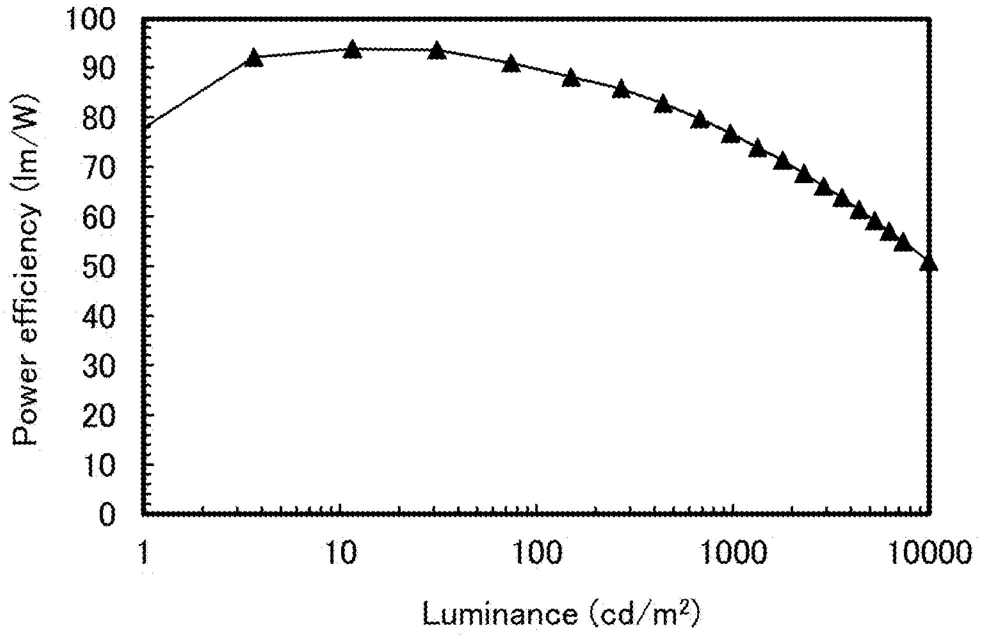
FIG. 23 shows luminance-power efficiency characteristics of a light-emitting element 1.

As to the light-emitting element 1, FIG. 19 shows the current density-luminance characteristics, FIG. 20 shows the voltage-luminance characteristics, FIG. 21 shows the luminance-current efficiency characteristics, FIG. 22 shows the luminance-external quantum efficiency characteristics, and FIG. 23 shows the luminance-power efficiency characteristics.

FIG. 21 shows that the light-emitting element 1 has high luminance-current efficiency characteristics and thus has high emission efficiency. Accordingly, 4mDBTBPBfpm-II, which is the compound having the benzofuropyrimidine skeleton and described in Embodiment 1, has a high triplet excitation level ($T_1$ level) and a wide energy gap, and allows even a phosphorescent substance emitting green to be effectively excited. Moreover, FIG. 20 shows that the light-emitting element 1 has favorable voltage-luminance characteristics and thus has low driving voltage. This means that 4mDBTBPBfpm-II, which is the compound having the benzofuropyrimidine skeleton and described in Embodiment 1, has a high carrier-transport property. FIG. 19 and FIG. 22 also show that the light-emitting element 1 has favorable current density-luminance characteristics and favorable luminance-external quantum efficiency characteristics. Accordingly, the light-emitting element 1 has extremely high power efficiency as shown in FIG. 23.

Figure 24:
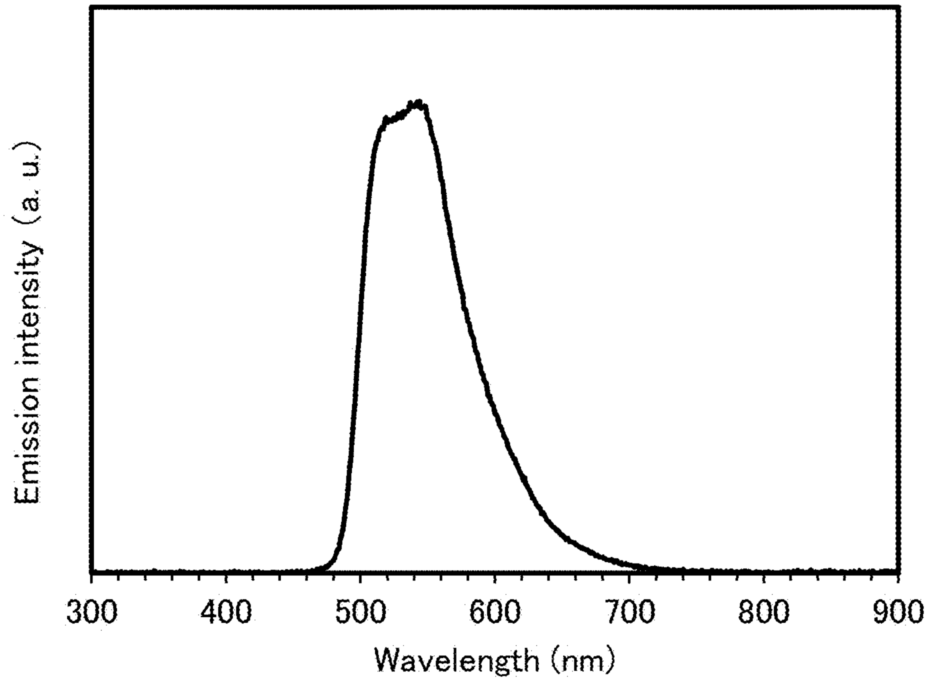
FIG. 24 shows an emission spectrum of a light-emitting element 1.

FIG. 24 shows an emission spectrum at the time when a current of 0.1 mA was made to flow in the fabricated light-emitting element 1. The emission intensity is shown as a value relative to the maximum emission intensity assumed to be 1. FIG. 24 reveals that the light-emitting element 1 emits green light originating from $[Ir(ppy)_3]$ functioning as the light-emitting substance.

Figure 25:
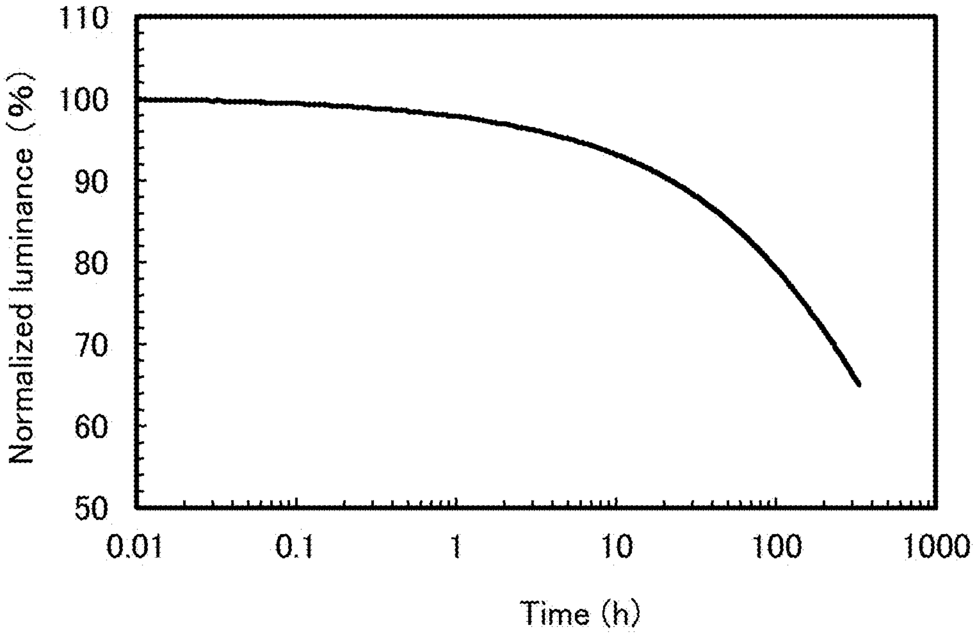
FIG. 25 shows time dependence of normalized luminance of a light-emitting element 1.

FIG. 25 shows the results of a reliability test in which the light-emitting element 1 was driven under conditions that the initial luminance was 5000 cd/$m^2$ and the current density was constant. FIG. 25 shows a change in normalized luminance from an initial luminance of 100%. The results show that a decrease in luminance over driving time of the light-emitting element 1 is small, and thus the light-emitting element 1 has favorable reliability.

EXAMPLE 4

This example will explain a light-emitting element (a light-emitting element 2). In the light-emitting element, 4mDBTBPBfpm-II that is the compound having the benzofuropyrimidine skeleton and described in Embodiment 1 was used as a host material in a light-emitting layer that contained a phosphorescent substance emitting green.

The molecular structures of compounds used in this example are shown in Structural Formulae (i) to (iii), (v), (vi), and (100) below. The element structure in FIG. 1A was employed.

(i)

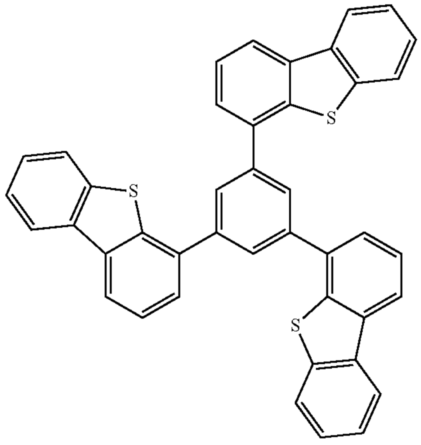

DBT3P-II (ii)

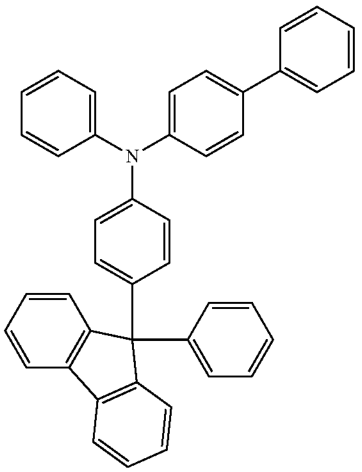

BPAFLP (100)

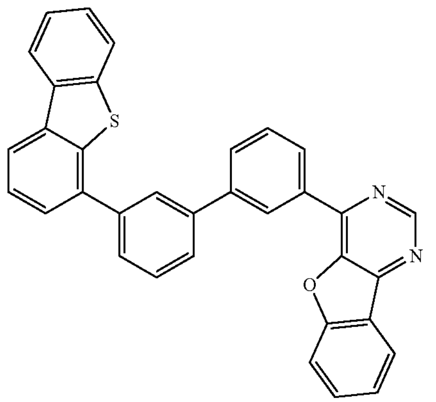

4mDBTBPBfpm-II

-continued (vi)

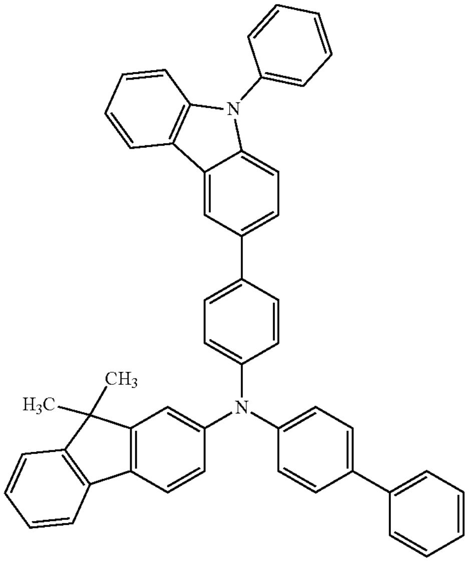

PCBBiF (iii)

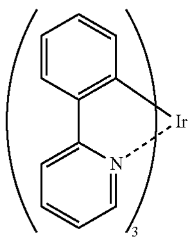

Ir(ppy)$_3$ (v)

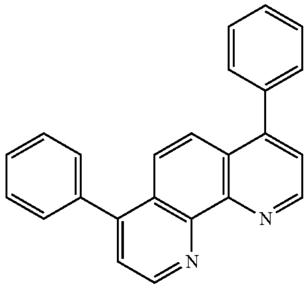

BPhen

<<Fabrication of Light-Emitting Element 2>>

First, a glass substrate, over which a film of indium tin oxide containing silicon (ITSO) was formed to a thickness of 110 nm as the first electrode 101, was prepared. A surface of the ITSO film was covered with a polyimide film so that an area of 2 mm×2 mm of the surface was exposed. As pretreatment for forming the light-emitting element over the substrate, the surface of the substrate was washed with water and baked at 200° C. for 1 hour, and then UV-ozone treatment was performed for 370 seconds. After that, the substrate was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate was cooled down for about 30 minutes.

Then, the substrate was fixed to a holder provided in the vacuum evaporation apparatus so that the surface provided with ITSO faced downward.

The pressure in the vacuum evaporation apparatus was reduced to $10^{-4}$ Pa. Then, 4,4',4"-(benzene-1,3,5-triyl)tri(dibenzothiophene) (abbreviation: DBT3P-II) represented by Structural Formula (i) and molybdenum(VI) oxide were deposited by co-evaporation so that the weight ratio of DBT3P-II to molybdenum oxide was 4:2, whereby the hole-injection layer 111 was formed. The thickness was set to 20 nm. Note that co-evaporation is an evaporation method in which a plurality of different substances are concurrently vaporized from respective different evaporation sources.

Next, 4-phenyl-4'-(9-phenylfluoren-9-yl)triphenylamine (abbreviation: BPAFLP) represented by Structural Formula (ii) was deposited by evaporation to a thickness of 20 nm, whereby the hole-transport layer 112 was formed.

Moreover, 4-[3'-(dibenzothiophen-4-yl)biphenyl-3-yl]benzofuro[3,2-d]pyrimidine (abbreviation: 4mDBTBPB-fpm-II) represented by Structural Formula (100), N-(1,1'-biphenyl-4-yl)-9,9-dimethyl-N-[4-(9-phenyl-9H-carbazol-3-yl)phenyl]-9H-fluoren-2-amine (abbreviation: PCBBiF) represented by Structural Formula (vi), and tris(2-phenylpyridinato-N,$C^{2'}$)iridium(III) (abbreviation: [Ir(ppy)$_3$]) represented by Structural Formula (iii) were deposited by co-evaporation to a thickness of 20 nm on the hole-transport layer 112 so that the weight ratio of 4mDBTBPBfpm-II to PCBBiF and [Ir(ppy)$_3$] was 0.5:0.5:0.05, and then, 4mDBTBPBfpm-II, PCBBiF, and [Ir(ppy)$_3$] were deposited by co-evaporation to a thickness of 20 nm so that the weight ratio of 4mDBTBPBfpm-II to PCBBiF and [Ir(ppy)$_3$] was 0.8:0.2:0.05, whereby the light-emitting layer 113 was formed.

Next, 4mDBTBPBfpm-II was deposited by evaporation to a thickness of 10 nm, and then bathophenanthroline (abbreviation: BPhen) represented by Structural Formula (v) was deposited by evaporation to a thickness of 15 nm, whereby the electron-transport layer 114 was formed.

Then, lithium fluoride was deposited by evaporation to a thickness of 1 nm on the electron-transport layer 114, whereby the electron-injection layer 115 was formed. Lastly, a film of aluminum was formed to a thickness of 200 nm as the second electrode 102 which serves as a cathode. Thus, the light-emitting element 2 was completed. Note that in all the above evaporation steps, evaporation was performed by a resistance-heating method.

<<Operation Characteristics of Light-Emitting Element 2>>

The light-emitting element 2 obtained as described above was sealed in a glove box containing a nitrogen atmosphere so as not to be exposed to the air. Then, the operating characteristics of the light-emitting element 2 were measured. Note that the measurement was carried out at room temperature (in an atmosphere kept at 25° C.).

Figure 26:
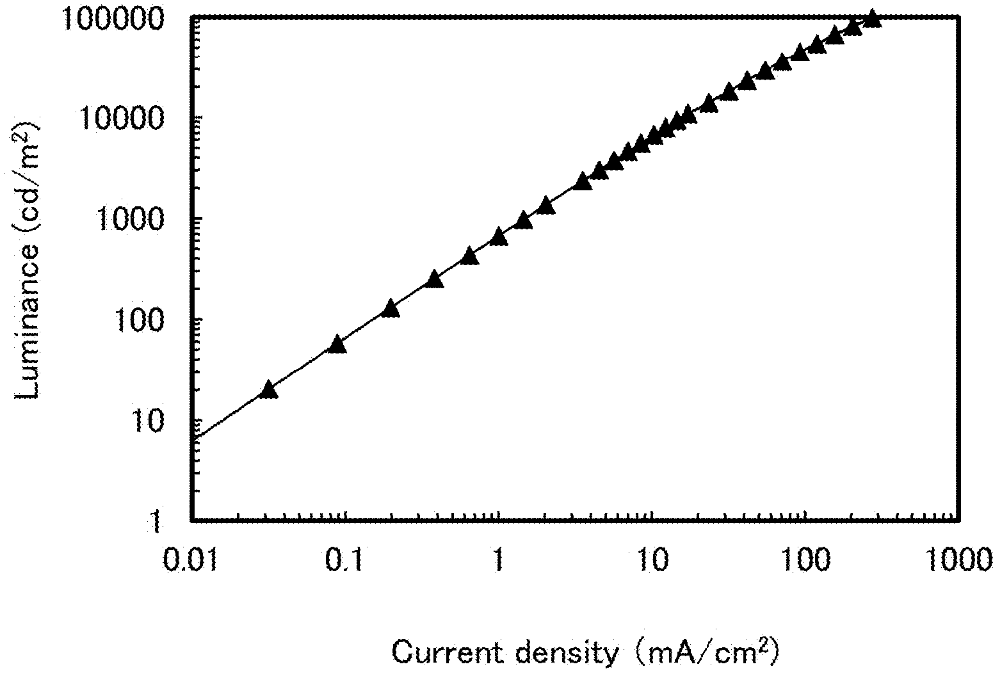
FIG. 26 shows current density-luminance characteristics of a light-emitting element 2.
Figure 27:
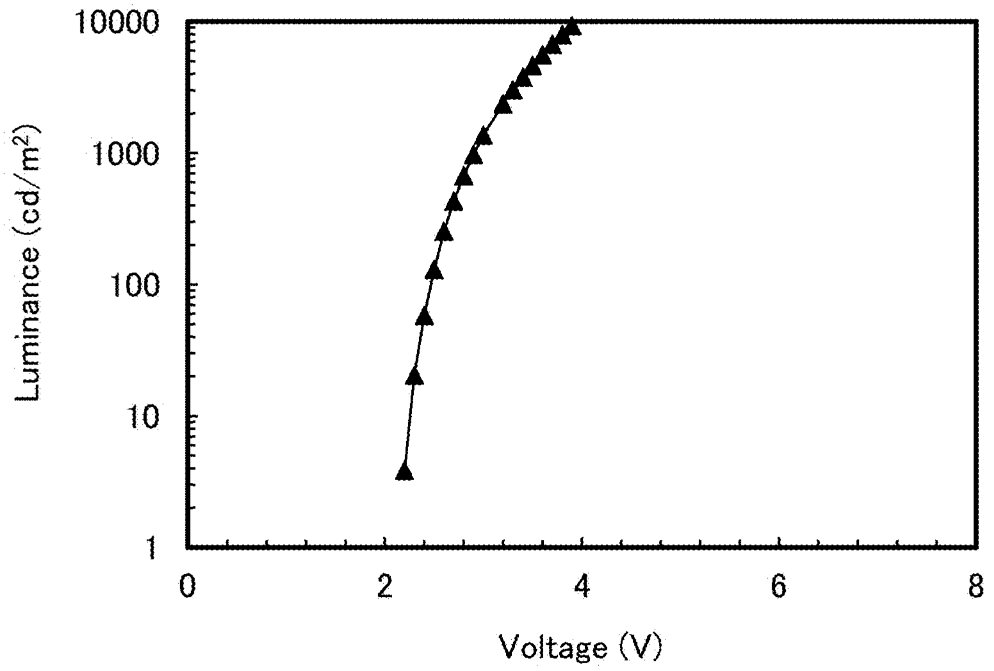
FIG. 27 shows voltage-luminance characteristics of a light-emitting element 2.
Figure 28:
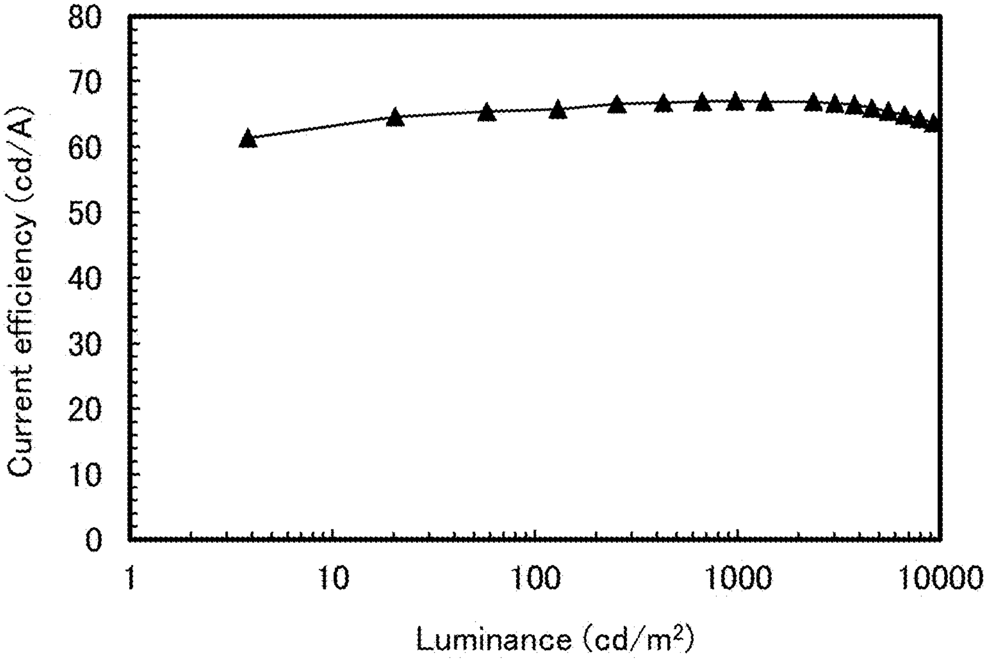
FIG. 28 shows luminance-current efficiency characteristics of a light-emitting element 2.
Figure 29:
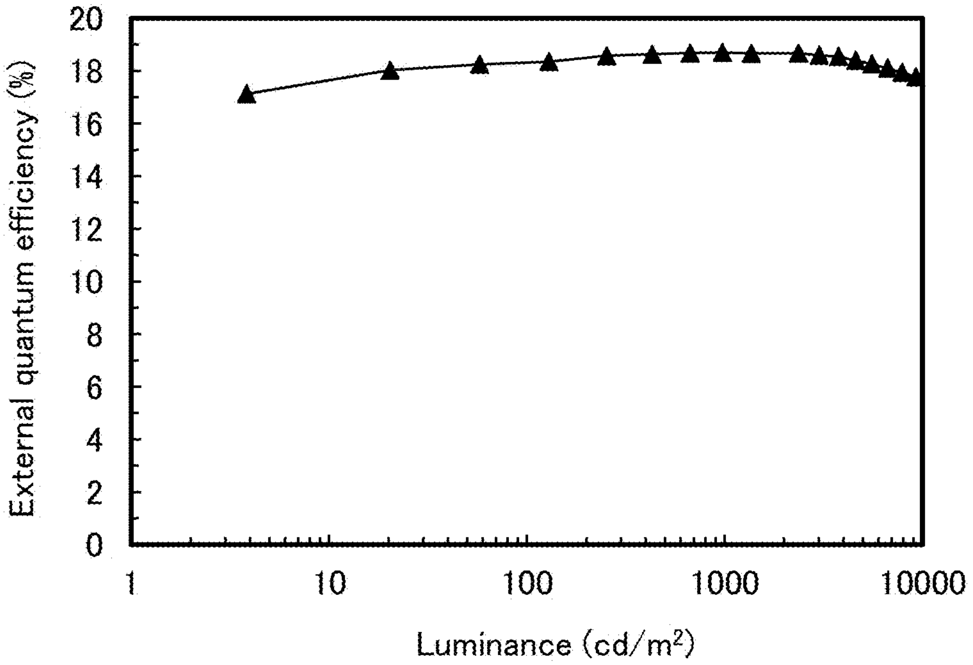
FIG. 29 shows luminance-external quantum efficiency characteristics of a light-emitting element 2.
Figure 30:
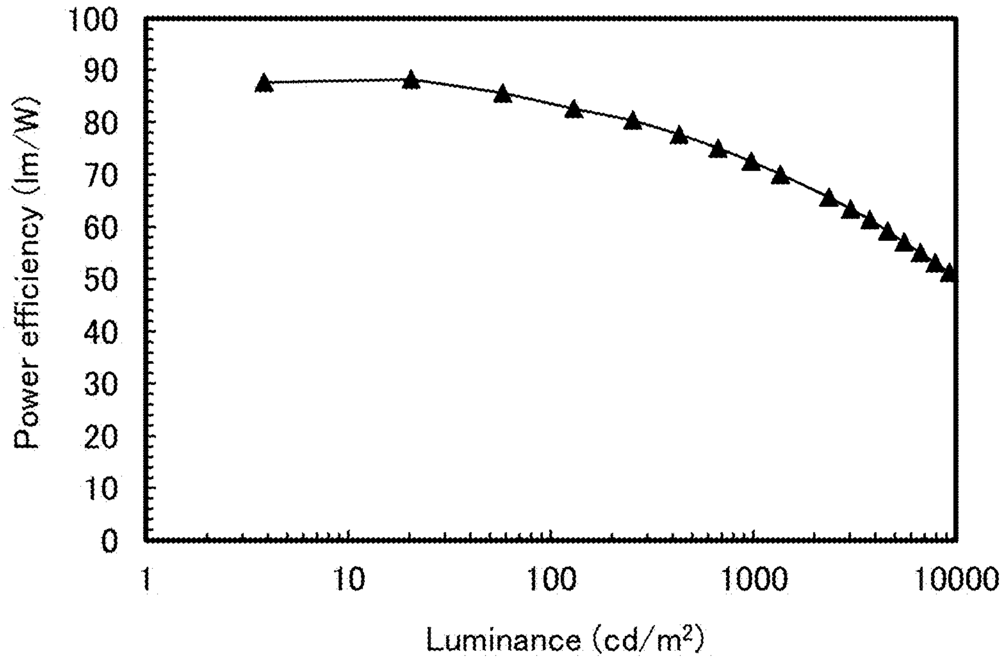
FIG. 30 shows luminance-power efficiency characteristics of a light-emitting element 2.

As to the light-emitting element 2, FIG. 26 shows the current density-luminance characteristics, FIG. 27 shows the voltage-luminance characteristics, FIG. 28 shows the luminance-current efficiency characteristics, FIG. 29 shows the luminance-external quantum efficiency characteristics, and FIG. 30 shows the luminance-power efficiency characteristics.

FIG. 28 shows that the light-emitting element 2 has high luminance-current efficiency characteristics and thus has high emission efficiency. Accordingly, 4mDBTBPBfpm-II, which is the compound having the benzofuropyrimidine skeleton and described in Embodiment 1, has a high triplet excitation level ($T_1$ level) and a wide energy gap, and allows even a phosphorescent substance emitting green to be effectively excited. Moreover, FIG. 27 shows that the light-emitting element 2 has favorable voltage-luminance characteristics and thus has low driving voltage. This means that 4mDBTBPBfpm-II, which is the compound having the benzofuropyrimidine skeleton and described in Embodiment 1, has a high carrier-transport property. FIG. 26 and FIG. 29 also show that the light-emitting element 2 has favorable current density-luminance characteristics and favorable luminance-external quantum efficiency characteristics. Accordingly, the light-emitting element 2 has extremely high power efficiency as shown in FIG. 30.

Figure 31:
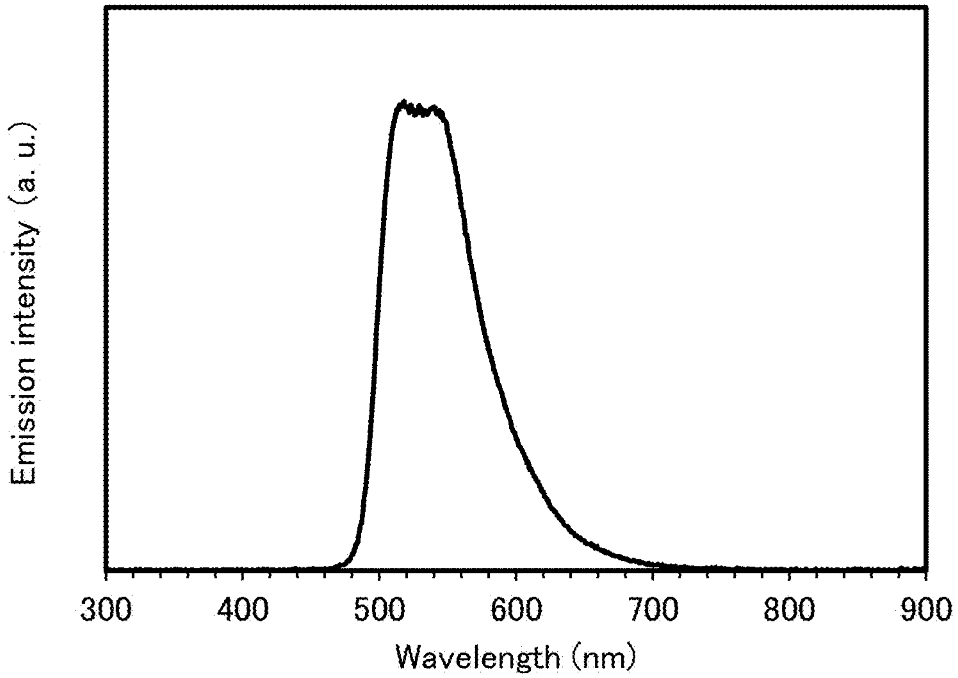
FIG. 31 shows an emission spectrum of a light-emitting element 2.

FIG. 31 shows an emission spectrum at the time when a current of 0.1 mA was made to flow in the fabricated light-emitting element 2. The emission intensity is shown as a value relative to the maximum emission intensity assumed to be 1. FIG. 31 reveals that the light-emitting element 2 emits green light originating from [$Ir(ppy)_3$] functioning as the light-emitting substance.

Figure 32:
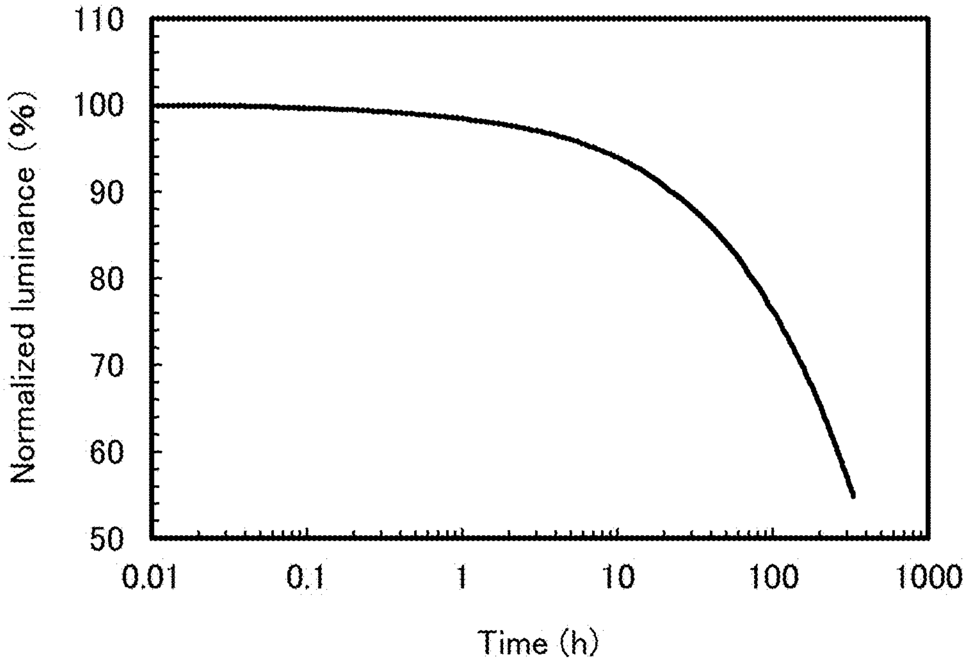
FIG. 32 shows time dependence of normalized luminance of a light-emitting element 2.

FIG. 32 shows the results of a reliability test in which the light-emitting element 2 was driven under conditions that the initial luminance was 5000 $cd/m^2$ and the current density was constant. FIG. 32 shows a change in normalized luminance from an initial luminance of 100%. The results show that a decrease in luminance over driving time of the light-emitting element 2 is small, and thus the light-emitting element 2 has favorable reliability.

EXAMPLE 5

In this example, a light-emitting element (a light-emitting element 3) will be described. In the light-emitting element, 4mDBTBPBfpm-II that is the compound having the benzofuropyrimidine skeleton and described in Embodiment 1 was used as a host material in a light-emitting layer that contained a phosphorescent substance emitting yellowish green.

The molecular structures of compounds used in this example are shown in Structural Formulae (i), (ii), (v) to (vii), and (100) below. The element structure in FIG. 1A was employed.

(i)

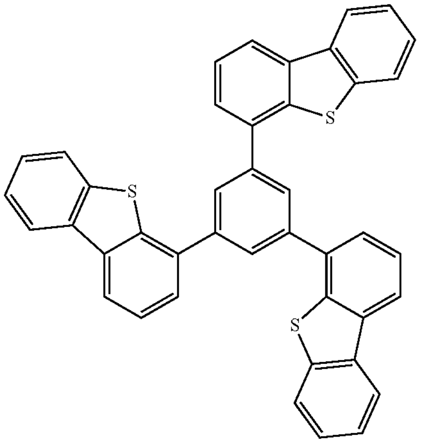

DBT3P-II

-continued (ii)

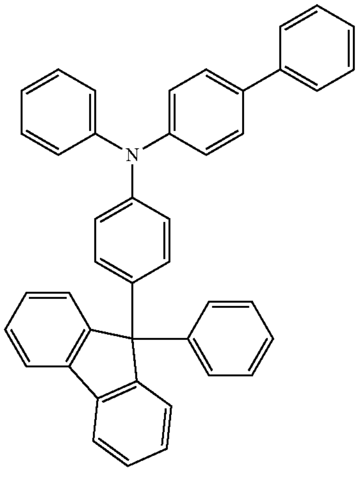

BPAFLP (100)

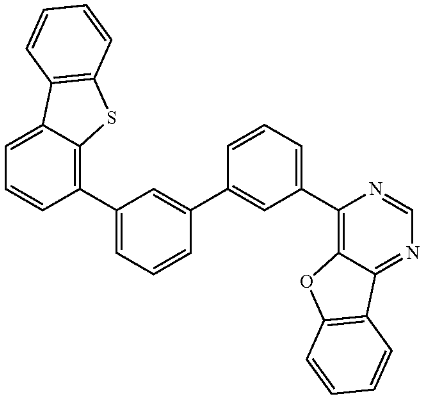

4mDBTBPBfpm-II (vi)

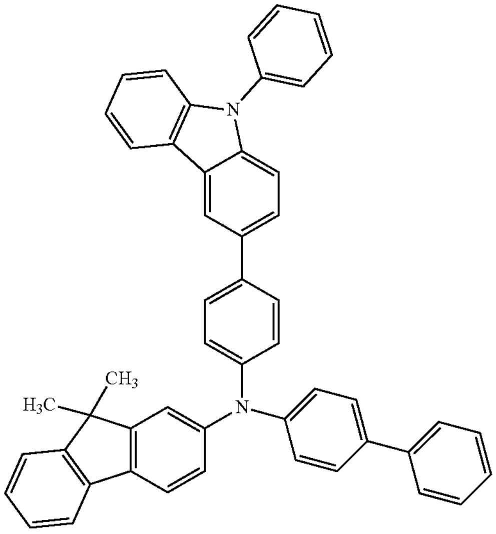

PCBBiF

-continued (vii)

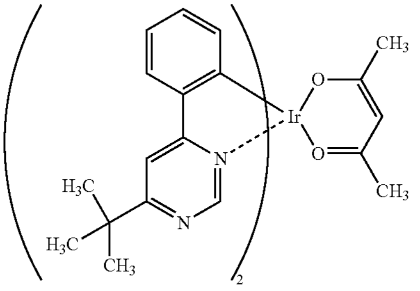

Ir(tBuppm)$_2$(acac)

(v)

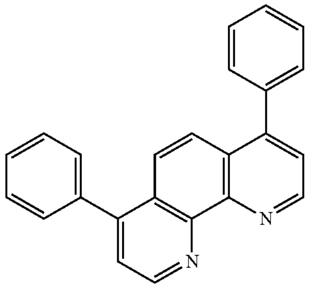

BPhen

<<Fabrication of Light-Emitting Element 3>>

First, a glass substrate, over which a film of indium tin oxide containing silicon (ITSO) was formed to a thickness of 110 nm as the first electrode 101, was prepared. A surface of the ITSO film was covered with a polyimide film so that an area of 2 mm×2 mm of the surface was exposed. As pretreatment for forming the light-emitting element over the substrate, the surface of the substrate was washed with water and baked at 200° C. for 1 hour, and then UV-ozone treatment was performed for 370 seconds. After that, the substrate was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate was cooled down for about 30 minutes.

Then, the substrate was fixed to a holder provided in the vacuum evaporation apparatus so that the surface provided with ITSO faced downward.

The pressure in the vacuum evaporation apparatus was reduced to $10^{-4}$ Pa. Then, 4,4',4''-(benzene-1,3,5-triyl)tri(dibenzothiophene) (abbreviation: DBT3P-II) represented by Structural Formula (i) and molybdenum(VI) oxide were deposited by co-evaporation so that the weight ratio of DBT3P-II to molybdenum oxide was 4:2, whereby the hole-injection layer 111 was formed. The thickness was set to 20 nm. Note that co-evaporation is an evaporation method in which a plurality of different substances are concurrently vaporized from respective different evaporation sources.

Next, 4-phenyl-4'-(9-phenylfluoren-9-yl)triphenylamine (abbreviation: BPAFLP) represented by Structural Formula (ii) was deposited by evaporation to a thickness of 20 nm, whereby the hole-transport layer 112 was formed.

Moreover, 4-[3'-(dibenzothiophen-4-yl)biphenyl-3-yl]benzofuro[3,2-d]pyrimidine (abbreviation: 4mDBTBPBfpm-II) represented by Structural Formula (100), N-(1,1'-biphenyl-4-yl)-9,9-dimethyl-N-[4-(9-phenyl-9H-carbazol-3-yl)phenyl]-9H-fluoren-2-amine (abbreviation: PCBBiF) represented by Structural Formula (vi), and bis[2-(6-tert-butyl-4-pyrimidinyl-κN3)phenyl-κC](2,4-pentanedionato-κ$^2$O,O')iridium(III) (abbreviation: [Ir(tBuppm)$_2$(acac)]) represented by Structural Formula (iii) were deposited by co-evaporation to a thickness of 20 nm on the hole-transport layer 112 so that the weight ratio of 4mDBTBPBfpm-II to PCBBiF and [Ir(tBuppm)$_2$(acac)] was 0.5:0.5:0.05, and then, 4mDBTBPBfpm-II, PCBBiF, and [Ir(tBuppm)$_2$(acac)] were deposited by co-evaporation to a thickness of 20 nm so that the weight ratio of 4mDBTBPBfpm-II to PCBBiF and [Ir(tBuppm)$_2$(acac)] was 0.8:0.2:0.05, whereby the light-emitting layer 113 was formed.

Next, 4mDBTBPBfpm-II was deposited by evaporation to a thickness of 10 nm, and then bathophenanthroline (abbreviation: BPhen) represented by Structural Formula (v) was deposited by evaporation to a thickness of 15 nm, whereby the electron-transport layer 114 was formed.

Then, lithium fluoride was deposited by evaporation to a thickness of 1 nm on the electron-transport layer 114, whereby the electron-injection layer 115 was formed. Lastly, a film of aluminum was formed to a thickness of 200 nm as the second electrode 102 which serves as a cathode. Thus, the light-emitting element 3 was completed. Note that in all the above evaporation steps, evaporation was performed by a resistance-heating method.

<<Operation Characteristics of Light-Emitting Element 3>>

The light-emitting element 3 obtained as described above was sealed in a glove box containing a nitrogen atmosphere so as not to be exposed to the air. Then, the operating characteristics of the light-emitting element 3 were measured. Note that the measurement was carried out at room temperature (in an atmosphere kept at 25° C.).

Figure 33:
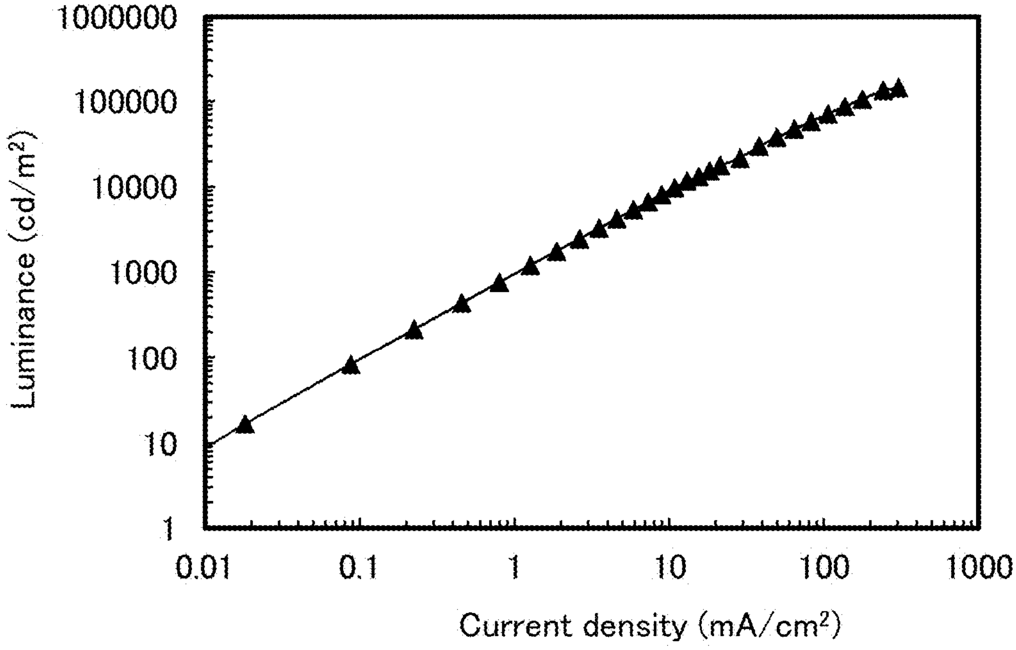
FIG. 33 shows current density-luminance characteristics of a light-emitting element 3.
Figure 34:
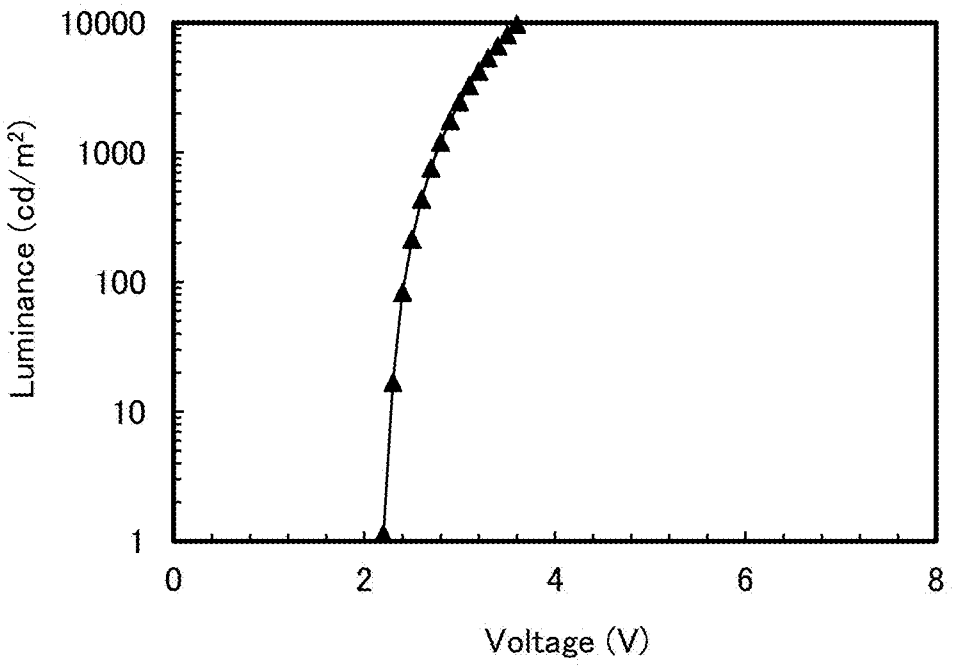
FIG. 34 shows voltage-luminance characteristics of a light-emitting element 3.
Figure 35:
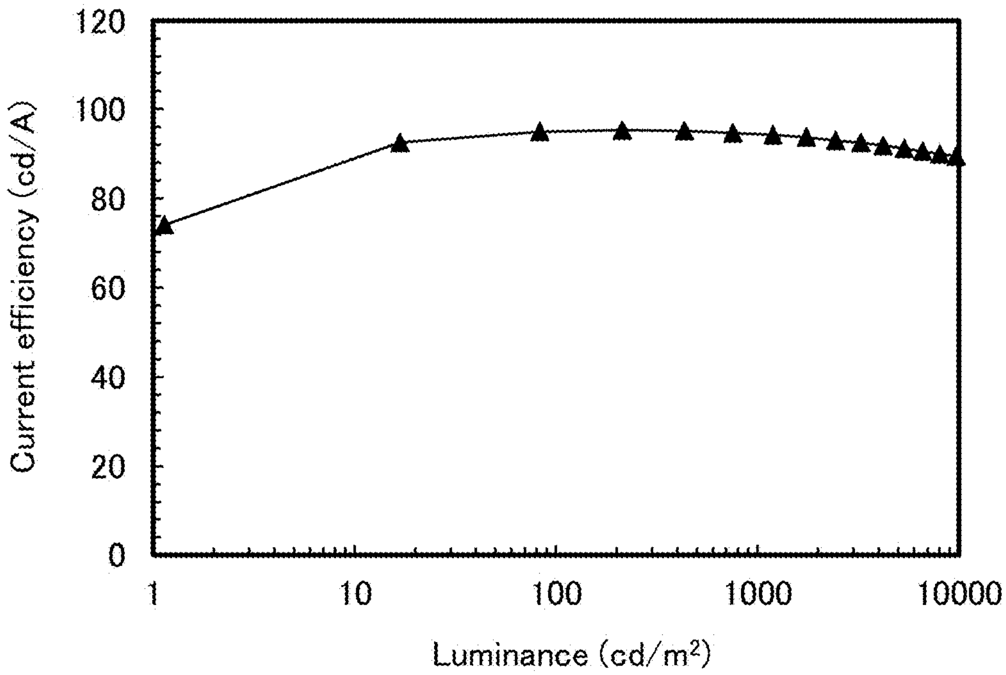
FIG. 35 shows luminance-current efficiency characteristics of a light-emitting element 3.
Figure 36:
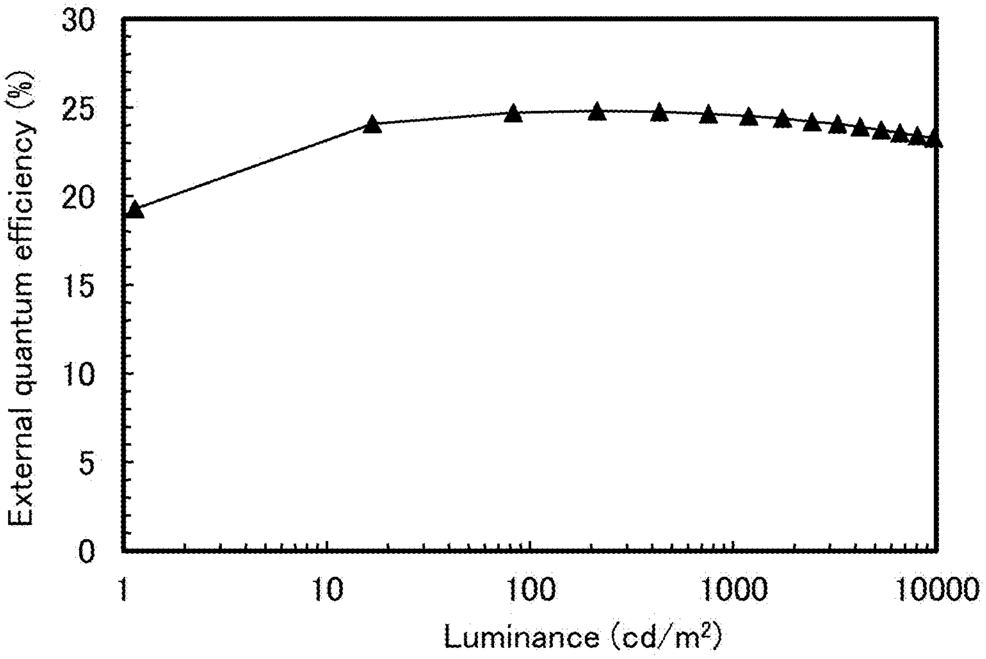
FIG. 36 shows luminance-external quantum efficiency characteristics of a light-emitting element 3.
Figure 37:
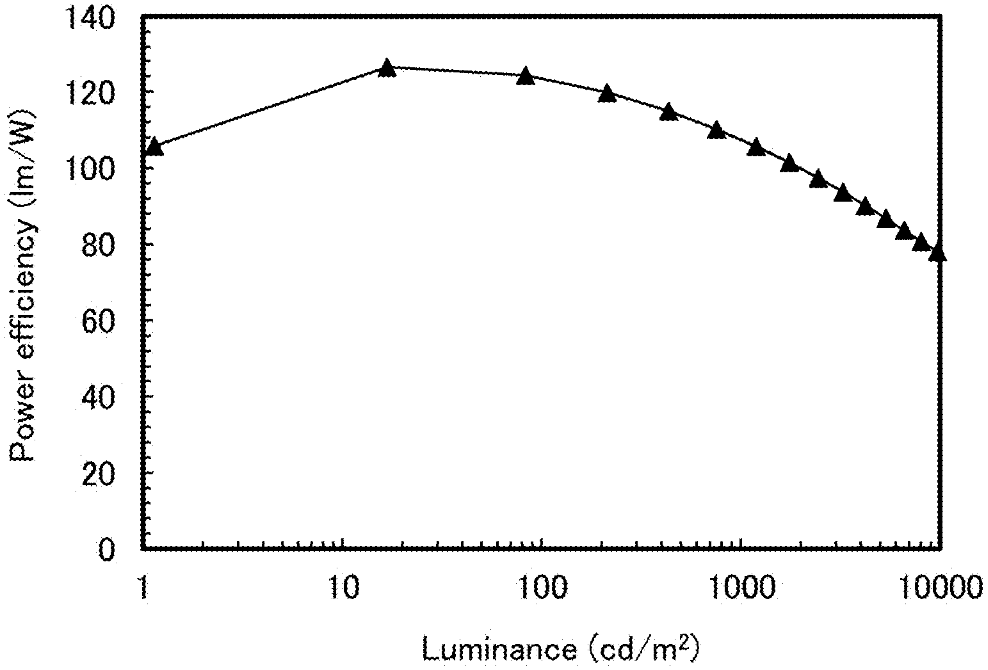
FIG. 37 shows luminance-power efficiency characteristics of a light-emitting element 3.

As to the light-emitting element 3, FIG. 33 shows the current density-luminance characteristics, FIG. 34 shows the voltage-luminance characteristics, FIG. 35 shows the luminance-current efficiency characteristics, FIG. 36 shows the luminance-external quantum efficiency characteristics, and FIG. 37 shows the luminance-power efficiency characteristics.

FIG. 35 shows that the light-emitting element 3 has high luminance-current efficiency characteristics and thus has high emission efficiency. Accordingly, 4mDBTBPBfpm-II, which is the compound having the benzofuropyrimidine skeleton and described in Embodiment 1, has a high triplet excitation level ($T_1$ level) and a wide energy gap, and allows even a phosphorescent substance emitting yellowish green to be effectively excited. Moreover, FIG. 34 shows that the light-emitting element 3 has favorable voltage-luminance characteristics and thus has low driving voltage. This means that 4mDBTBPBfpm-II, which is the compound having the benzofuropyrimidine skeleton and described in Embodiment 1, has a high carrier-transport property. FIG. 33 and FIG. 36 also show that the light-emitting element 3 has extremely favorable current density-luminance characteristics and favorable luminance-external quantum efficiency characteristics. Accordingly, the light-emitting element 3 has extremely high power efficiency as shown in FIG. 37.

Figure 38:
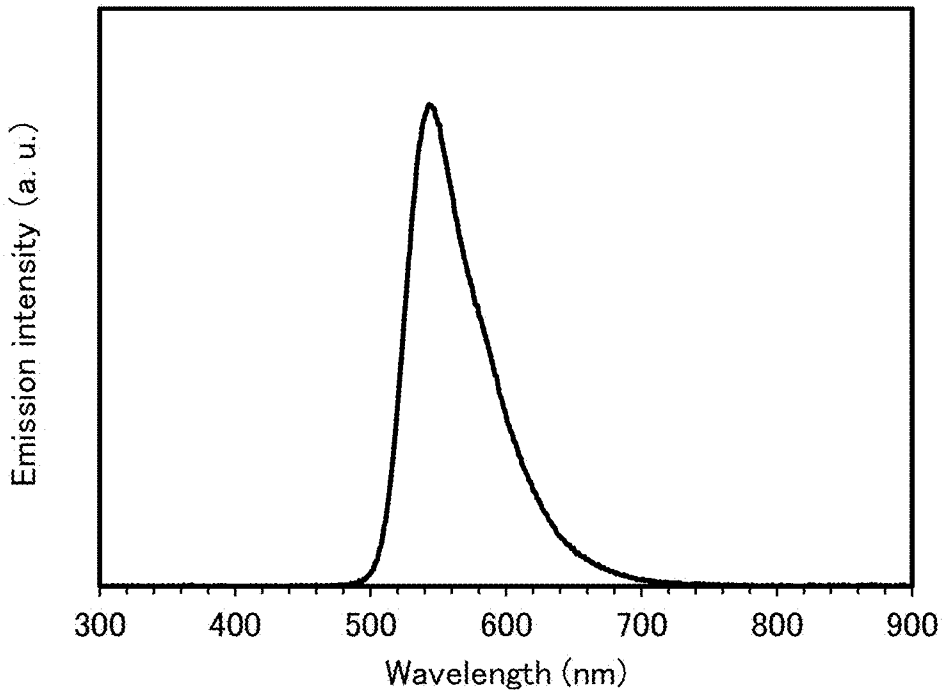
FIG. 38 shows an emission spectrum of a light-emitting element 3.

FIG. 38 shows an emission spectrum at the time when a current of 0.1 mA was made to flow in the fabricated light-emitting element 3. The emission intensity is shown as a value relative to the maximum emission intensity assumed to be 1. FIG. 38 reveals that the light-emitting element 3 emits yellowish green light originating from [Ir(tBuppm)$_2$(acac)] functioning as the light-emitting substance.

Figure 39:
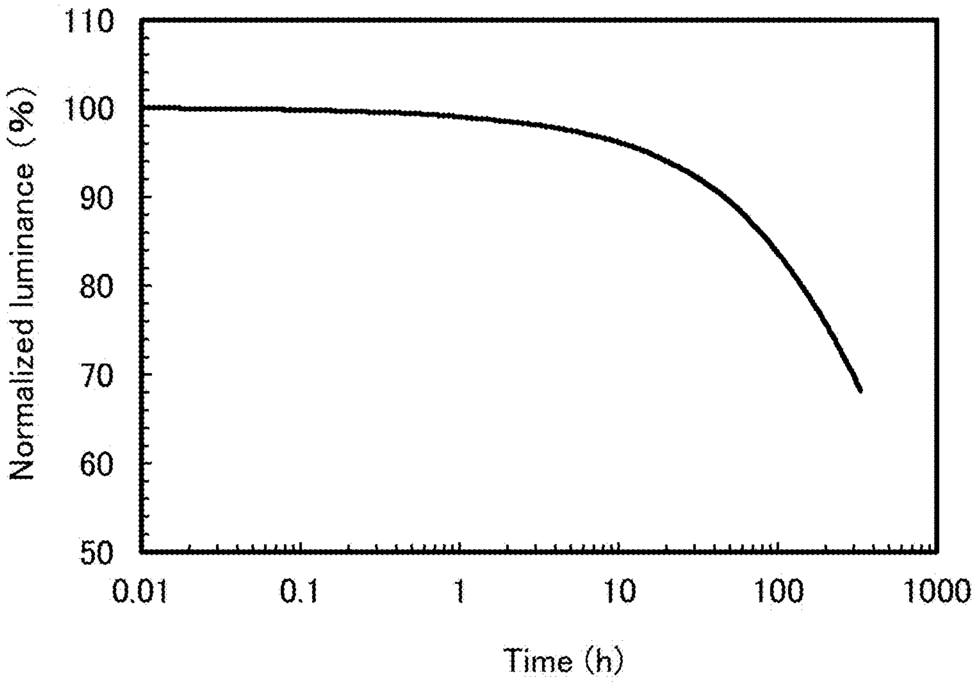
FIG. 39 shows time dependence of normalized luminance of a light-emitting element 3.

FIG. 39 shows the results of a reliability test in which the light-emitting element 3 was driven under conditions that the initial luminance was 5000 cd/$m^2$ and the current density was constant. FIG. 39 shows a change in normalized luminance from an initial luminance of 100%. The results show that a decrease in luminance over driving time of the light-emitting element 3 is small, and thus the light-emitting element 3 has favorable reliability.

EXAMPLE 6

Synthesis Example 3

In this synthesis example, a synthesis example of 4-{3-[6-(9,9-dimethylfluoren-2-yl)dibenzothiophen-4-yl]phenyl}benzofuro[3,2-d]pyrimidine (abbreviation: 4mFDBtPBfpm) that is the compound having the benzofuropyrimidine skeleton and represented by Structural Formula (115) in Embodiment 1 will be specifically described. The structural formula of 4mFDBtPBfpm is shown below.

(115)

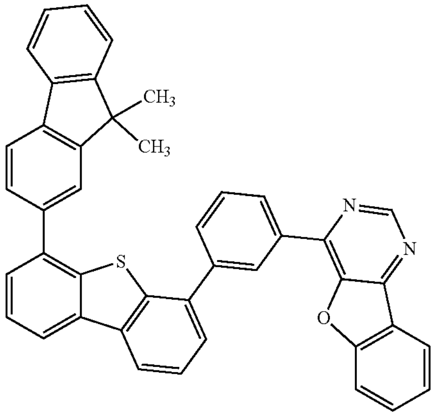

Step 1: Synthesis of 4-(9,9-Dimethylfluoren-2-yl)dibenzothiophene

First, 19 g of 2-bromo-9,9-dimethylfluorene, 16 g of dibenzothiophen-4-ylboronic acid, 0.43 g of tris(2-methylphenyl)phosphine (abbreviation: P(o-tolyl)$_3$), 35 mL of a 2 M aqueous solution of potassium carbonate, 270 mL of toluene, and 90 mL of ethanol were put in a three-neck flask equipped with a reflux pipe, and the air in the flask was replaced with nitrogen. Then, 0.16 g of palladium acetate was added, and heating was performed at 90° C. for 13 hours. Further, 0.21 g of P(o-tolyl)$_3$ and 79 mg of palladium acetate were added and heating was performed at 90° C. for 17 hours. Water was added into the resulting mixture, and extraction with toluene was performed. The solution of the extract was washed with water and a saturated aqueous solution of sodium chloride. Then, the solution was dried over magnesium sulfate and the solution obtained by the drying was filtered. The solvent in the filtrate was distilled off, and the resulting residue was dissolved in toluene. The solution was subjected to filtration through a filter aid in which Celite (Catalog No. 531-16855, manufactured by Wako Pure Chemical Industries, Ltd. (the same applies to Celite in the following description)), alumina, and Florisil (Catalog No. 540-00135, manufactured by Wako Pure Chemical Industries, Ltd. (the same applies to Florisil in the following description)) were stacked in this order. The solvent was distilled off, and purification was performed by silica gel column chromatography using toluene and hexane in a volume ratio of 1:10 as a developing solvent. The solvent in the resulting solution was distilled off and recrystallization was performed using a mixed solvent of toluene and hexane, so that a white solid was obtained in a yield of 70%. Synthesis Scheme (a-3) of Step 1 is shown below.

(a-3)

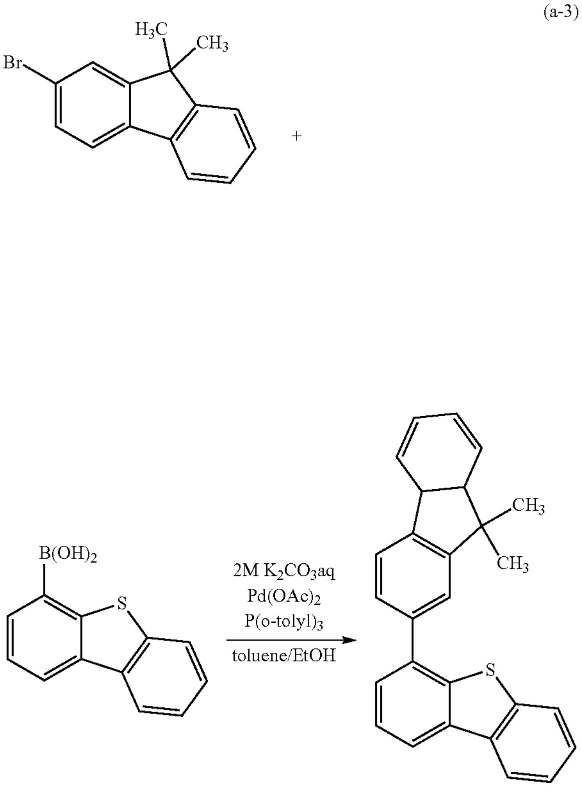

Step 2: Synthesis of 6-(9,9-Dimethylfluoren-2-yl)dibenzothiophen-4-ylboronic Acid Next, 17 g of 4-(9,9-dimethylfluoren-2-yl)dibenzothiophene was put in a three-neck flask and the air in the flask was replaced with nitrogen. Then, 250 mL of tetrahydrofuran (dehydrated) was added, the flask was cooled down to −40° C. in a cryostat, and 34 mL of a 1.6 M hexane solution of n-butyl lithium was dropped, which was followed by stirring at room temperature for 1 hour. The flask was cooled down to −40° C. Then, 6.6 mL of trimethyl borate was dropped, the temperature was raised to room temperature, and stirring was performed for 21 hours with the temperature maintained. Then, 50 mL of 1 M hydrochloric acid was added and stirring was performed for 1 hour. The resulting mixture was subjected to extraction with ethyl acetate, washing using a saturated aqueous solution of sodium hydrogen carbonate and washing using a saturated aqueous solution of sodium chloride were performed, and magnesium sulfate was added, which was followed by filtration. The solvent in the filtrate was distilled off. Toluene was added and washing using ultrasonic waves was performed. Suction filtration was performed to give a yellowish white solid in a yield of 34%. Synthesis Scheme (b-3) of Step 2 is shown below.

(b-3)

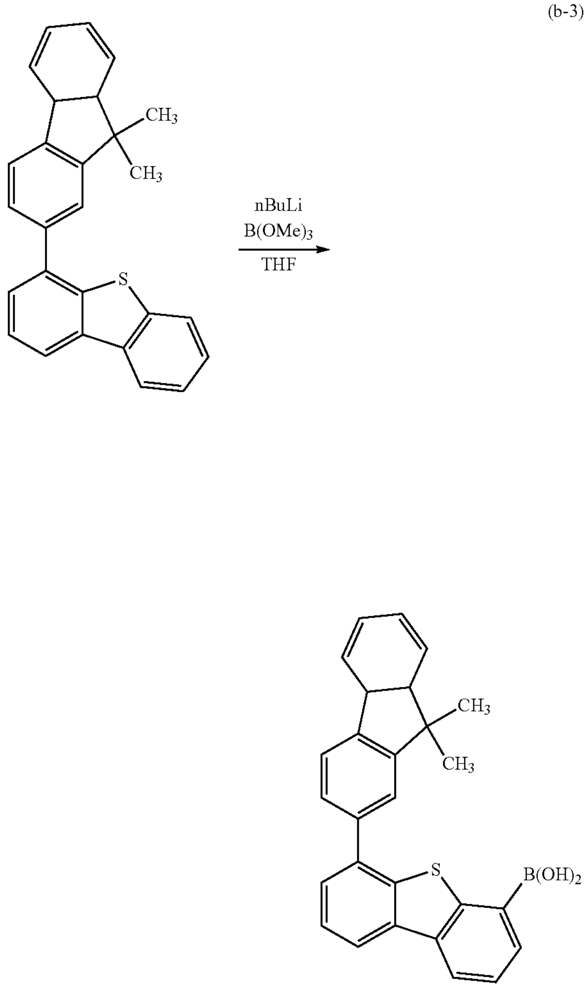

Step 3: Synthesis of 4-(3-Bromophenyl)-6-(9,9-dimethylfluoren-2-yl)dibenzothiophene Next, 7.1 g of 6-(9,9-dimethylfluoren-2-yl)dibenzothiophen-4-ylboronic acid, 5.2 g of 3-iodo-bromobenzene, 0.57 g of P(o-tolyl)$_3$, 5.1 g of potassium carbonate, 74 mL of toluene, 19 mL of ethanol, and 19 mL of water were put in a three-neck flask equipped with a reflux pipe, and the air in the flask was replaced with nitrogen. Then, 0.21 g of palladium acetate was added and heating was performed at 80° C. for 8 hours. The resulting mixture was subjected to extraction with toluene, washing using a saturated aqueous solution of sodium chloride was performed. Then, the solution was dried over magnesium sulfate and the solution obtained by the drying was filtered. The solvent in this filtrate was distilled off, and the resulting residue was dissolved in toluene. The solution was subjected to filtration through a filter aid in which Celite, alumina, and Florisil were stacked in this order. The solvent was distilled off, and purification was performed by silica gel column chromatography using toluene and hexane in a volume ratio of 1:10 as a developing solvent, whereby a yellowish white solid was obtained in a yield of 74%. Synthesis Scheme (c-3) of Step 3 is shown below.

(c-3)

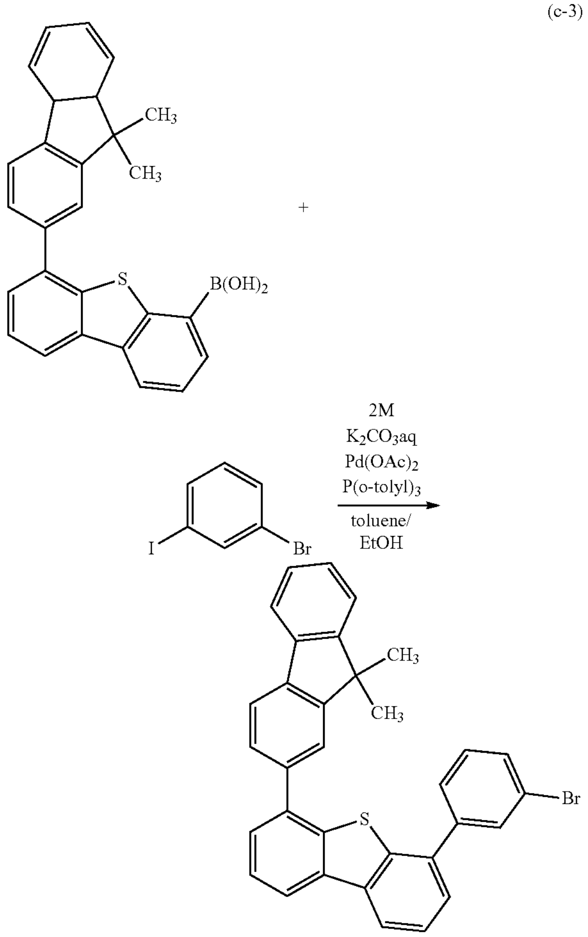

Step 4: Synthesis of 3-[6-(9,9-Dimethylfluoren-2-yl)dibenzothiophen-4-yl]phenylboronic Acid Pinacol Ester Next, 2.5 g of 4-(3-bromophenyl)-6-(9,9-dimethylfluoren-2-yl)dibenzothiophene, 1.2 g of bis(pinacol)diboron, and 1.4 g of potassium acetate were put in a three-neck flask equipped with a reflux pipe, and the air in the flask was replaced with nitrogen. Then, 300 mL of dioxane and 0.19 g of [1,1'-bis(diphenylphosphino)ferrocene]palladium(II) dichloromethane adduct (abbreviation: Pd(dppf)Cl$_2$) were added and heating was performed at 90° C. for 9.5 hours. Water was added to the resulting mixture and the solution was subjected to extraction with ethyl acetate. Washing using a saturated aqueous solution of sodium chloride was performed. Then, the solution was dried over magnesium sulfate and the solution obtained by the drying was filtered. The solvent in this filtrate was distilled off, and the resulting residue was dissolved in toluene. The solution was subjected to filtration through a filter aid in which Celite, alumina, and Florisil were stacked in this order. The solvent was distilled off, and purification was performed by flash column chromatography using toluene and hexane in a volume ratio of 1:10 as a developing solvent, whereby a colorless oily substance was obtained in a yield of 17%. Synthesis Scheme (d-3) of Step 4 is shown below.

(d-3)

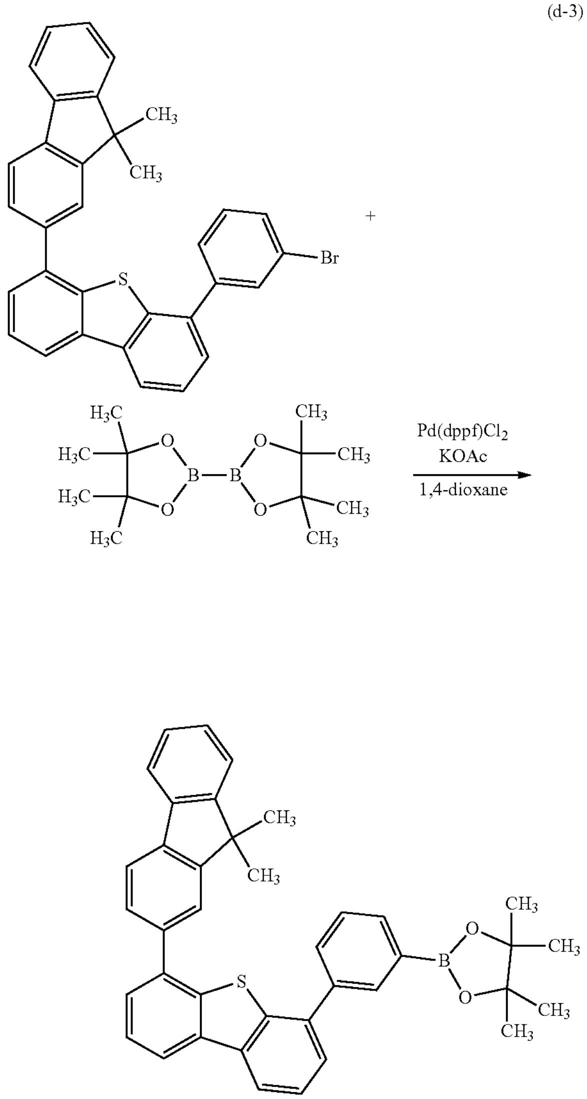

Step 5: Synthesis of 4mFDBtPBfpm

Lastly, 0.45 g of 3-[6-(9,9-dimethylfluoren-2-yl)dibenzothiophen-4-yl]phenylboronic acid pinacol ester, 0.14 g of 4-chlorobenzofuro[3,2-d]pyrimidine, 0.45 g of potassium phosphate, 4 mL of dioxane, and 0.16 g of t-butanol were put in a three-neck flask, and the air in the flask was replaced with nitrogen; then, 1.8 mg of palladium acetate and 5.6 mg of di(1-adamantyl)-n-butylphosphine were added, and the mixture was refluxed to promote a reaction. Water was added to the resulting mixture and the solution was subjected to extraction with ethyl acetate. Washing using a saturated aqueous solution of sodium chloride was performed, and magnesium sulfate was added, which was followed by gravity filtration. The solvent in the filtrate was distilled off, and purification was performed by flash column chromatography using toluene and hexane in a volume ratio of 1:5 as a developing solvent, whereby a yellow solid was obtained in a yield of 10%. Synthesis Scheme (e-3) of Step 5 is shown below.

(e-3)

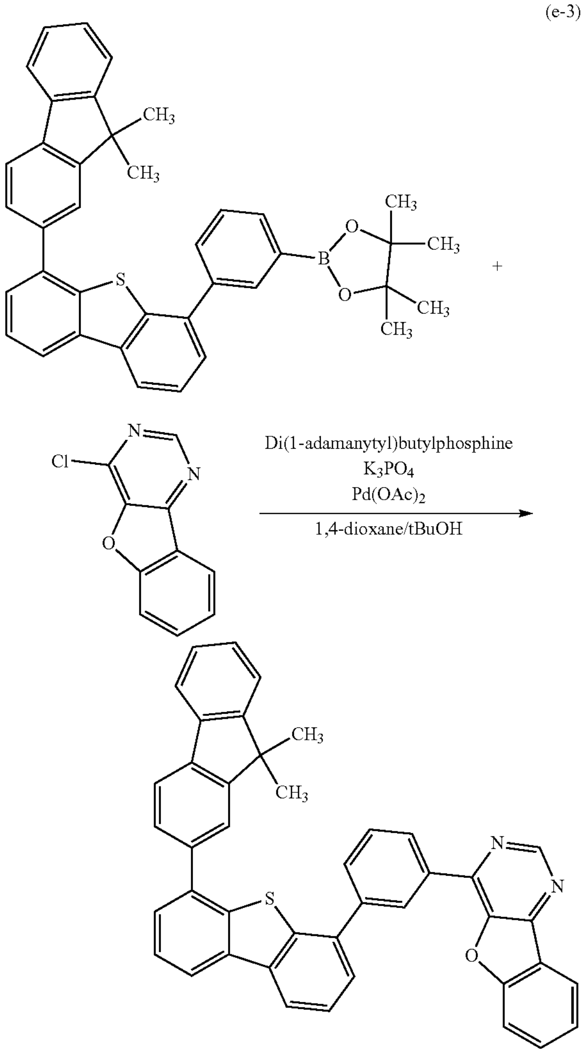

Analysis results by nuclear magnetic resonance ($^1$H-NMR) spectroscopy of the yellow solid obtained in Step 3 are described below.

$^1$H-NMR. δ($CDCl_3$): 1.37 (s, 6H), 7.28-7.31 (dt, 2H), 7.37 (d, 1H), 7.44-7.50 (m, 2H), 7.58-7.66 (m, 5H), 7.69-7.73 (m, 3H), 7.75-7.78 (t, 1H), 7.82 (s, 1H), 7.93 (d, 1H), 8.23-8.28 (m, 3H), 8.64 (td, 1H), 9.02 (ts, 1H), 9.27 (s, 1H).

Figure 40A:
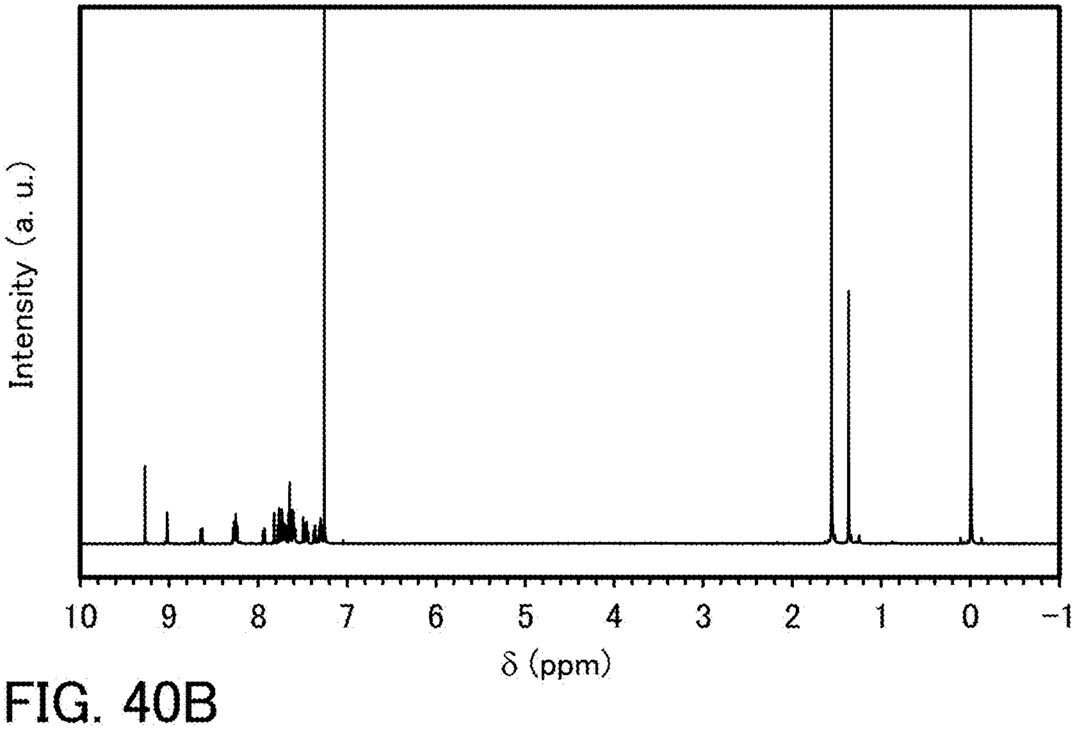
FIGS. 40A and 40B are NMR charts of 4mFDBtPBfpm.
Figure 40B:
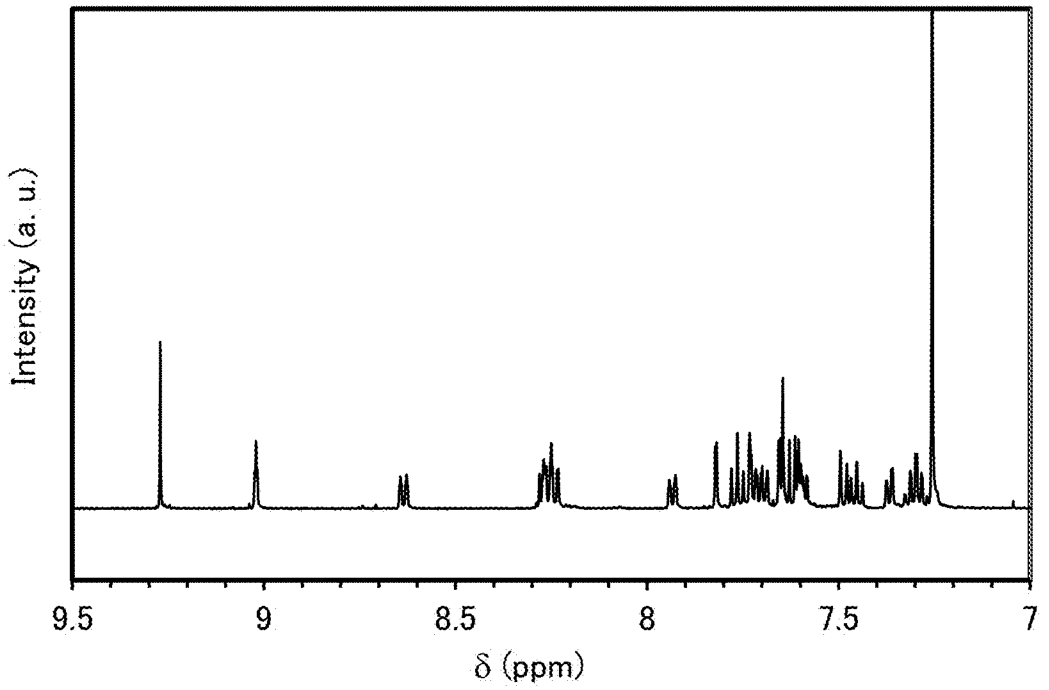

FIGS. 40A and 40B are $^1$H NMR charts. Note that FIG. 40B shows an enlarged part of FIG. 40A in the range of 7.0 ppm to 9.5 ppm. The measurement results reveal that 4mFDBtPBfpm, which was the target substance, was obtained.

REFERENCE EXAMPLE 1

In this reference example, a method for synthesizing 4,6-bis[3-(4-dibenzothienyl)phenyl]pyrimidine (abbreviation: 4,6mDBTP2Pm-II) used in Example 3 will be described.

Synthesis of 4,6-Bis[3-(4-dibenzothienyl)phenyl] pyrimidine (abbreviation: 4,6mDBTP2Pm-II)

Into a 100-mL recovery flask were put 1.0 g (6.7 mmol) of 4,6-dichloropyrimidine, 5.1 g (17 mmol) of 3-(dibenzothiophen-4-yl)phenylboronic acid, 3.5 g (34 mmol) of sodium carbonate, 20 mL of 1,3-dimethyl-3,4,5,6-tetrahydro-2(1H)pyrimidinone (abbreviation: DMPU), and 10 mL of water. This mixture was degassed by being stirred while the pressure was reduced. To this mixture was added 56 mg (81 μmol) of bis(triphenylphosphine)palladium(II) dichloride, and the atmosphere was replaced with argon. The mixture was stirred while the reaction container was heated by irradiation with microwaves (2.45 GHz, 100 W) for 1.5 hours. After the heating, water was added to the mixture, and the mixture was filtered to give a residue. The obtained solid was washed with dichloromethane and ethanol. To the obtained solid was added toluene, and the mixture was subjected to suction filtration through Celite, alumina, and Florisil. The filtrate was concentrated to give a solid. The obtained solid was recrystallized from toluene to give 2.52 g of a white solid in a yield of 63%. A synthesis scheme involving the above reaction is shown below.

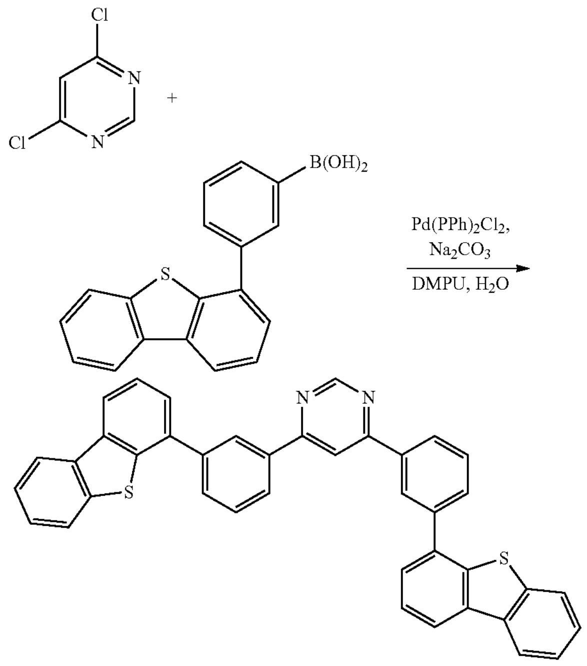

4,6mDBTP2Pm-II

By a train sublimation method, 2.50 g of the obtained solid was purified by sublimation. The purification by sublimation was performed by heating at 300° C. under a pressure of 3.6 Pa with a flow rate of argon gas of 5 mL/min. After the purification by sublimation, 1.98 g of a white solid was obtained at a collection rate of 79%.

This compound was identified as 4,6-bis[3-(4-dibenzothienyl)phenyl]pyrimidine (abbreviation: 4,6mDBTP2Pm-II), which was an objective substance, by a nuclear magnetic resonance (1H-NMR) method.

$^1$H-NMR data of the obtained substance are as follows: $^1$H NMR ($CDCl_3$, 300 MHz): δ=7.41-7.51 (m, 4H), 7.58-7.62 (m, 4H), 7.68-7.79 (m, 4H), 8.73 (dt, J1=8.4 Hz, J2=0.9 Hz, 2H), 8.18-8.27 (m, 7H), 8.54 (t, J1=1.5 Hz, 2H), 9.39 (d, J1=0.9 Hz, 1H).

REFERENCE EXAMPLE 2

In this reference example, a method for synthesizing N-(1,1'-biphenyl-4-yl)-9,9-dimethyl-N-[4-(9-phenyl-9H-carbazol-3-yl)phenyl]-9H-fluoren-2-amine (abbreviation: PCBBiF) used in Examples 4 and 5 will be described.

Step 1: Synthesis of N-(1,1'-Biphenyl-4-yl)-9,9-dimethyl-N-phenyl-9H-fluoren-2-amine In a 1-L three-neck flask were placed 45 g (0.13 mol) of N-(1,1'-biphenyl-4-yl)-9,9-dimethyl-9H-fluoren-2-amine, 36 g (0.38 mol) of sodium tert-butoxide, 21 g (0.13 mol) of bromobenzene, and 500 mL of toluene. The mixture was degassed by being stirred while the pressure was being reduced, and after the degassing, the atmosphere in the flask was replaced with nitrogen. Then, 0.8 g (1.4 mmol) of bis(dibenzylideneacetone)palladium(0) and 12 mL (5.9 mmol) of tri(tert-butyl)phosphine (a 10 wt % hexane solution) were added. A synthesis scheme of Step 1 is shown below.

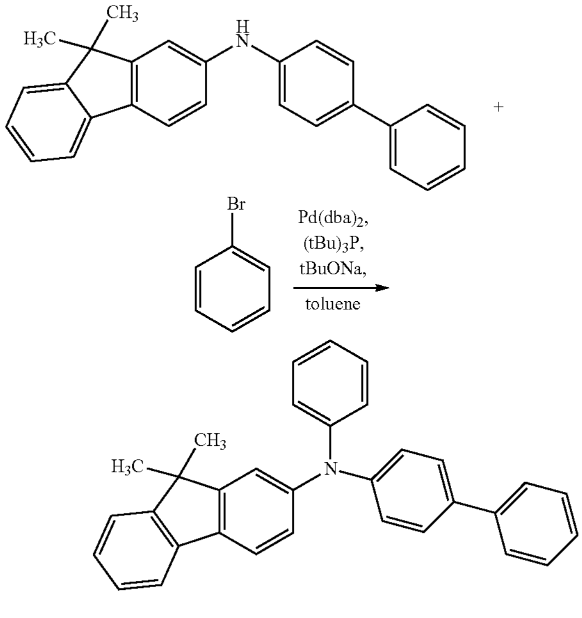

The mixture was stirred at 90° C. under a nitrogen stream for 2 hours. Then, the mixture was cooled to room temperature, and a solid was separated by suction filtration. The obtained filtrate was concentrated to give about 200 mL of a brown liquid. The brown liquid was mixed with toluene, and the resulting solution was purified using Celite, alumina, and Florisil. The resulting filtrate was concentrated to give a light yellow liquid. The light yellow liquid was recrystallized from hexane to give 52 g of target light yellow powder in a yield of 95%.

Step 2: Synthesis of N-(1,1'-Biphenyl-4-yl)-N-(4-bromophenyl)-9,9-dimethyl-9H-fluoren-2-amine In a 1-L Erlenmeyer flask was placed 45 g (0.10 mol) of N-(1,1'-biphenyl-4-yl)-9,9-dimethyl-N-phenyl-9H-fluoren-2-amine, which was dissolved in 225 mL of toluene by stirring while being heated. After the solution was naturally cooled to room temperature, 225 mL of ethyl acetate and 18 g (0.10 mol) of N-bromosuccinimide (abbreviation: NBS) were added, and the mixture was stirred at room temperature for 2.5 hours. After the stirring, the mixture was washed three times with a saturated aqueous solution of sodium hydrogen carbonate and once with a saturated aqueous solution of sodium chloride. Magnesium sulfate was added to the resulting organic layer, and the mixture was left still for 2 hours for drying. The mixture was subjected to gravity filtration to remove magnesium sulfate, and the resulting filtrate was concentrated to give a yellow liquid. The yellow liquid was mixed with toluene, and the solution was purified using Celite, alumina, and Florisil. The resulting solution was concentrated to give a light yellow solid. The light yellow solid was recrystallized from toluene/ethanol to give 47 g of target white powder in a yield of 89%. A synthesis scheme of Step 2 is shown below.

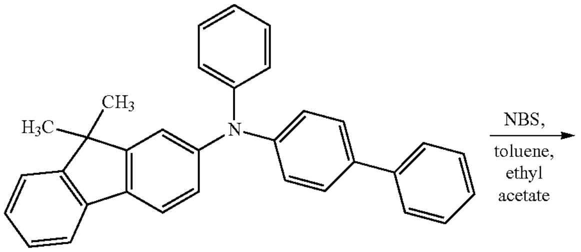

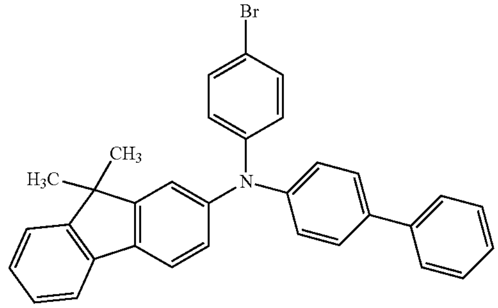

Step 3: Synthesis of PCBBiF

In a 1-L three-neck flask were placed 41 g (80 mmol) of N-(1,1'-biphenyl-4-yl)-N-(4-bromophenyl)-9,9-dimethyl-9H-fluoren-2-amine and 25 g (88 mmol) of 9-phenyl-9H-carbazol-3-ylboronic acid, to which 240 mL of toluene, 80 mL of ethanol, and 120 mL of an aqueous solution of potassium carbonate (2.0 mol/L) were added. The mixture was degassed by being stirred while the pressure was being reduced, and after the degassing, the atmosphere in the flask was replaced with nitrogen. Further, 27 mg (0.12 mmol) of palladium(II) acetate and 154 mg (0.5 mmol) of tri(ortho-tolyl)phosphine were added. The mixture was degassed again by being stirred while the pressure was being reduced, and after the degassing, the atmosphere in the flask was replaced with nitrogen. The mixture was stirred at 110° C. under a nitrogen stream for 1.5 hours. A synthesis scheme of Step 3 is shown below.

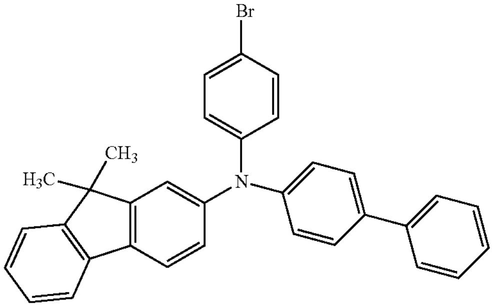

+

-continued

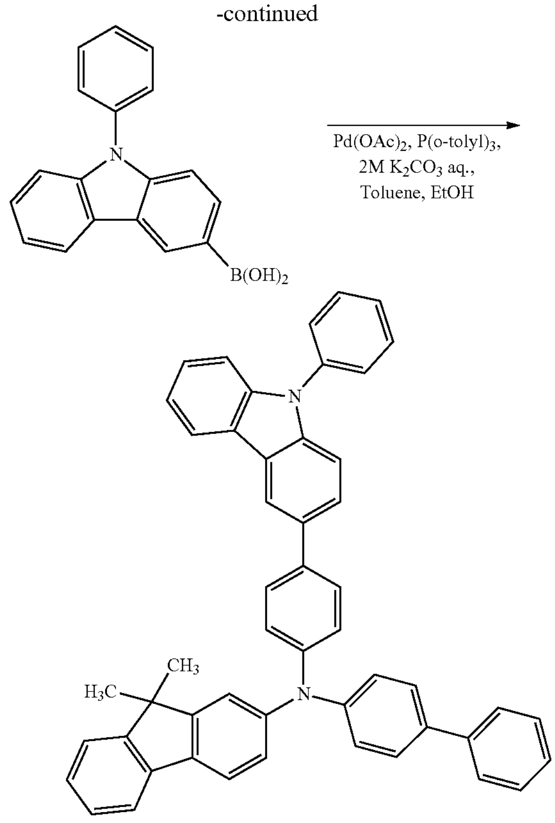

PCBBiF

After the mixture was naturally cooled to room temperature while being stirred, the aqueous layer of the mixture was extracted twice with toluene. The resulting solution of the extract and the organic layer were combined and washed twice with water and twice with a saturated aqueous solution of sodium chloride. Magnesium sulfate was added to the solution, and the mixture was left still for drying. The mixture was subjected to gravity filtration to remove magnesium sulfate, and the resulting filtrate was concentrated to give a brown solution. The brown solution was mixed with toluene, and the resulting solution was purified using Celite, alumina, and Florisil. The resulting filtrate was concentrated to give a light yellow solid. The light yellow solid was recrystallized from ethyl acetate/ethanol to give 46 g of target light yellow powder in a yield of 88%.

By a train sublimation method, 38 g of the obtained light yellow powder was purified by sublimation. In the sublimation purification, the light yellow powder was heated at 345° C. under a pressure of 3.7 Pa with an argon flow rate of 15 mL/min. After the sublimation purification, 31 g of a target light yellow solid was obtained at a collection rate of 83%.

This compound was identified as N-(1,1'-biphenyl-4-yl)-9,9-dimethyl-N-[4-(9-phenyl-9H-carbazol-3-yl)phenyl]-9H-fluoren-2-amine (abbreviation: PCBBiF), which was the target of the synthesis, by nuclear magnetic resonance (NMR) spectroscopy.

$^1$H-NMR data of the obtained light yellow solid are as follows: $^1$H-NMR ($CDCl_3$, 500 MHz): δ=1.45 (s, 6H), 7.18 (d, J=8.0 Hz, 1H), 7.27-7.32 (m, 8H), 7.40-7.50 (m, 7H), 7.52-7.53 (m, 2H), 7.59-7.68 (m, 12H), 8.19 (d, J=8.0 Hz, 1H), 8.36 (d, J=1.1 Hz, 1H).

REFERENCE NUMERALS

101: first electrode, 102: second electrode, 103: EL layer, 111: hole-injection layer, 112: hole-transport layer, 113: light-emitting layer, 114: electron-transport layer, 501: first electrode, 502: second electrode, 511: first light-emitting unit, 512: second light-emitting unit, 513: charge generation layer, 601: driver circuit portion (source side driver circuit), 602: pixel portion, 603: driver circuit portion (gate side driver circuit), 604: sealing substrate, 605: sealing material, 607: space, 608: wiring, 609: FPC (flexible printed circuit), 610: element substrate, 611: switching TFT, 612: current controlling TFT, 613: first electrode, 614: insulator, 616: EL layer, 617: second electrode, 618: light-emitting element, 623: n-channel TFT, 624: p-channel TFT, 901: housing, 902: liquid crystal layer, 903: backlight, 904: housing, 905: driver IC, 906: terminal, 951: substrate, 952: electrode, 953: insulating layer, 954: partition layer, 955: EL layer, 956: electrode, 1001: substrate, 1002: base insulating film, 1003: gate insulating film, 1006: gate electrode, 1007: gate electrode, 1008: gate electrode, 1020: first interlayer insulating film, 1021: second interlayer insulating film, 1022: electrode, 1024W: first electrode of a light-emitting element, 1024R: first electrode of a light-emitting element, 1024G: first electrode of a light-emitting element, 1024B: first electrode of a light-emitting element, 1025: partition wall, 1028: EL layer, 1029: second electrode of a light-emitting element, 1031: sealing substrate, 1032: sealant, 1033: transparent base material, 1034R: red coloring layer, 1034G: green coloring layer, 1034B: blue coloring layer, 1035: blacklayer (black matrix), 1037: third interlayer insulating film, 1040: pixel portion, 1041: driver circuit portion, 1042: peripheral portion, 1201: source electrode, 1202: active layer, 1203: drain electrode, 1204: gate electrode, 2001: housing, 2002: light source, 3001: lighting device, 5000: display region, 5001: display region, 5002: display region, 5003: display region, 5004: display region, 5005: display region, 7101: housing, 7103: display portion, 7105: stand, 7107: display portion, 7109: operation key, 7110: remote controller, 7201: main body, 7202: housing, 7203: display portion, 7204: keyboard, 7205: external connection port, 7206: pointing device, 7301: housing, 7302: housing, 7303: joint portion, 7304: display portion, 7305: display portion, 7306: speaker portion, 7307: recording medium insertion portion, 7308: LED lamp, 7309: operation key, 7310: connection terminal, 7311: sensor, 7401: housing, 7402: display portion, 7403: operation button, 7404: external connection port, 7405: speaker, 7406: microphone, 9630: housing, 9631: display portion, 9631*a*: display portion, 9631*b*: display portion, 9632*a*: touchscreen region, 9632*b*: touchscreen region, 9633: solar cell, 9634: charge and discharge control circuit, 9635: battery, 9636: DC-to-DC converter, 9637: operation key, 9638: converter, 9639: keyboard display switching button, 9033: clasp, 9034: display mode switch, 9035: power switch, 9036: power-saving switch, and 9038: operation switch This application is based on Japanese Patent Application serial no. 2013-064261 filed with Japan Patent Office on Mar. 26, 2013, the entire contents of which are hereby incorporated by reference.

The invention claimed is:

1. A mixed material for a light-emitting element comprising:

a first compound comprising a benzofuropyrimidine skeleton; and a second compound comprising a carbazolyl group, wherein the first compound and the second compound form an exciplex in a light-emitting layer of the light-emitting element.

2. A mixed material for a light-emitting element comprising:

a first compound comprising a benzofuropyrimidine skeleton and a dibenzothiophenyl group, a dibenzofuranyl group, or a carbazolyl group; and a second compound comprising a carbazolyl group, wherein the dibenzothiophenyl group, the dibenzofuranyl group, or the carbazolyl group is bonded to a pyrimidine skeleton side of the benzofuropyrimidine skeleton.

3. A light-emitting device comprising:

a pair of electrodes; and a light-emitting layer between the pair of electrodes, wherein the light-emitting layer comprises:

a light-emitting substance;

a first compound comprising a benzofuropyrimidine skeleton and a dibenzothiophenyl group, a dibenzofuranyl group, or a carbazolyl group; and a second compound comprising a carbazolyl group, and wherein the dibenzothiophenyl group, the dibenzofuranyl group, or the carbazolyl group is bonded to a pyrimidine skeleton side of the benzofuropyrimidine skeleton.

4. The mixed material for the light-emitting element according to claim 1, wherein the first compound further comprises a dibenzothiophenyl group, a dibenzofuranyl group, or a carbazolyl group, and wherein the dibenzothiophenyl group, the dibenzofuranyl group, or the carbazolyl group is bonded to a pyrimidine skeleton side of the benzofuropyrimidine skeleton.

5. The light-emitting device according to claim 3, wherein the first compound and the second compound form an exciplex.

6. The mixed material for the light-emitting element according to claim 4, wherein the first compound is represented by formula (G1):

(G1)

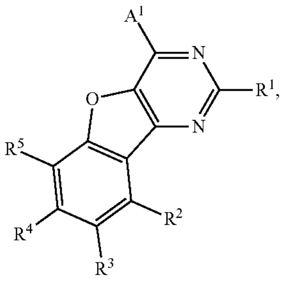

wherein $A^1$ represents a group having 6 to 100 carbon atoms, the group comprising the dibenzothiophenyl group, the dibenzofuranyl group, or the carbazolyl group, and wherein $R^1$ to $R^5$ separately represent any one of hydrogen, an alkyl group having 1 to 6 carbon atoms, a substituted or unsubstituted monocyclic saturated hydrocarbon having 5 to 7 carbon atoms, a substituted or unsubstituted polycyclic saturated hydrocarbon having 7 to 10 carbon atoms, and a substituted or unsubstituted aryl group having 6 to 13 carbon atoms.

7. The mixed material for the light-emitting element according to claim 2, wherein the first compound is represented by formula (G1):

(G1)

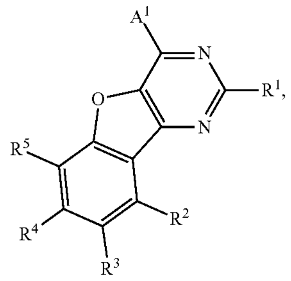

wherein $A^1$ represents a group having 6 to 100 carbon atoms, the group comprising the dibenzothiophenyl group, the dibenzofuranyl group, or the carbazolyl group, and wherein $R^1$ to $R^5$ separately represent any one of hydrogen, an alkyl group having 1 to 6 carbon atoms, a substituted or unsubstituted monocyclic saturated hydrocarbon having 5 to 7 carbon atoms, a substituted or unsubstituted polycyclic saturated hydrocarbon having 7 to 10 carbon atoms, and a substituted or unsubstituted aryl group having 6 to 13 carbon atoms.

8. The light-emitting device according to claim 3, wherein the first compound is represented by formula (G1):

(G1)

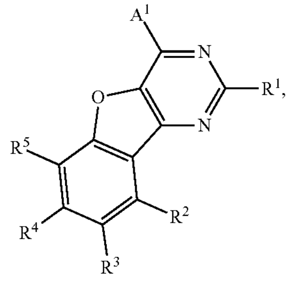

wherein $A^1$ represents a group having 6 to 100 carbon atoms, the group comprising the dibenzothiophenyl group, the dibenzofuranyl group, or the carbazolyl group, and wherein $R^1$ to $R^5$ separately represent any one of hydrogen, an alkyl group having 1 to 6 carbon atoms, a substituted or unsubstituted monocyclic saturated hydrocarbon having 5 to 7 carbon atoms, a substituted or unsubstituted polycyclic saturated hydrocarbon having 7 to 10 carbon atoms, and a substituted or unsubstituted aryl group having 6 to 13 carbon atoms.

9. The mixed material for the light-emitting element according to claim 4, wherein the first compound further comprises a phenylene group on the pyrimidine skeleton side of the benzofuropyrimidine skeleton.

10. The mixed material for the light-emitting element according to claim 2, wherein the first compound further comprises a phenylene group on the pyrimidine skeleton side of the benzofuropyrimidine skeleton.

11. The light-emitting device according to claim 3, wherein the first compound further comprises a phenylene group on the pyrimidine skeleton side of the benzofuropyrimidine skeleton.

12. The mixed material for the light-emitting element according to claim 4, wherein the first compound further comprises a phenylene group between the benzofuropyrimidine skeleton and the dibenzothiophenyl group, the dibenzofuranyl group, or the carbazolyl group.

13. The mixed material for the light-emitting element according to claim 2, wherein the first compound further comprises a phenylene group between the benzofuropyrimidine skeleton and the dibenzothiophenyl group, the dibenzofuranyl group, or the carbazolyl group.

14. The light-emitting device according to claim 3, wherein the first compound further comprises a phenylene group between the benzofuropyrimidine skeleton and the dibenzothiophenyl group, the dibenzofuranyl group, or the carbazolyl group.

15. The light-emitting device according to claim 3, wherein the light-emitting substance is a fluorescent substance.

16. The light-emitting device according to claim 3, wherein the light-emitting substance is a phosphorescent substance.

* * * * *